United States Patent [19]
Taniguchi et al.

[11] Patent Number: 5,997,473
[45] Date of Patent: Dec. 7, 1999

[54] METHOD OF LOCATING A COIL WHICH CONSISTS OF DETERMINING THE SPACE OCCUPIED BY A SOURCE COIL GENERATING A MAGNETIC FIELD

[75] Inventors: Akira Taniguchi; Kenji Kasama, both of Hachioji; Jun Hasegawa; Tetsuo Nonami, both of Hino; Hirokazu Nishimura; Katsumi Hirakawa, both of Hachioji, all of Japan

[73] Assignee: Olympus Optical Co., Ltd., Tokyo, Japan

[21] Appl. No.: 08/924,829

[22] Filed: Sep. 5, 1997

[30] Foreign Application Priority Data

| Sep. 6, 1996 | [JP] | Japan | ................................. 8-236793 |
| May 29, 1997 | [JP] | Japan | ................................. 9-140603 |

[51] Int. Cl.$^6$ ....................................................... A61B 5/05
[52] U.S. Cl. ................................................. 600/117; 600/424
[58] Field of Search ................................. 600/101, 102, 600/117, 424, 407; 128/899, 903; 324/219, 246

[56] References Cited

U.S. PATENT DOCUMENTS

| 4,176,662 | 12/1979 | Frazer . | |
| 4,821,731 | 4/1989 | Martinelli et al. . | |
| 5,253,647 | 10/1993 | Takahashi et al. | 600/117 |
| 5,273,025 | 12/1993 | Sakiyama et al. | 600/424 |
| 5,711,299 | 1/1998 | Manwaring et al. | 600/117 |
| 5,729,129 | 3/1998 | Acker | 600/424 |
| 5,840,024 | 11/1998 | Taniguchi et al. | 600/424 |

FOREIGN PATENT DOCUMENTS

| 9-028661 | 2/1997 | Japan . |
| 9-084745 | 3/1997 | Japan . |
| WO 92/03090 | 3/1992 | WIPO . |
| WO 94/04938 | 3/1994 | WIPO . |

*Primary Examiner*—John P. Leubecker
*Attorney, Agent, or Firm*—Armstrong, Westerman, Hattori, McLeland & Naughton

[57] ABSTRACT

Insertion of a probe comprising an array of 16 source coils through a forceps channel of an electronic endoscope prepares the source coils in the insert of electronic endoscope for use in monitoring work objects. To a bed where a patient lies, are mounted two sets of sensor coils crossing at a right angle to each other, each of which comprises at least four single core coils with a common central axis placed on the same line in the same direction. A control section of the system gives signals with radiofrequencies (driving signals) through source cables to the source coils, to excite the source coils to generate magnetic fields around them.

22 Claims, 44 Drawing Sheets

METHOD OF LOCATING A COIL WHICH CONSISTS OF DETERMINING THE SPACE OCCUPIED BY A SOURCE COIL GENERATING A MAGNETIC FIELD

BACKGROUND OF THE INVENTION

1. Field of the Invention

This invention relates to a method of locating a coil, more particularly to a method of locating a coil which is characterized with a source coil detecting section incorporating a plurality of single axis coils.

2. Related Art Statement

Recently, endoscopes come to be widely used in the medical field and engineering. The endoscope, especially one with an elastic insert can be inserted into a bodily cavity with a sinuous contour, and allows organs in deeper parts of the body to be observed directly without requiring surgical intervention. The endoscope further allows, when necessary, the surgeon to remove polyp or the like with a minute treatment tool inserted through it.

To insert an endoscope through a winding bodily cavity, however, requires more or less skill from the operator, as is obvious from the fact that smooth insertion of an endoscope through the anus to inspect lower digestive tracts would be impossible without a considerable skill.

For an endoscope to make a smooth insertion, it is necessary to flex the curved part of insert in accordance with bends of the body tract it follows while the insert is advancing into the body. Then, it would be valuable for the accomplishment of such feat if it becomes possible to locate the tip of insert with respect to the bodily cavity, or to see how the curved part is flexed at a time under study.

To attain this object, the prior art disclosed in PCT WO94/04938 official gazette introduces a method to locate a coil: three coils are placed at specified positions relative to each other so as to cross their long axes at right angles and to represent three axes of a coordinate system, they generate one after another AC magnetic fields whose vectors intersect at right angles in a space defined by the coordinate system, a separate single axis coil is placed at one position within the same space, and an induced voltage across both ends of the same coil is measured each time the axial coils are excited to generate a magnetic field, and the measured data are utilized to locate the solitary axis coil in the coordinate system.

The method introduced by the above-described prior art disclosed in PCT WO94/04938, however, presents with a problem: a radiofrequency signal to excite the solitary axial coil to generate a magnetic field in it comes to shift from the frequency with which a frequency component extracting means deal, because the oscillating mechanism of field generating coils is sensitive to changes in environment including ambient temperature, or being more or less ready to develop changes after long use; and this discrepancy in frequency will result in a wrong estimation of the location of the solitary coil, or the tip of an endoscope when the coil is incorporated in an endoscope, and thus will make it impossible to make a precise estimation of how the endoscope is inserted into the body at a time of interest.

To meet that problem, the prior art disclosed in Japanese Unexamined Patent Publication No. 9-28661 proposes an endoscope shape detecting apparatus wherein a frequency adjustment means is introduced that can adjust the radiofrequency to coincide with a reference frequency. Accordingly, even when this apparatus is exposed to environment which may invoke changes in the radiofrequency, or has been used over a time long enough to cause changes in the radiofrequency, the coincidence remains uninfluenced from such environmental changes and long use. This apparatus ensures a stable monitoring of the tip of an endoscope.

The method introduced by the above-described prior art disclosed in PCT WO94/04938 has another problem: it requires a plurality of three axis coils each of which comprises a combination of three single core coils crossed at right angles, to give an estimation of the location of a magnetism generating element from the results of the detection elements, and thus the system incorporating those coils is complicated in structure.

The method disclosed in Japanese Unexamined Patent Publication No. 9-28661, when applied to an endoscope, presents the same problem: it requires a plurality of three axis coils each of which is produced by combining three single core coils crossed at right angles, to locate a magnetism generating element based on the measurements by the plurality of detection elements, and thus the system incorporating the coils is complicated in structure.

The method disclosed in Japanese Unexamined Patent Publication No. 9-28661 presents still another problem: in vector analysis, frequency components comprising a signal train receive Fourier transformation, but the thus derived result does not always represent original observed frequencies. Namely, there are more or less leaks. To reduce such leaks it is necessary to introduce a widow function method for the analysis.

OBJECTS AND SUMMARY OF THE INVENTION

One object of this invention is to provide a method of locating a coil, or determining the space occupied by a coil or a magnetism generating element (or detecting element) by referring to the data derived from an array of magnetism detecting elements (or magnetism generating elements) composed of at least four single core coils placed at different points on the same axis in the same direction, which can reduce the number of variables necessary for locating the coil.

A second object of this invention is to provide a method of locating a coil which allows an estimation of the location of a magnetism generating element (or detecting element) in a space by using a plurality of arrays of magnetism detecting elements (or magnetism generating elements) each of which comprises at least four single core coils placed on the same axis at different points in the same direction.

The method of locating a coil of this invention comprises:

a first magnetic field determining process of determining the intensity of a magnetic field induced by a source coil in a first single axis coil placed around a specified axial line;

a second magnetic field determining process of determining the intensity of a magnetic field induced by the source coil in a second single axis coil placed around the same axial line but at a different place from the first one;

a third magnetic field determining process of determining the intensity of a magnetic field induced by the source coil in a third single axis coil placed around the same axial line but at a different place from foregoing first and second ones;

a fourth magnetic field determining process of determining the intensity of a magnetic field induced by the source coil in a fourth single axis coil placed around the same axial line but at a different place from foregoing first, second and third ones; and a process of determining by calculation the space occupied by the source coil from the magnetic intensity data obtained through the first, second, third and fourth magnetic intensity determining processes.

Other features and values of this invention will become obvious after following description has been attentively read through.

BRIEF DESCRIPTION OF THE DRAWINGS

FIG. 1 represents how the endoscopic system is constituted; FIG. 2 is a block diagram representing how the system of FIG. 1 is functionally constituted; FIG. 3 is a block diagram illustrating the constitution of the system of FIG. 2; FIG. 4 is a block diagram of the two port memory or one of important elements of the system of FIG. 3; FIG. 5 represents how different signals are timed in the two port memory of FIG. 4; FIG. 6 is a flowchart representing how operation proceeds in the system of FIG. 1; FIG. 7 is a flowchart representing how operation proceeds for FFT (Fourier transformation) processing; FIG. 8 represents how parallel processings are timed in the endoscopic system of FIG. 6; FIG. 9 is a first illustration representing a principle underlying the method of estimating the coordinates of the source coil of FIG. 6; FIG. 10 is a second illustration representing the principle underlying the method of estimating the coordinates of the source coil of FIG. 6; FIG. 11 is a third illustration representing the principle underlying the method of estimating the coordinates of the source coil of FIG. 6; FIG. 12 is a fourth illustration representing the principle underlying the method of estimating the coordinates of the source coil of FIG. 6; FIG. 13 is a fifth illustration representing the principle underlying the method of estimating the coordinates of the source coil of FIG. 6; FIG. 14 is a sixth illustration representing the principle underlying the method of estimating the coordinates of the source coil of FIG. 6; FIG. 15 is a seventh illustration representing the principle underlying the method of estimating the coordinates of the source coil of FIG. 6; FIG. 16 is an eighth illustration representing the principle underlying the method of estimating the coordinates of the source coil of FIG. 6; FIG. 17 is a ninth illustration representing the principle underlying the method of estimating the coordinates of the source coil of FIG. 6; FIG. 18 is a tenth illustration representing the principle underlying the method of estimating the coordinates of the source coil of FIG. 6; FIG. 19 is an eleventh illustration representing the principle underlying the method of estimating the coordinates of the source coil of FIG. 6; FIG. 20 is a first flowchart representing processes necessary for estimating the coordinates of the source coil of FIG. 6; FIG. 21 is a second flowchart representing processes necessary for estimating the coordinates of the source coil of FIG. 6; FIG. 22 is a flowchart representing processes necessary for correcting the coordinates of source coil of FIG. 6 given by the foregoing estimating processes of FIGS. 20 and 21; FIG. 23 is a flowchart representing processes necessary for displaying the detected endoscope shape as an image; FIG. 24 is a display example obtained through normal mode processing of FIG. 23; FIG. 25 is a flowchart representing processes involved in magnification processing of the image obtained in FIG. 23; FIG. 26 is a display example obtained through the magnification mode processing of FIG. 25; FIG. 27 is a first illustration outlining two types of 3D image reconstruction (3D model 1 and 2) which are used to represent the endoscope shape data obtained in FIG. 6 as a 3D image on display; FIG. 28 is a flowchart representing processes necessary for obtaining and refining 3D images of 3D model 1 and 2; FIG. 29 is a second illustration outlining two types of 3D image reconstruction (3D model 1 and 2) which are used to represent the endoscope shape data obtained in FIG. 6 as a 3D image on display; FIG. 30 is a first flowchart representing processes necessary for color correction; FIG. 31 is a first illustration representing the effect of color correction of FIG. 30; FIG. 32 is a second flowchart representing processes necessary for the color correction of FIG. 29; FIG. 33 is a second illustration representing the effect of color correction of FIG. 30; FIG. 34 is a flowchart representing processes necessary for obtaining 2D images from the endoscope shape data of FIG. 6; FIG. 35 is a display example of an endoscope shape obtained through the processes represented in FIG. 34; FIG. 36 is a flowchart representing processes necessary for obtaining a 12-point image of the endoscope shape of FIG. 6; FIG. 37 is a display example of the endoscope shape of FIG. 6 obtained through the processes represented in FIG. 36; FIG. 38 is a flowchart representing processes necessary for obtaining a dot-and-line representation of the endoscope shape of FIG. 6; and FIG. 39 is a display example of the endoscope shape of FIG. 6 obtained through the processes represented in FIG. 38.

FIG. 40 represents the constitution of an endoscope system; FIG. 41 is an illustration representing the principle underlying the method of estimating the coordinates of the source coil in the endoscope system in FIG. 40; and FIG. 42 is a flowchart representing processes necessary for estimating the coordinates of the source coil of the endoscope system in FIG. 40.

FIG. 43 represents the constitution of an endoscope system; FIG. 44 is an illustration representing the principle underlying the method of estimating the coordinates of the source coil of the endoscope system in FIG. 43; FIG. 45 is a first flowchart representing processes necessary for estimating the coordinates of the source coil of the endoscope system in FIG. 40; FIG. 46 is a second flowchart representing processes necessary for estimating the coordinates of the source coil of the endoscope system in FIG. 43; and FIG. 47 represents the constitution of a modified version of the endoscope system of FIG. 43.

Figure 48:
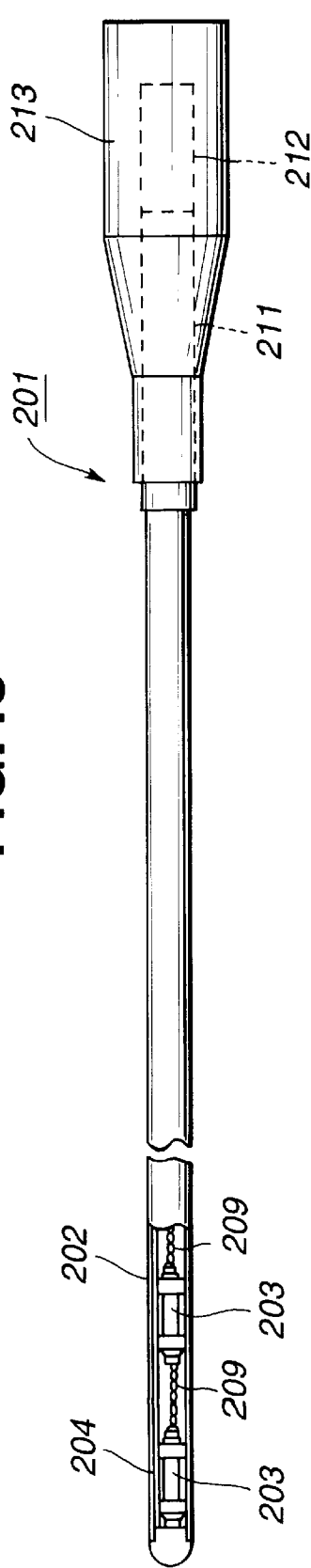

FIGS. 48–58 are related with the fourth embodiment of this invention: FIG. 48 represents a probe of an endoscope system representing the fourth embodiment; FIG. 49 gives an enlarged view of part of the probe of FIG. 48; FIG. 51 gives a first modified version of the coil apparatus for locating an endoscope of FIG. 48; FIG. 52 gives a second modified version of the coil apparatus for locating an endoscope of FIG. 48; FIG. 53 gives a third modified version of the coil apparatus for locating an endoscope of FIG. 48; FIG. 54 gives a fourth modified version of the coil apparatus for locating an endoscope of FIG. 48; FIG. 55 gives a fifth modified version of the coil apparatus for locating an endoscope of FIG. 48; FIG. 56 gives a sixth modified version of the coil apparatus for locating an endoscope of FIG. 48; FIG. 57 gives a seventh modified version of the coil apparatus for locating an endoscope of FIG. 48; and FIG. 58 gives an eighth modified version of the coil apparatus for locating an endoscope of FIG. 48.

Figure 59:
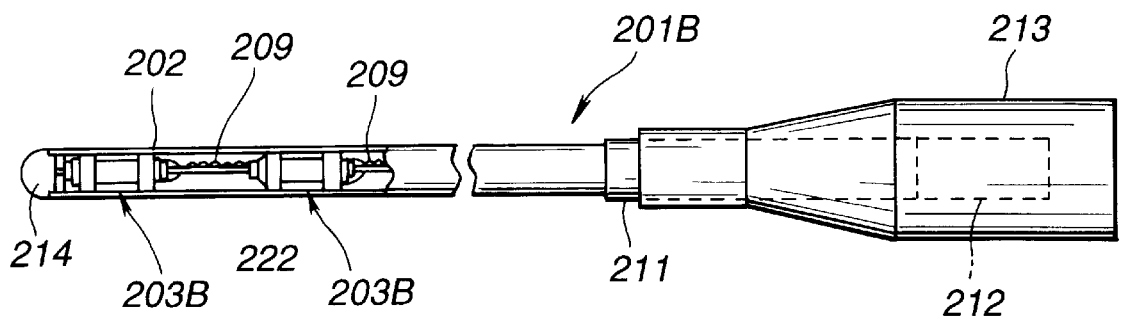
Figure 60:
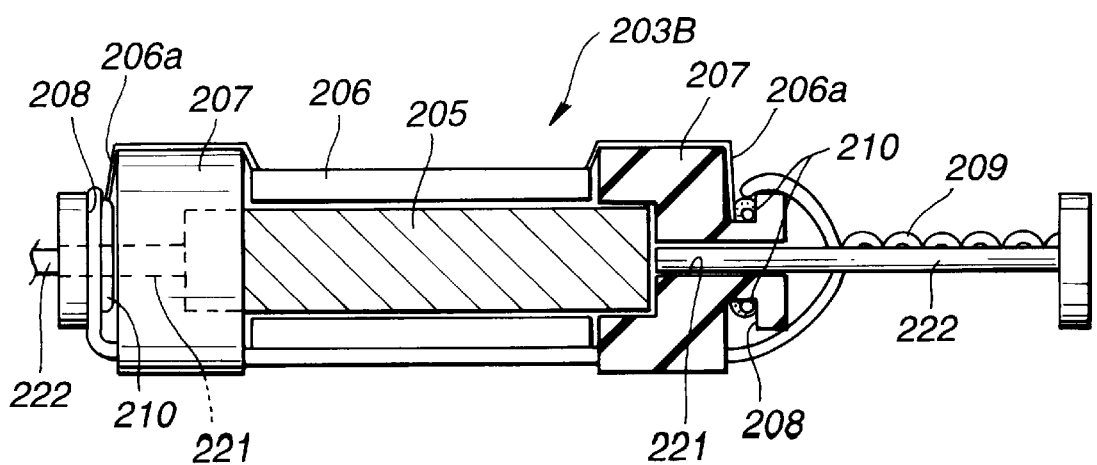
Figure 61:
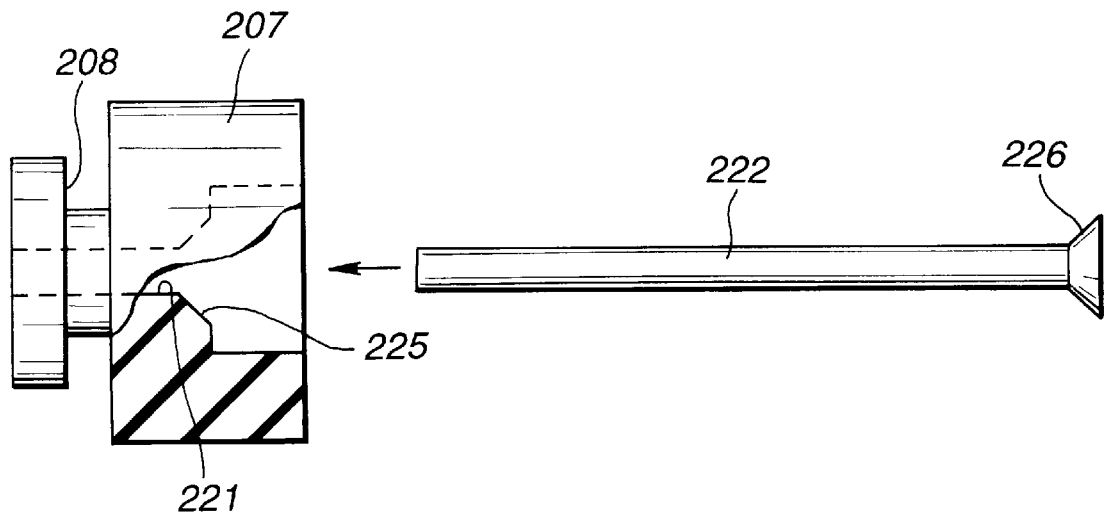

FIGS. 59–61 are related with the fifth embodiment of this invention: FIG. 59 represents a probe of an endoscope system representing the fifth embodiment; FIG. 60 gives an enlarged view of part of the probe of FIG. 59; FIG. 60 gives a lateral view of a coil apparatus whose part is cross-sectioned for illustration and which is used for locating an endoscope as represented in FIG. 59; and FIG. 61 gives a modified version of the coil apparatus of FIG. 59 with its part enlarged for illustration.

Figure 62:
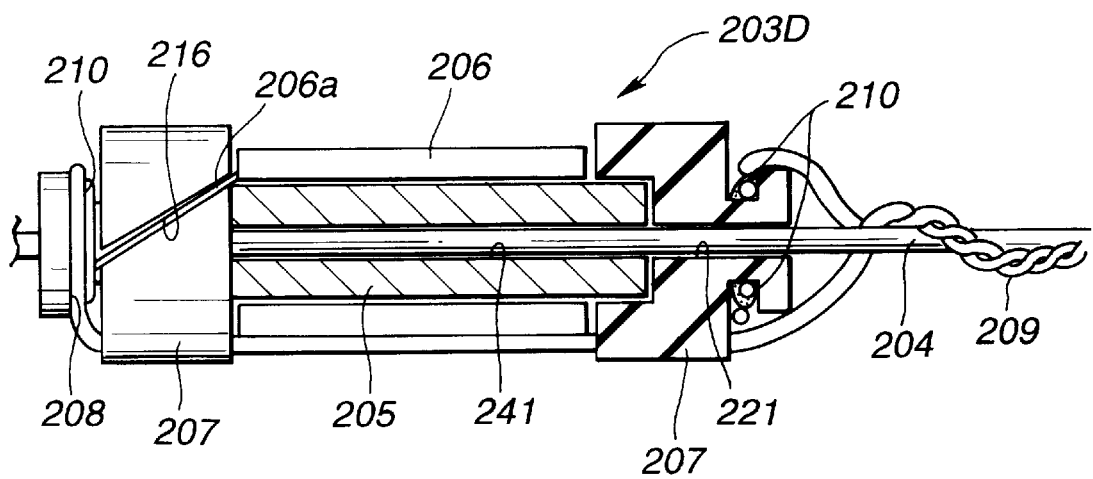

FIG. 62 gives a coil apparatus of the sixth embodiment.

Figure 63:
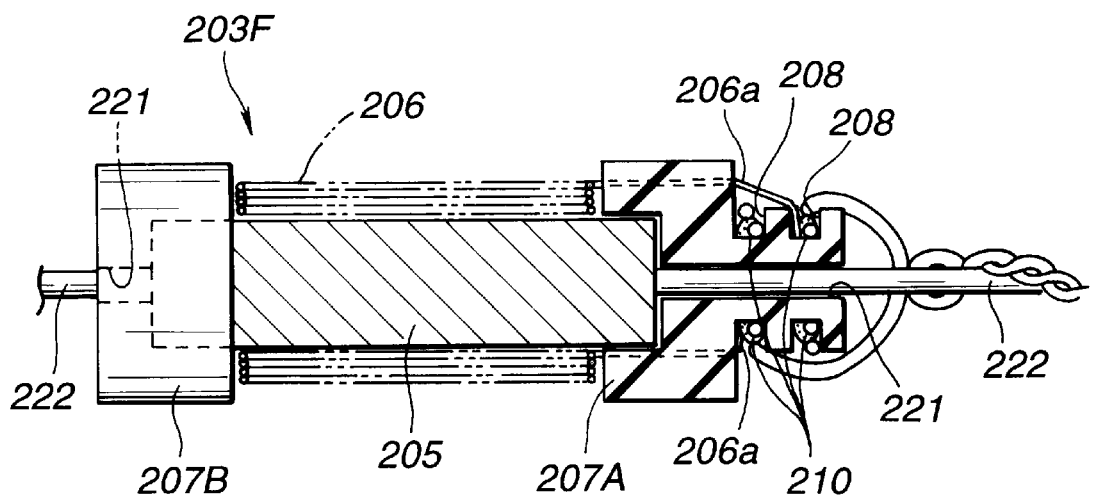

FIG. 63 gives a coil apparatus of the seventh embodiment.

Figure 64:
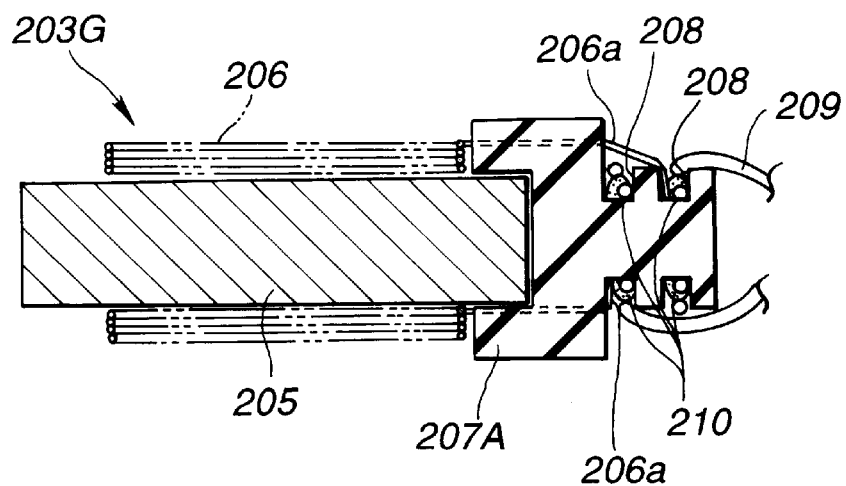
Figure 65:
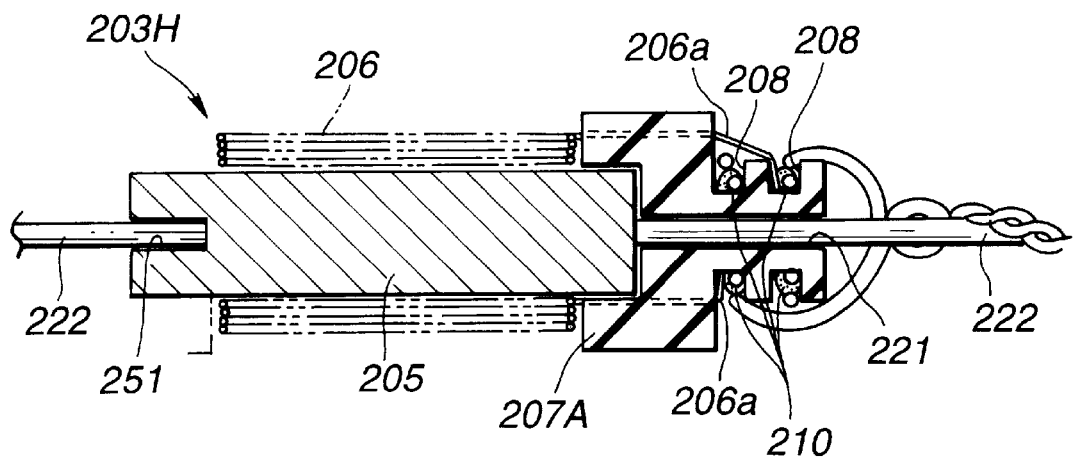

FIGS. 64 and 65 give a coil apparatus of the eighth embodiment: FIG. 65 gives a modified version of the apparatus of FIG. 64.

Figure 66:
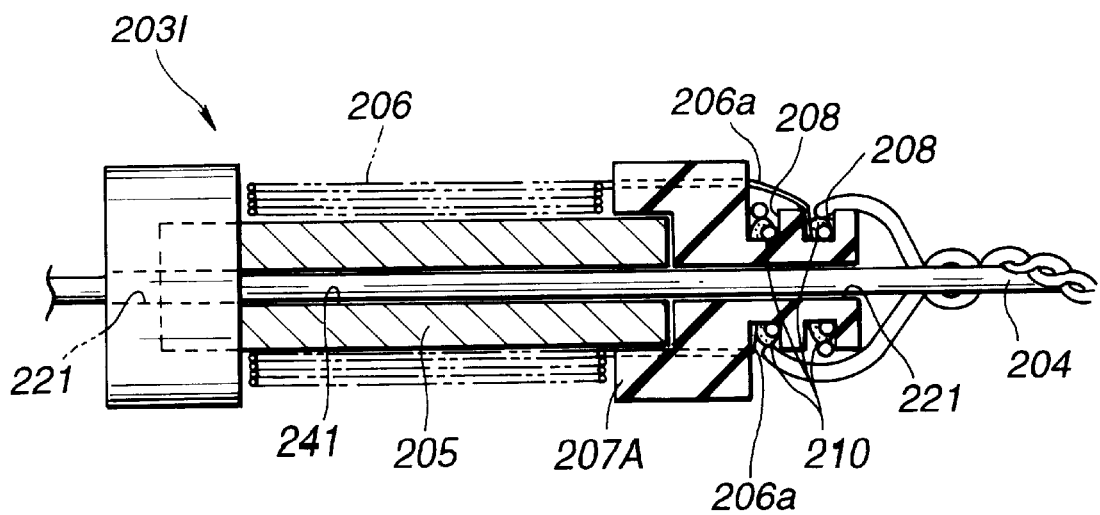
Figure 67:
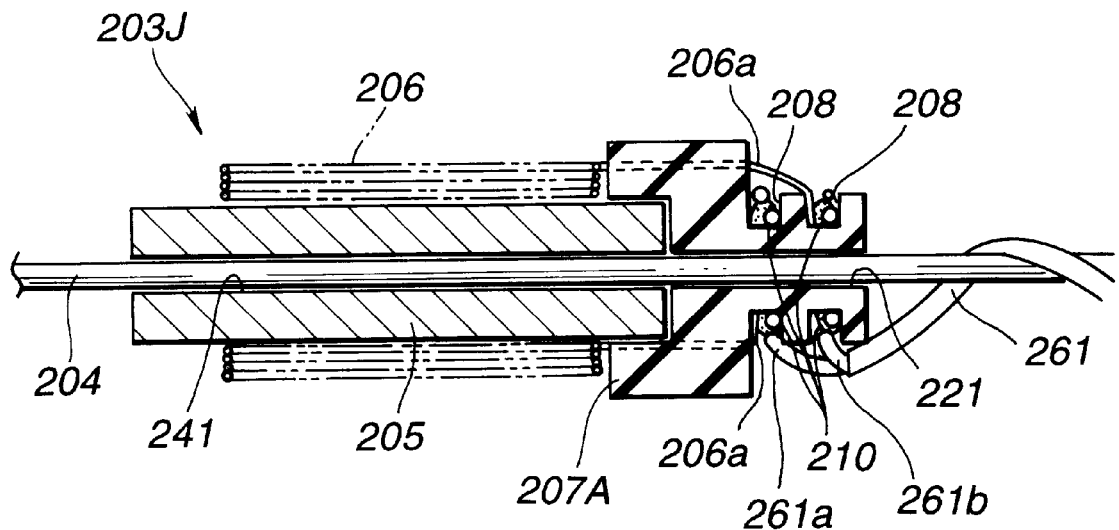

FIGS. 66 and 67 give coil apparatuses of the ninth embodiment: FIG. 67 gives a modified version of the apparatus of FIG. 66.

Figure 68:
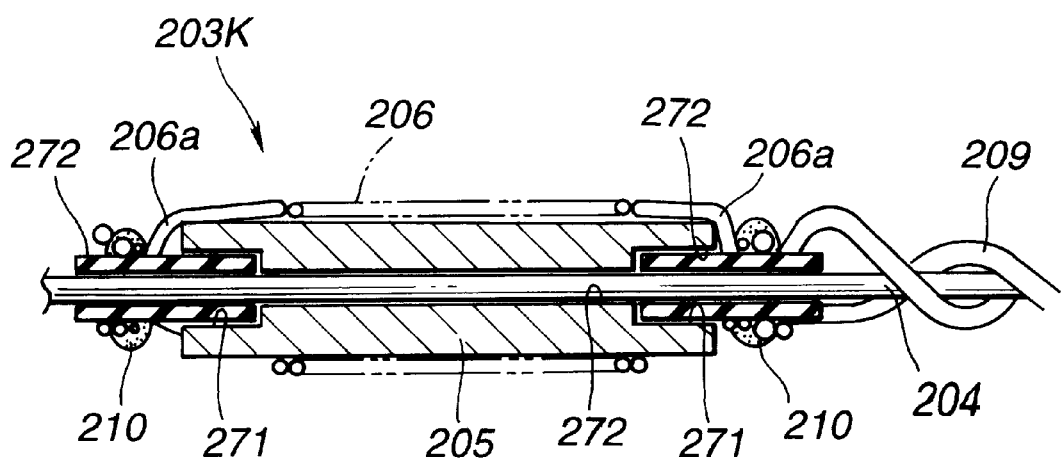
Figure 69:
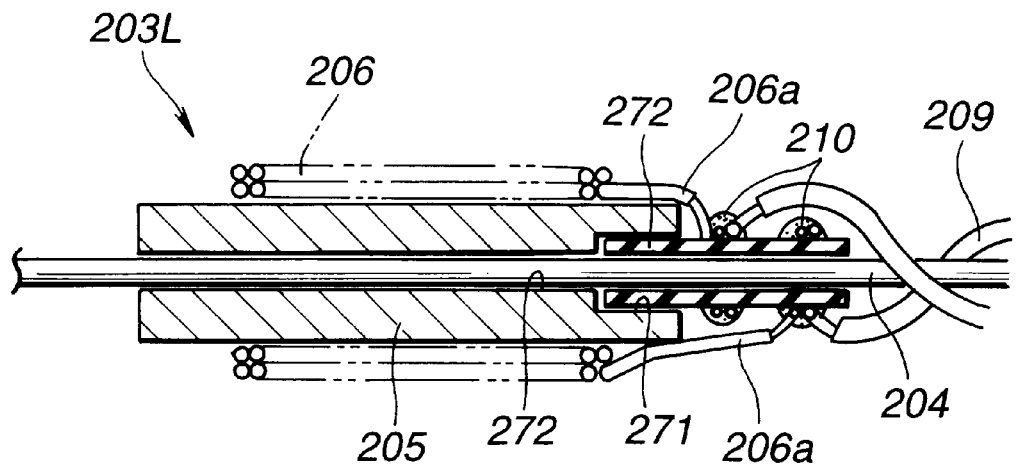

FIG. 68 gives a coil apparatus of the tenth embodiment, and FIG. 69 gives a modified version of the apparatus of FIG. 68.

Figure 70:
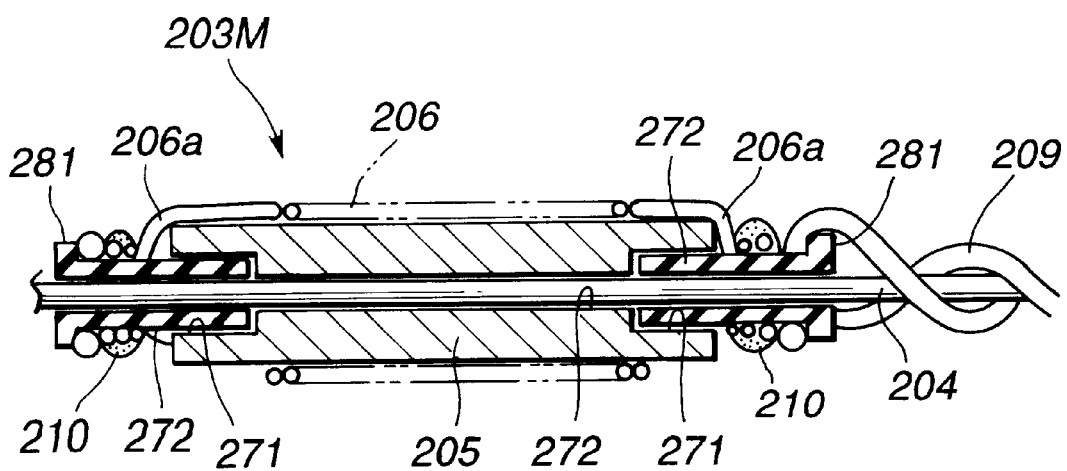

FIG. 70 gives a coil apparatus of the eleventh embodiment.

Figure 71:
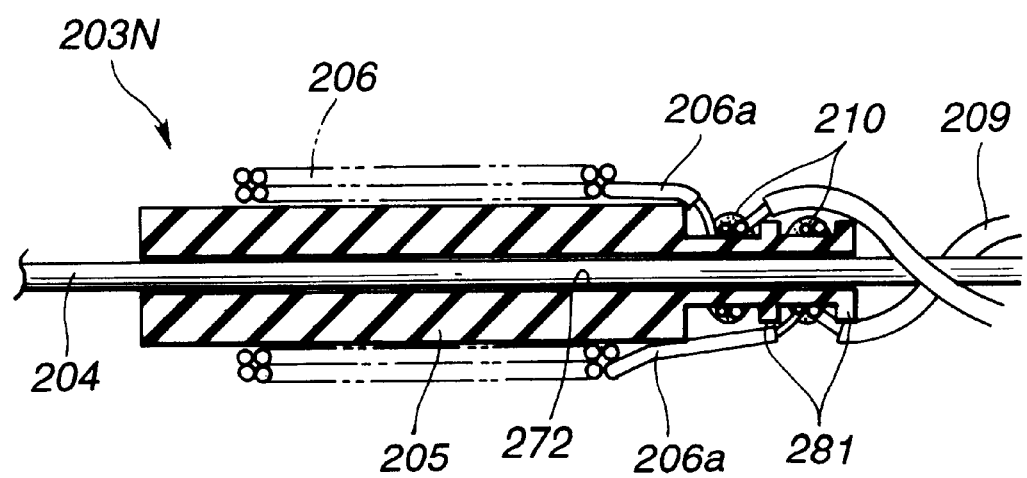

FIG. 71 gives a coil apparatus of the twelfth embodiment.

DETAILED DESCRIPTION OF THE PREFERRED EMBODIMENTS

First Embodiment (Constitution)

Figure 1:
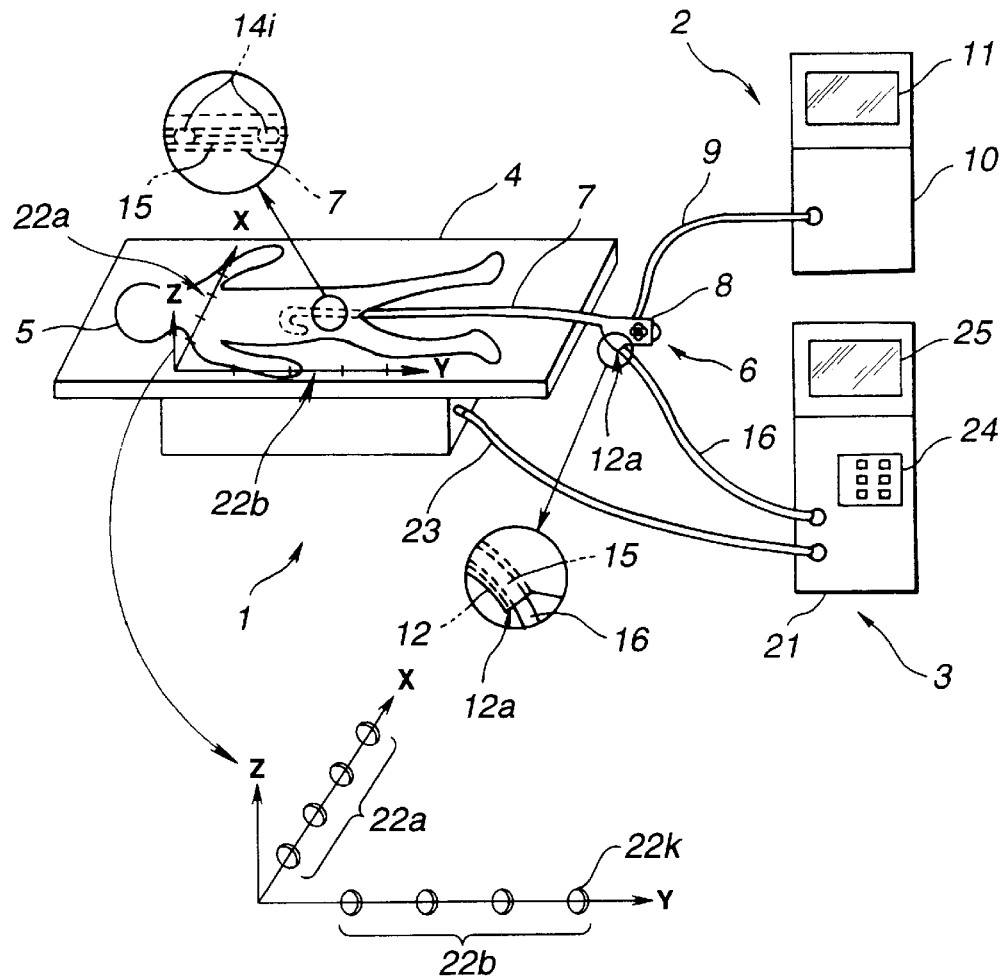
FIGS. 1–39 is related with the first embodiment of this invention.

As shown in FIG. 1, the endoscope system 1 of the first embodiment consists of an endoscopy monitor 2 to serve for endoscopic observation and an endoscope shape reconstructing apparatus 3 to support endoscopy. The endoscope shape reconstructing apparatus 3 assists endoscopic observation which takes place after the probe 7 of electronic endoscope 6 has been inserted into a bodily cavity of a patient lying on the bed 4.

The electronic endoscope 6 has a following constitution: to the proximal end of a slender, flexible insert 7 is connected a handle 8 with a curved operation knob; and from the handle 8 extends a universal cord 9 which is then connected to a videomaking system (or videoprocessor) 10.

Through this electronic endoscope 6 passes a light guide which receives light from a light source in the videoprocessor 10 and transmits it through a window (illumination window) prepared on the tip of insert 7 to shed it on an object of interest in the patient's body. The light reflecting from the object of interest thus illuminated passes through an object lens mounted on an observation window placed close to the illumination window, and focuses its image on a photographic element which has been placed in the focusing plane. The photographic element capable of photoelectric conversion turns the image into electric signals.

The electric signals thus converted are processed by a video-signal processing section of the videoprocessor 10, to be translated into standard image signals which are displayed on a visual monitor 11 connected to the videoprocessor 10.

The electronic endoscope 6 has, in addition, a channel 12 for forceps insertion, and from the opening 12a leading to the forceps channel 12, an array of, say, 16 magnetism generating elements (14a, 14b, . . . , and 14p, or, as a whole, to be represented by 14i hereinafter) or a probe 15 is inserted through the channel 12. Now, the insert has an array of source coils ready for operation.

From the proximal end of the probe 15 extends a source cable 16 whose proximal end is reversibly connected to the body 21 of endoscope shape reconstructing apparatus 3. The body 21 works as a radiofrequency signal provider, and provides radiofrequency signals (driving signals) through the source cable to the source coils 14i or a magnetism generating means. Receiving the radiofrequency signal, the source coil 14i radiates an electromagnetic wave accompanied with a magnetic field.

Onto the bed 4 where a patient 5 lies, is mounted a combination of sets of magnetism detecting elements (or sensor coils) each comprising at least four single core coils 22k which are arranged such that they stand, having a common center, on the same line facing the same direction. For example, two sets of sensor coils 22a and 22b (to be represented by 22j hereinafter) crossing each other at right angles are combined to give one version of sensor coil unit. In this case single core coils are eight in total.

The sensor coil unit 22j is connected through a connector attached to the bed 4 via a sensor cable 23 working as an element of sensor signal transmitting means, to the body 21. The body 21 has a control panel 24 through which the operator can control the apparatus, or a keyboard or the like. Further, to the body 21 is connected a monitor 25 which acts as a displaying means of the image of endoscope shape under study.

Figure 2:
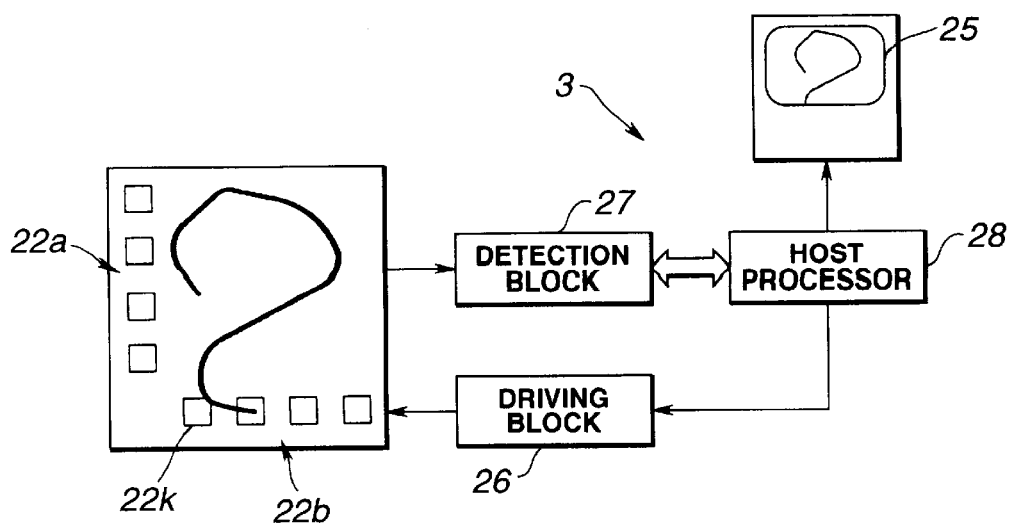

The endoscope shape reconstructing apparatus 3 will be detailed further below. The endoscope shape reconstructing apparatus 3 is constituted of, as shown in FIG. 2, a driving block 26 to excite the source coil 14i, a detection block 27 to analyze signals received by the sensor coil unit 22j, and a host processor 28 to integrate the signals analyzed by the detection block 27.

Figure 3:
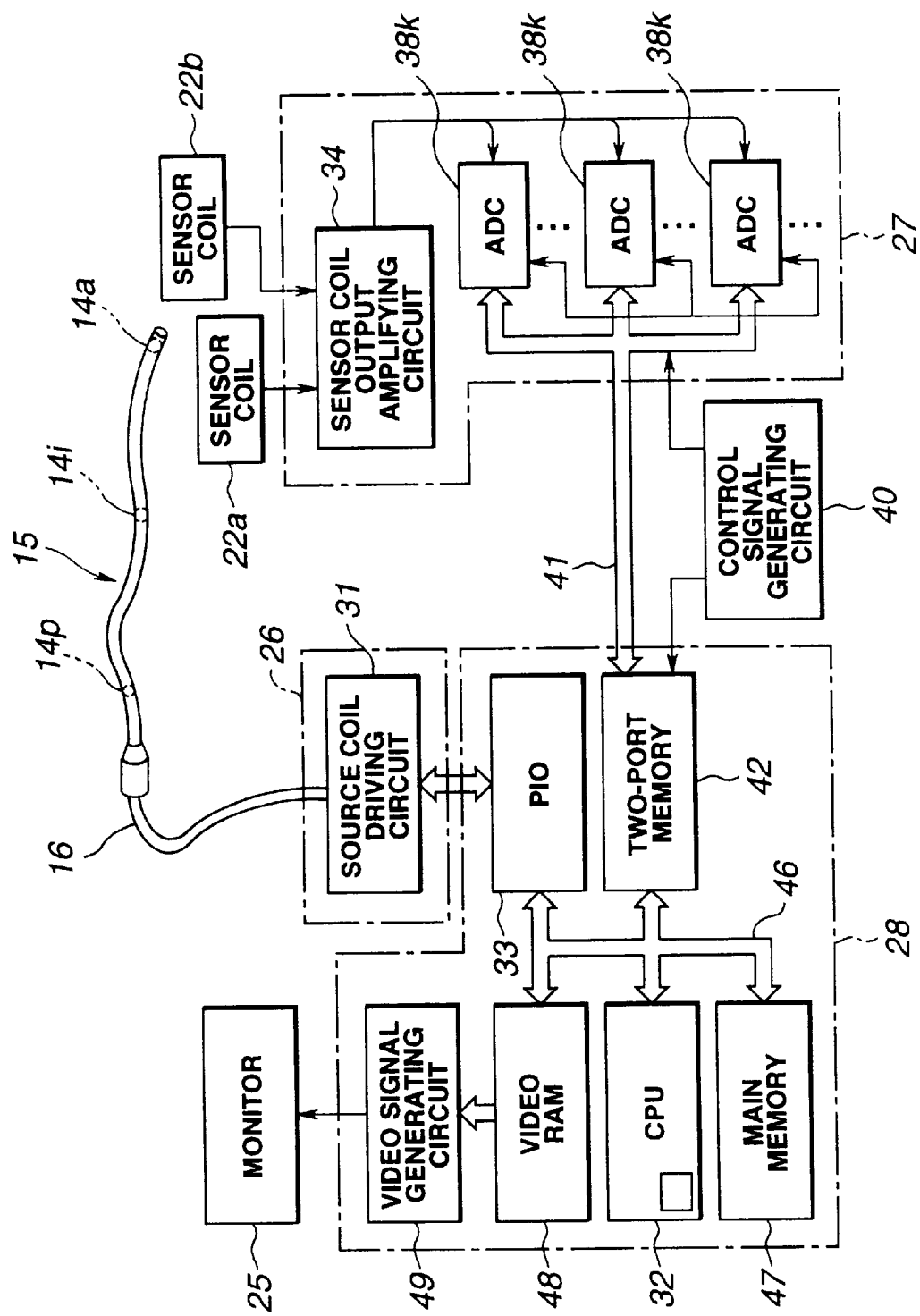

As shown in FIG. 3, the probe 15 inserted through the insert 7 of electronic endoscope 6 comprises, as described earlier, an array of 16 source coils 14i which are arranged with a specified distance between adjacent coils, and these source coils 14i are separately connected to a source coil driving circuit 31 which give rise to 16 different driving signals of radiofrequencies.

The source coil driving circuit 31 drives separately individual source coils 14i through sinusoidal currents of different frequencies. The frequency of individual driving currents dispatched from the source coil driving circuit 31 is determined on the basis of data (data of driving frequency) stored in a driving frequency setting data storing means which is not illustrated in the accompanied figures, or by a driving frequency setting data memorizing means. The data of driving frequency is transmitted through PIO (parallel input/output circuit) 33 to a driving frequency data storing means (not illustrated here) within the source coil driving circuit 31 and stored there under the control of CPU (central processing unit).

On the other hand, eight single core coils or two sensor coil sets constituting a sensor coil unit 22j are connected to a sensor coil signal amplifying circuit 34 which forms an element of the detection block 27.

Figure 4:
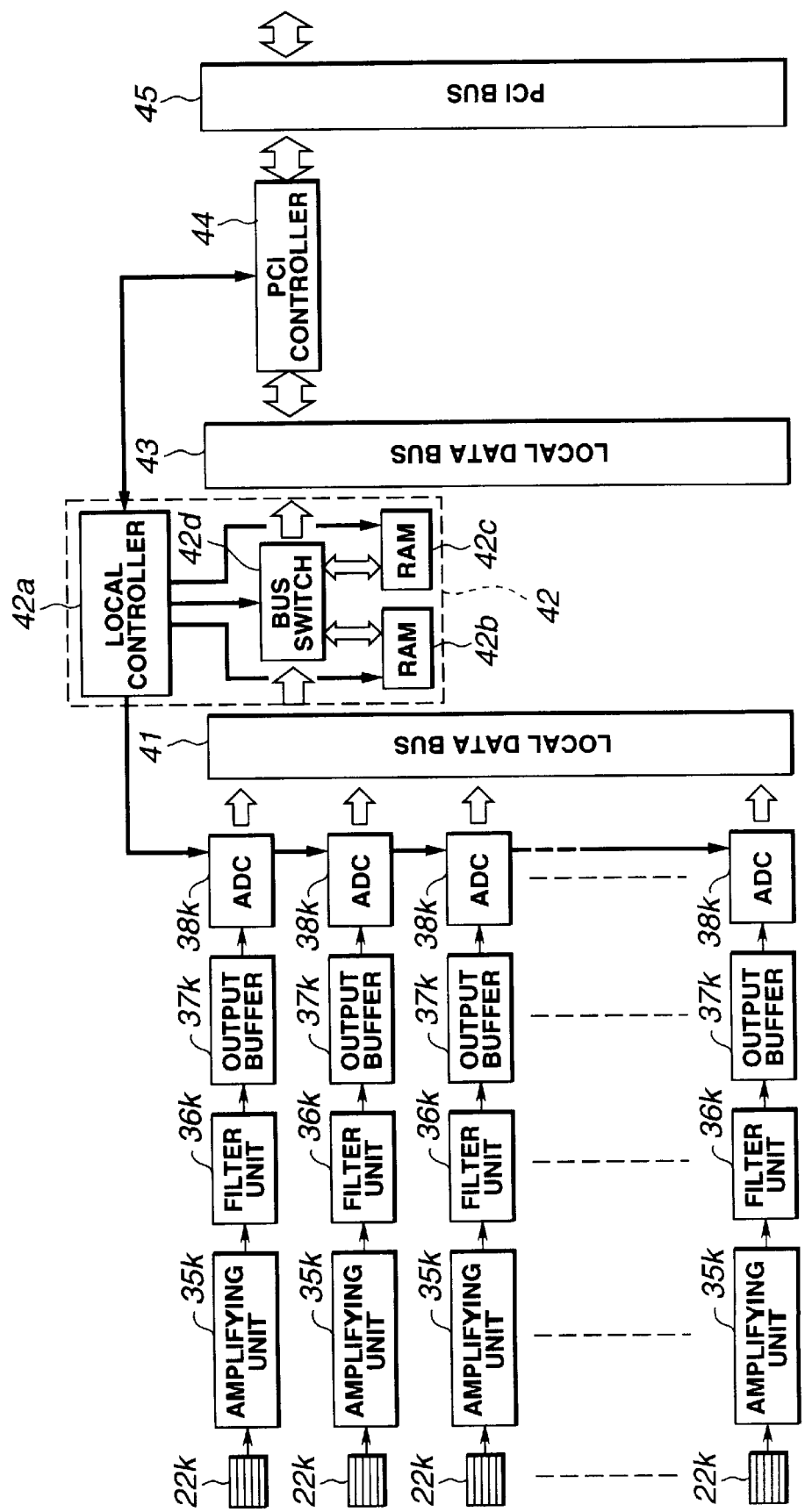

As seen from FIG. 4, in the sensor coil signal amplifying circuit 34, each single core coil 22k is connected to a corresponding amplifier unit 35k. A minute signal picked up by each single core coil 22k is fed to a corresponding amplifying unit 35k to be amplified, and sent to a filter unit 36k with bands allowing the passage of frequencies with which the magnetic fields from individual source coils oscillate, to eliminate unnecessary frequency components. The resulting output is sent to an ADC (analog/digital converter) unit 38k and is turned there into digital signals so as to be read by the host processor 28.

The detection block 27 is constituted of a sensor coil signal amplifying circuit 34 and ADCs 38$k$, and the sensor coil signal amplifying circuit is further constituted of amplifying units 35$k$, filters 36$k$ and output buffers 37$k$.

Let's return to FIG. 3. Eight different outputs from the sensor coil signal amplifying circuit 34 are transmitted to eight corresponding ADCs 38$k$ where the signals are converted to digital signals with a specified sampling interval, complying with timing pulses from a control signal generating circuit 40. These digital data are written through a local data bus 41 into a two-port memory 42, being controlled by the control signals from the control signal generating circuit 27.

Figure 5:
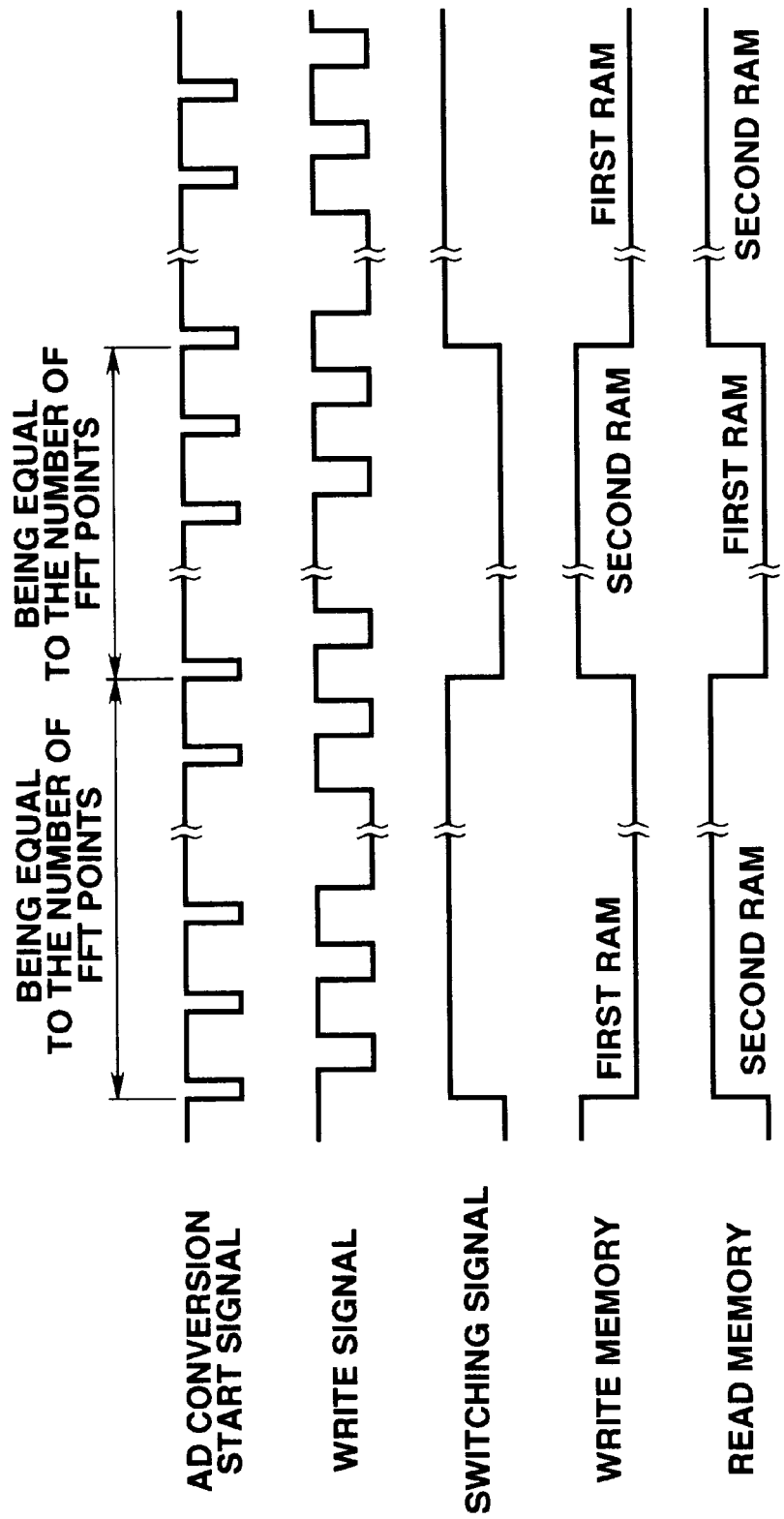

The two-port memory 42, as shown in FIG. 4, is constituted functionally of a local controller 42$a$, first RAM 42$b$, second RAM 42$c$ and bus switch 42$d$. As seen from the timing chart as indicated in FIG. 5, in response to A/D conversion start signals from the local controller 42$a$, ADC 38$k$ starts A/D conversion, and the bus switch 42$d$ switches on and off between RAMs 42$b$ and 42$c$ through switching signals from the local controller 42$a$, and uses the first and second RAMs 42$b$ and 42$c$ alternately as read-out and write-on memories. When the system is switched on, write signals are dispatched to make the RAMs ready to receive data.

Let's return to FIG. 3 again. A CPU 32, in response to control signals from the control signal generating circuit 27, read digital data stored in the two-port memory 42 through an internal bus 46 consisting of the local data bus 43, PCI controller 44 and PCI bus (see FIG. 4), and, as will be described later, applies a frequency extraction processing (Fourier transformation, FFT) to the digital data, utilizing a main memory 47, thereby separating the frequency components corresponding to the frequencies of driving currents of individual source coils 14$i$, or the frequency components carrying information regarding the magnetic fields of individual source coils 14$i$. The thus separated digital data regarding magnetic fields of individual source coils are utilized to determine the coordinates of individual source coils 14$i$ placed in the insert 7 of an endoscope 6.

The system estimates from the thus obtained coordinate data how the insert 7 of an electronic endoscope currently stays in the body, reconstructs the image of the endoscope shape, and gives the image data to a video RAM 48. The image data written in the video RAM is read out by a video signal generating circuit 49, and converted to analog video signals which are then sent to a monitor 25. The monitor 25, receiving the analog video signals, reproduces on the screen how the insert 7 of electronic endoscope is inserted into the body.

The CPU 32 calculates the electromotive forces (amplitude of sinusoidal waves) induced in a sensor coil set 22$j$ comprising four sensor coils 22$k$, and phase data, or the data from which the magnetic field information of individual source coils can be obtained. The phase data are related with the polarity ± of electromotive forces.
(Operation)

Figure 6:
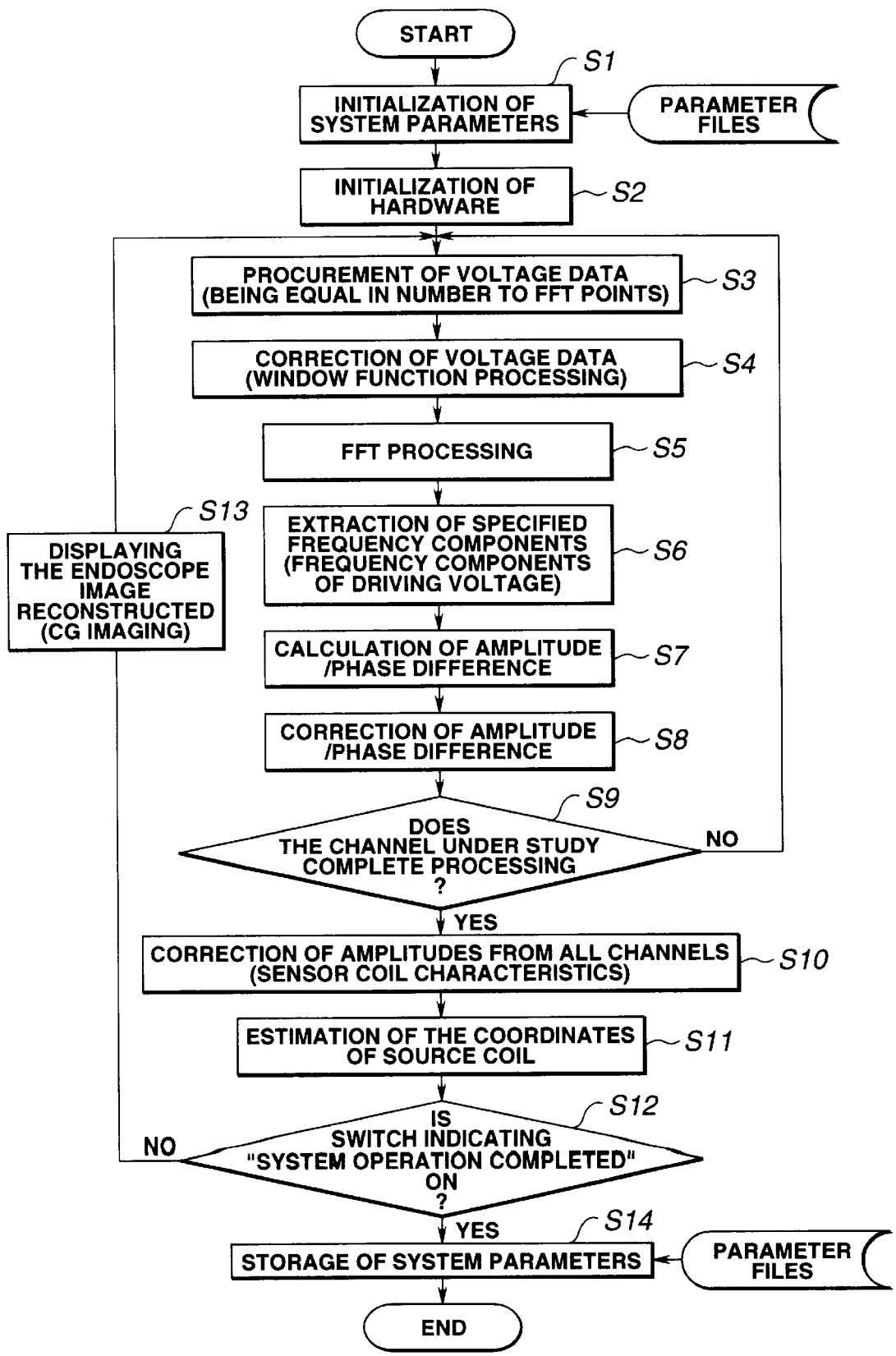

The endoscope system 1 in this embodiment, when power is switched on, as shown in FIG. 6, initializes individual system parameters by referring data in parameter files at step S1, and then initializes hardware at step S2.

After power has been switched on, data corresponding to FFT points are always renewed in the two-port memory 42 to be ready for FFT processing (see FIG. 5). At step S3, CPU 32 receives data corresponding in number to FFT points. At step S4, CPU 32 corrects the data by a window function method, and performs at S5 the FFT processing described later. After completing FFT processing, CPU extracts frequency components corresponding to those of driving currents at step S8, calculates the amplitude and phase differences of each frequency component at step S7 and corrects the amplitude and phase differences at step S8.

CPU checks whether processing of all signals from the eight ADCs 38$k$ (a series of elements responsible for the processing of signals from a given sensor coil will be referred to generally as "channel" and data obtained through a channel as "channel data", hereinafter) is completed or not, and, when it finds that it is not completed yet, returns to step S3, and, when it finds it is completed, it advances to step S10. Thus, at step S10, CPU corrects the amplitudes of all signals according to the individual characteristics of sensor coils, and calculates the coordinates of individual source coils 14$i$ based on the amplitude and phase difference data by a method described later.

Later, at step 12, CPU checks whether a system-off switch which indicates that the endoscope system 1 is inactivated is turned on or not. When it finds it is not switched on, it initiates at step S13 an endoscope image reconstructing process described later, returns to step S3, and repeats the same processes. When CPU finds the system-off switch has been turned on at step 12, it stores system parameters into parameter files at step S14 and completes operation.

Figure 7:
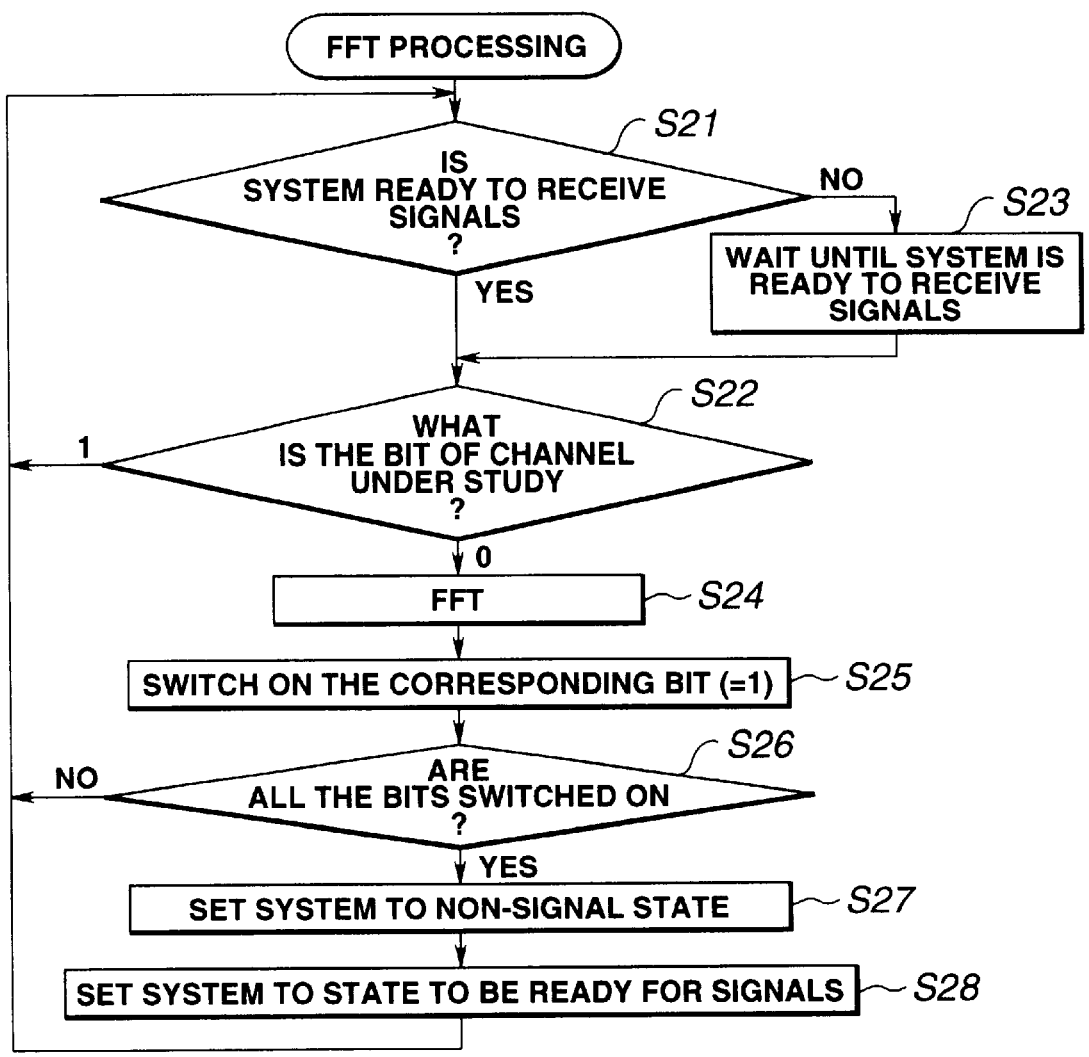

FFT processing at step S5 proceeds as indicated in FIG. 7. CPU 32 checks at step 21 whether all the channels are ready to process signals (whether data that correspond in number to FFT points are provided to the channels) (alert state), and, when it finds all the channels alert, it advances to step S22. When it finds all channels are not alert, it waits at step S23 until all the channels become alert. After having found that all the channels are ready to process signals, it advances to step 22.

At step S22, CPU checks the bit state of channel data before it submits the data to FFT processing: when it finds the data bit is 0, the data under study are raw or unprocessed; and when it finds the data bit as 1, the data in question has already received FFT processing. When it finds the data bit as 0, it advances to step S24 where it submits the data to FFT processing, and, after confirming the completion of FFT processing, converts the bit sate from 0 to 1 at step 25. When CPU finds the data bit as 1 at step 22, it returns to step S21, and repeats the same processes for the next channel data until all channel data have received FFT processing.

At step S26 following step S25, CPU checks whether the bit states of all channel data are 1 or not, and, when it finds there are one or more bit states other than 1, it returns to step 21 where it instructs the relevant channels to submit the data whose bit state is not 1 to FFT processing. When CPU confirms that the bit states of channel data in question are all 1 at step S26, it advances to step S27 where it puts all channels into non-alert state and keeps them at this state until a set of data sufficient in number to correspond to FFT points are collected in all channels. After confirming that a set of data sufficient in number to correspond to FFT points are collected in all channels, CPU advances to step S28 where it puts all channels into alert state, and returns to step S21.

Figure 8:
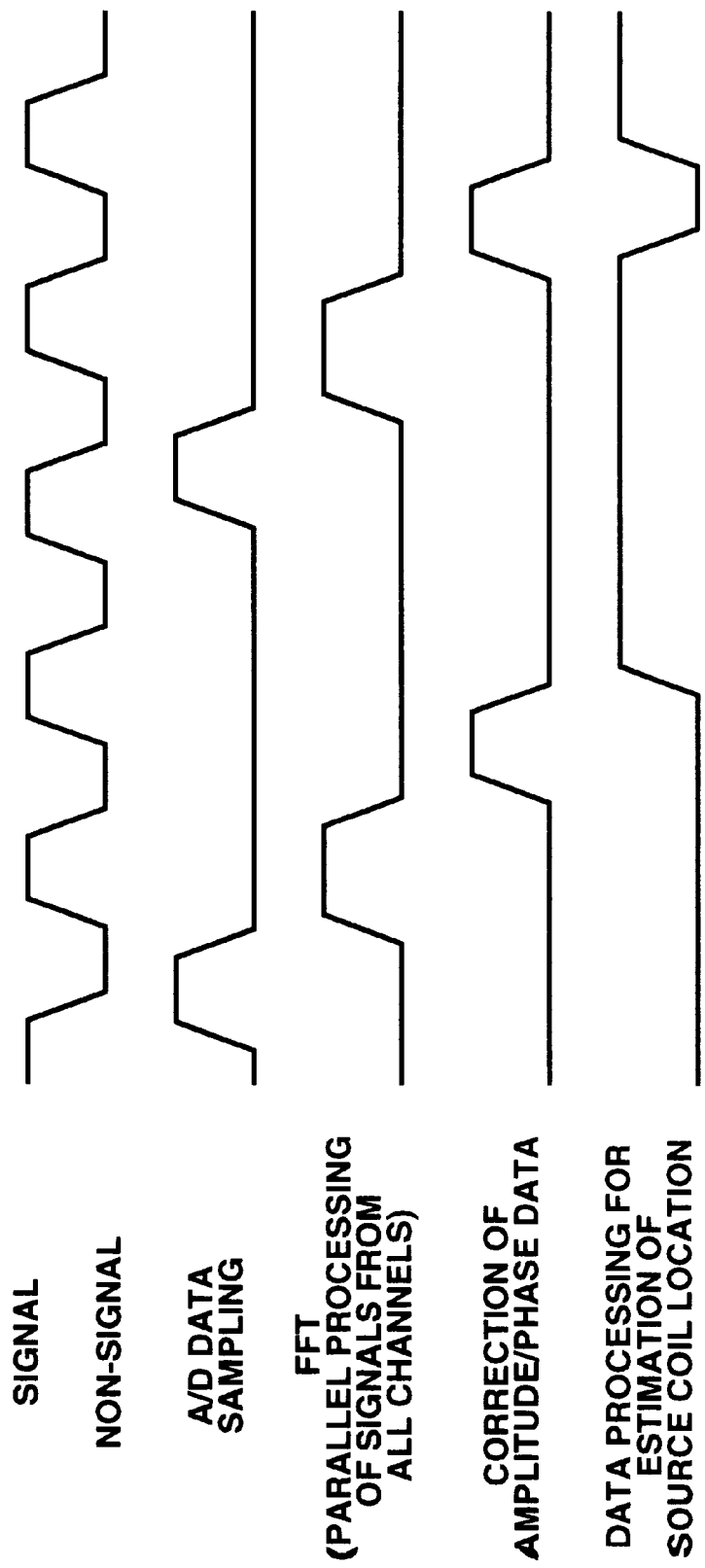

The processing depicted in FIG. 6 occurs as a parallel processing as indicated in FIG. 8 to achieve the processing in a shorter time. This mode of processing is particularly useful for FFT processing which requires repetitive calculations each of which needs a considerable time. Thus, FFT processing proceeds as simultaneous, parallel processing of individual constituent data units. Furthermore, CPU effectively assigns necessary calculation works for FFT processing to processors relieved of works, to make the most economical use of time and to increase the processing speed.

As described earlier, CPU performs a frequency component extraction processing based on Fourier transformation. In this processing, a problem called leakage might arise if there were a discrepancy between the frequency $f_i$ of the sinusoidal current driving a source coil 14i and the filtration band edges inherent to the corresponding digital data.

If the filtration width of digital data sampled (corresponding to the length of sampled signal trains) includes multiples of all the frequencies $f_i$ of driving currents, the data will allow precise determination of the amplitudes and phases (so-called amplitude and phase spectra) of all sinusoidal waves with different frequencies included in the original driving currents. If, however, the filtration width is not a multiple of any one of driving frequencies $f_i$, leakage occurs for the wave of that frequency, which would give a wrong amplitude and phase in regard to that wave. To meet this problem, generally a window function method incorporating a Hamming window has been employed (see Brigham, E. O., "The Fast Fourier Transformation", Sec. 6).

The window function method mentioned above, however, only alleviates the error caused by leakage and will not eliminate it. The method also recommends the use of driving currents with specific frequencies to minimize the misleading effect from leakage, which may restrict the use of the present system.

A frequency component extraction processing employed in this embodiment in step S6 of FIG. 6 will be described below. This treatment positively corrects the error caused by leakage through the use of simplified matrix calculation, to obtain more exact data on the amplitude and phase of a wave of interest.

For brevity, let's assume that the data after Fourier transformation have been normalized and guaranteed to be a multiple of a window function (rectangular window).

A train of signals comprising sinusoidal waves whose frequency is $f_k$ is submitted to Fourier transformation (here complex, discrete Fourier transformation is applied) to give $F_k$ which is expressed by the equation, $$F_k = \sum_{n=0}^{N-1} f_n e^{\frac{-j2\pi kn}{N}} \qquad (1)$$

where N represents the length of discrete trains of signals sampled, and j imaginary unit. $F_k$ consists of the real number portion $Re\{F_k\}$ and imaginary number portion $Im\{F_k\}$.

When the filtration width of digital data is a multiple of the frequency $f_i$ of a corresponding driving wave, the frequency $fs_i$ derived through discrete Fourier transformation is equal to the frequency $f_i$ of the driving wave. If the above condition is not met, the observed frequency $fs_i$ will give a more or less error regarding the true driving frequency $f_i$ (the frequency $fs_i$ does not give the true driving frequency $f_i$). If all observed frequencies $fs_i$ give true driving frequencies $f_i$, the filtration width will be a multiple of all the driving frequencies $f_i$, and no leakage will result.

Here we will describe the method by which to find $f_i$, or the result a driving frequency $f_i$ will give after it has undergone Fourier transformation $F_i$: the method consists of obtaining $f_i$ from $Fs_i$ or the Fourier transform of an observed wave with a frequency of $fs_i$.

When a sampled train of signals to give digital data is composed of sinusoidal waves M in number corresponding to driving frequencies $f_i$ (i=1, 2, ..., M), the Fourier transform of an observed frequency $fs_i$ has a relation with the Fourier transform of a driving frequency $f_i$ as is expressed by the following equation, $$\begin{bmatrix} Re\{Fs_1\} \\ Im\{Fs_1\} \\ Re\{Fs_2\} \\ Im\{Fs_2\} \\ \\ Re\{Fs_M\} \\ Im\{Fs_M\} \end{bmatrix} = A \cdot \begin{bmatrix} Re\{F_1\} \\ Im\{F_1\} \\ Re\{F_2\} \\ Im\{F_2\} \\ \\ Re\{F_M\} \\ Im\{F_M\} \end{bmatrix} \qquad (2)$$

where A represents a matrix with a dimension of 2M×2M which comprises a factor sequence defining leaks among $Re\{F_1\}, Im\{F_1\}$ to $Re\{F_M\}, Im\{F_M\}$.

Here the equation (2) is expressed alternatively as $$Y = A \cdot X \qquad (3)$$

In the equation (3), X and Y represent respectively matrices with a dimension of 2M×1 which include the real and imaginary portions of Fourier transforms of driving frequencies $f_i$ and observed frequencies $fs_i$ (i=1, 2, ..., M).

Assume, as an example, a matrix X to be expressed as $$X = X_1 = [1, 0, 0, \ldots 0, 0, 0]^t \qquad (4)$$

where t represents inversion. This matrix means that a train of signals is composed of a sine wave with a driving frequency of $f_1$ and its phase being shifted by $\pi/2$, or of a cosine wave with a frequency of $f_1$.

Or, take, as an example, another matrix X to be expressed as $$X = X_2 = [0, 1, 0, 0, \ldots, 0, 0, 0]^t \qquad (5)$$

This matrix derives from a train of signals which is composed only of a sine wave with a driving frequency of $f_1$ and phase of 0.

Similarly, $$X = X_3 = [0, 0, 1, 0, \ldots, 0, 0, 0]^t,$$

$$X = X_4 = [0, 0, 0, 1, \ldots, 0, 0, 0]^t,$$

$$\vdots$$

$$X = X_{2M-1} = [0, 0, 0, 0, \ldots, 0, 1, 0]^t$$

$$X = X_{2M}[0, 0, 0, 0, \ldots, 0, 0, 1]^t \ldots \qquad (6)$$

The trains of signals represented by the above equations represent sine waves with driving frequencies $f_i$ (i=2, 3, ..., M) and phase shift being 0 or $\rho/2$, having amplitudes equal to unit.

The matrices $X_1, X_2, \ldots, X_{2M}$ are put into the equation (3), and Y matrices derived therefrom are defined as $Y_1, Y_2, \ldots, Y_{2M}$. The matrices $Y_1, \ldots, Y_{2M}$ are observed values including leakage (which is expressed as numbers other than 0 at places which otherwise 0 should occupy, or numbers other than 1 at places which otherwise 1 should occupy) derived from the digital data which, if free from leakage, would give the matrices $X_1, \ldots, X_{2M}$. As the matrices $Y = Y_1, Y_2, \ldots, Y_{2M}$ are terms forming each separate row of the matrix A, they can be expressed as $$A = [Y_1, Y_2, Y_3, \ldots, Y_{2M}] \qquad (7).$$

In summing up, the Fourier transform $F_i$ of a driving wave with a frequency $f_i$ (Fourier transformation is principally frequency analysis of a given wave into amplitude and phase data of individual frequency components of that wave), gives a matrix X which can be expressed as $$X = A^{-1} \cdot Y \qquad (8)$$

Namely, X can be obtained after the matrix Y or the Fourier transform $Fs_i$ of observed frequency $fs_i$ is multiplied by the reciprocal matrix of A or $A^{-1}$. The matrix A can be derived, as described earlier, from the matrix $Y=Y_1, Y_2, Y_3, \ldots Y_{2M}$ or the matrix of signal trains which, if free from leakage, would give $X=X_1, X_2, X_3, \ldots, X_{2M}$.

Thus, as a preliminary step, the matrix A, and then its reciprocal $A^{-1}$ is calculated. Then, it is applied to the matrix Y which is derived from signal trains through Fourier transformation, for multiplication, to give a more precise substitute of X. This maneuver allows a more precise estimation of the location of source coils 14i.

Further, it is possible to determine the matrix X in a faster, simplified manner by preparing a matrix Q with a dimension of 2M×N which can be simultaneously subject to Fourier transformation and multiplication by the matrix $A^{-1}$, and this is achieved by directly applying the matrix Q to digital data with a length of N×1 for multiplication.

This maneuver available to the present endoscope shape reconstructing apparatus allows one to have a more precise estimation regarding the location of source coils and to have a freer selection of their driving frequencies.

Then, an estimating process of determining the coordinates of source coils performed at step S11 of FIG. 6 will be detailed below. The estimating process of determining the coordinates of source coils will be given first, and then its application to concrete examples will be outlined next.

Figure 9:
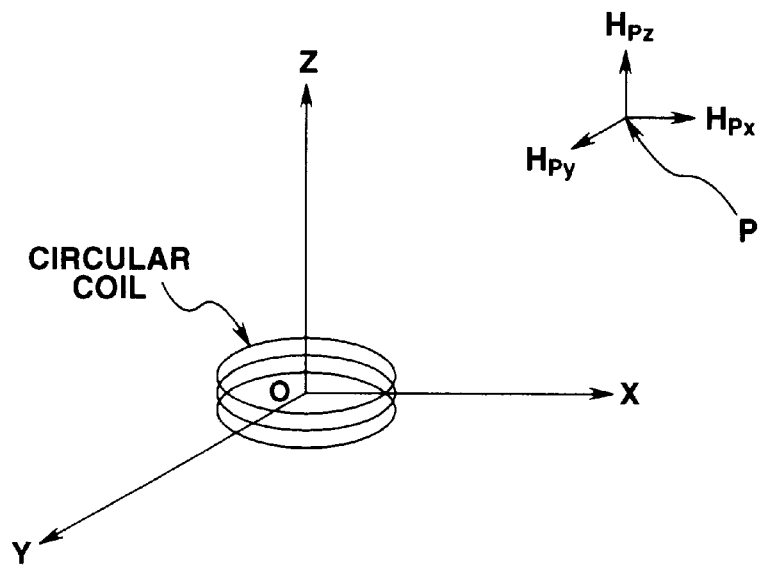

As shown in FIG. 9, a thin, circular coil with a very small diameter, as discussed in Japanese Unexamined Patent Publication No. 9-84745, behaves like a magnetic dipole when current passes through it. Thus, it gives rise to a magnetic potential around a point P in a 3D space which can be expressed by $$U_P = \frac{\mu I N_1 \pi a^2}{4\pi\mu} \frac{z}{(x^2+y^2+z^2)^{\frac{3}{2}}} \qquad (9)$$

where $\mu$ represents magnetic permeability, $N_1$, turns of the circular coil, a, radius of the circular coil, and I, current passing through the circular coil. Accordingly, the magnetic field ($H_{px}$, $H_{py}$, $H_{pz}$) around the point P along the axes in parallel to X-, Y- and Z-axes can be given by $$H_{Px} = -\frac{\partial U_P}{\partial x} = \frac{IN_1 a^2}{4} \frac{3xz}{(x^2+y^2+z^2)^{\frac{5}{2}}} = k_g \frac{3xz}{r^5} \qquad (10)$$

$$H_{Py} = -\frac{\partial U_P}{\partial y} = \frac{IN_1 a^2}{4} \frac{3yz}{(x^2+y^2+z^2)^{\frac{5}{2}}} = k_g \frac{3yz}{r^5}$$

$$H_{Pz} = -\frac{\partial U_P}{\partial z} = \frac{IN_1 a^2}{4} \frac{2z^2-x^2-y^2}{(x^2+y^2+z^2)^{\frac{5}{2}}} = k_g \frac{2z^2-x^2-y^2}{r^5}$$

Figure 10:
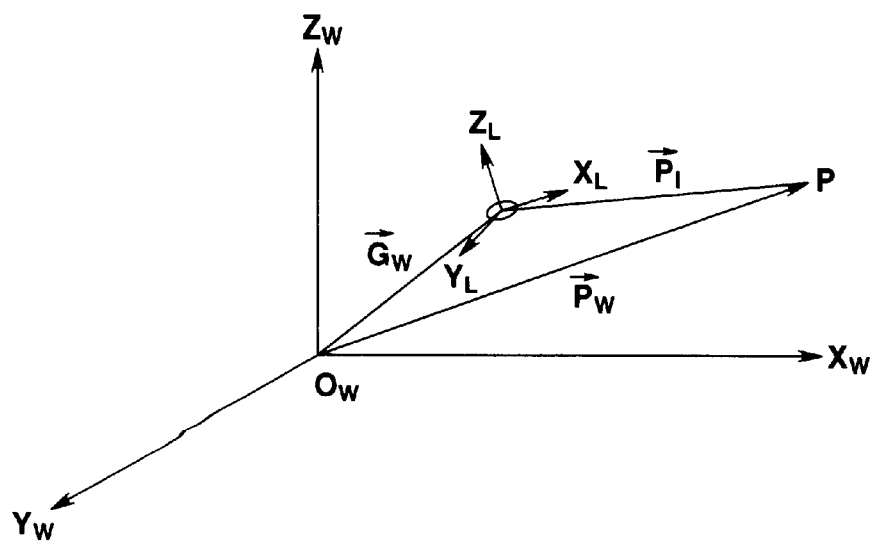

As shown in FIG. 10, when a single core coil $C_g$ (or source coil hereinafter) to generate a magnetic field is placed at a point ($X_{gw}$, $Y_{gw}$, $Z_{gw}$) in a 3D space (or world coordinate system $X_w$-$Y_w$-$Z_w$ hereinafter), what concerns us here at first is to find what magnetic field is induced around a point P ($X_{pw}$, $Y_{pw}$, $Z_{pw}$).

Let's assume a local coordinate system ($X_L$-$Y_L$-$Z_L$) with the source coil at the origin. Then, the coordinates ($X_{P1}$, $Y_{P1}$, $Z_{P1}$) of the point P in the local coordinate system can be expressed as $$P_l = R^{-1}(P_W - G_W) \qquad (11)$$

$$\begin{pmatrix} x_{Pl} \\ y_{Pl} \\ z_{Pl} \end{pmatrix} = \begin{pmatrix} R_{00} & R_{10} & R_{20} \\ R_{01} & R_{11} & R_{21} \\ R_{02} & R_{12} & R_{22} \end{pmatrix} \begin{pmatrix} x_{PW} - x_{gW} \\ y_{PW} - y_{gW} \\ z_{PW} - z_{gW} \end{pmatrix}$$

where:

$P_l$ represents a vector from origin to point P in the local coordinate system;

$P_W$ represents a vector from origin to point P in the world coordinate system;

$G_W$ represents a vector from origin to source coil in the world coordinate system; and R represents a rotation matrix.

Figure 11:
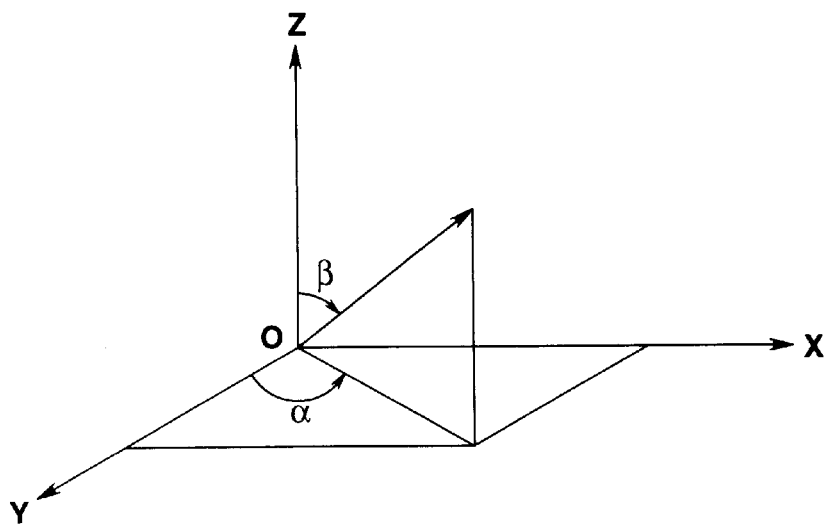

The rotation matrix R, when represented in a polar coordinate as shown in FIG. 11, can be expressed as $$R = \begin{pmatrix} R_{00} & R_{10} & R_{20} \\ R_{01} & R_{11} & R_{21} \\ R_{02} & R_{12} & R_{22} \end{pmatrix} = \begin{pmatrix} \cos\alpha & \sin\alpha\cos\beta & \sin\alpha\sin\beta \\ -\sin\alpha & \cos\alpha\cos\beta & \cos\alpha\sin\beta \\ 0 & -\sin\beta & \cos\beta \end{pmatrix} \qquad (12)$$

where $\alpha$ represents the angle of rotation around $Z_W$-axis, and $\beta$ represents the angle of rotation around $X_W$-axis.

In the local coordinate system with the source coil at origin, the magnetic field $H_l$ induced around the point P ($H_{pxl}$, $H_{pyl}$, $H_{pzl}$) can be expressed from Equation (10) by $$H_{Pxl} = \frac{k_g}{r^5} 3 x_{Pl} z_{Pl} \qquad (13)$$

$$H_{Pyl} = \frac{k_g}{r^5} 3 y_{Pl} z_{Pl}$$

$$H_{Pzl} = \frac{k_g}{r^5} (2z_{Pl}^2 - x_{Pl}^2 - y_{Pl}^2)$$

The same magnetic field $H_W$ ($H_{pxW}$, $H_{pyW}$, $H_{pzW}$) around the point P along the axes in parallel to $X_W$-, $Y_W$-, and $Z_W$-axes with respect to the world coordinate system can be given by $$H_W = R H_l \qquad (14)$$

$$H_{PxW} = \frac{k_g}{r^5} [\{2(x_{PW} - x_{gW})^2 - (y_{PW} - y_{gW})^2 -$$
$$(z_{PW} - z_{gW})^2\} \sin\alpha\cos\beta + 3(y_{PW} - y_{gW})$$
$$(x_{PW} - x_{gW}) \cos\alpha\sin\beta + 3(z_{PW} - z_{gW})$$
$$(x_{PW} - x_{gW})\cos\beta]$$

$$H_{PyW} = \frac{k_g}{r^5} [3(x_{PW} - x_{gW})(y_{PW} - y_{gW})\sin\alpha\cos\beta +$$
$$\{2(y_{PW} - y_{gW})^2 - (z_{PW} - z_{gW})^2 - (x_{PW} - x_{gW})^2\}$$
$$\cos\alpha\sin\beta + 3(z_{PW} - z_{gW})(y_{PW} - y_{gW})\cos\beta]$$

-continued $$H_{PzW} = \frac{k_g}{r^5}[3(x_{PW} - x_{gW})(z_{PW} - z_{gW})\sin\alpha\cos\beta +$$
$$3(y_{PW} - y_{gW})(z_{PW} - z_{gW})\cos\alpha\sin\beta +$$
$$\{2(z_{PW} - z_{gW})^2 - (y_{PW} - y_{gW})^2 -$$
$$(x_{PW} - x_{gW})^2\}\cos\beta]$$

The magnetic field $H_W$ includes two different terms: one term is determined by the location of point P with respect to the source coil in the world coordinate system, and the other is determined by the orientation of source coil.

Figure 12:
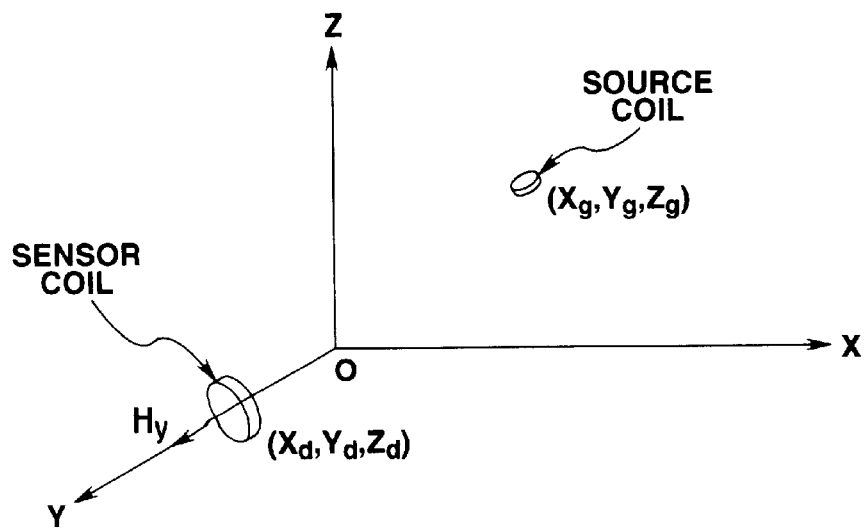

FIG. 12 shows an arrangement of source and sensor coils: a source coil which can generate a magnetic field when electric current is passed therethrough is placed at a point $(X_g, Y_g, Z_g)$ in a 3D space, while a single core coil (or sensor coil hereinafter) facing the same direction with Y-axis is placed at a place $(X_d, Y_d, Z_d)$ on Y-axis. The sensor coil, in response to the magnetic field generated by the source coil, gives rise to a potential which serves as a means to locate the source coil. The magnetic field $H_y$ at the point where the sensor coil exists can be derived from Equation (14) as $$H_y = \frac{k_g}{r^5}[3(x_d - x_g)(y_d - y_g)\sin\alpha\cos\beta + \tag{15}$$
$$\{2(y_d - y_g)^2 - (z_d - z_g)^2 - (x_d - x_g)^2\}\cos\alpha\sin\beta +$$
$$3(z_d - z_g)(y_d - y_g)\cos\beta]$$

The electromotive force $V_y$ induced in the sensor coil by $H_y$ can be obtained by submitting $H_y$ to partial differentiation in terms of time t, and can be expressed as $$V_y = -\mu N_2 \pi b^2 \frac{d}{dt} H_y \tag{16}$$
$$= -\mu N_2 \pi b^2 \frac{\omega I_{max}\cos(\omega t + \varphi)N_1 a^2}{4r^5}[3(x_d - x_g)$$
$$(y_d - y_g)\sin\alpha\cos\beta + \{2(y_d - y_g)^2 - (z_d - z_g)^2 -$$
$$(x_d - x_g)^2\}\cos\alpha\sin\beta + 3(z_d - z_g)(y_d - y_g)\cos\beta]$$
$$= \frac{k_g}{r^5}[3(x_d - x_g)(y_d - y_g)\sin\alpha\cos\beta +$$
$$\{2(y_d - y_g)^2 - (z_d - z_g)^2 - (x_d - x_g)^2\}\cos\alpha\sin\beta +$$
$$3(z_d - z_g)(y_d - y_g)\cos\beta]$$

where:
$N_2$ represents turns of sensor coil; and
$\omega I_{max} \cos(\omega t + \phi)$, electric current passed through the source coil or $I_{max} \sin(\omega t + \phi)$ submitted to differentiation in terms of time t. Thus, the electromotive force Vy can be expressed by five variables ($\alpha$, $\beta$, $X_g$, $Y_g$, $Z_g$).

Figure 13:
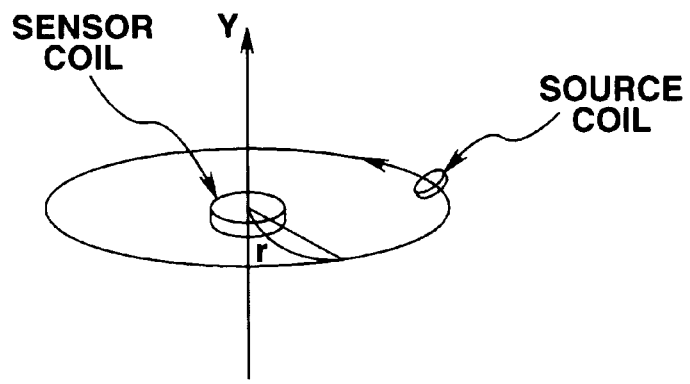

As shown in FIG. 13, when a source coil moves along an orbit which depicts a circle around Y-axis, a constant electromotive force is induced in the sensor coil placed on Y-axis. In this example, however, the sensor coil faces the same direction with respect to Y-axis.

Let's assume in the same situation there are a plurality of sensor coils placed one after another on Y-axis. Each of them will give a circle around Y-axis along which the source coil turns round, or a space where the source coil exists.

Figure 14:
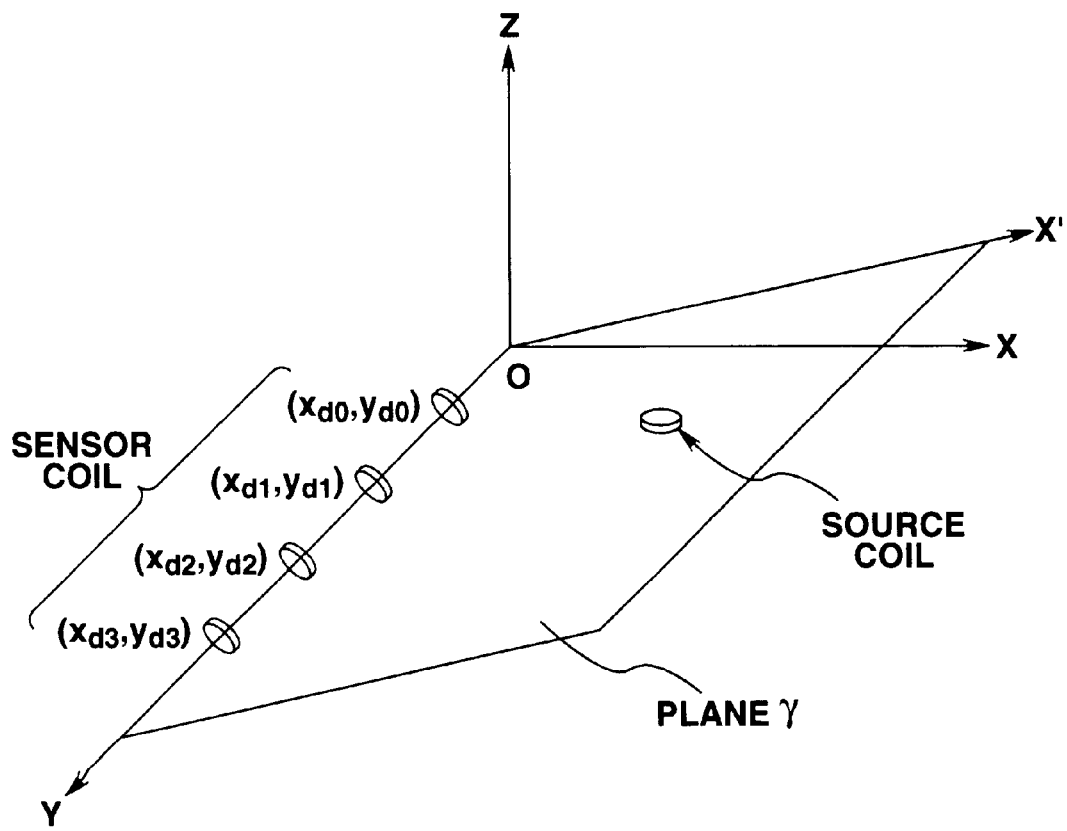

In FIG. 14, four sensor coils are placed one after another on Y-axis, and they determine a plane $\gamma$ between the point of source coil and Y-axis, or a plane coordinate system X'-Y.

In the plane coordinate system X'-Y, the electromotive forces $V_{yi}$ induced in the sensor coils can be expressed by $$V_{yi} = \frac{k_{si}}{r_i^5}[3(x_{di} - x'_g)(y_{di} - y'_g)g_x + \{2(y_{di} - y'_g)^2 - (x_{di} - x'_g)^2\}g_y] \tag{17}$$

where $g_x$ and $g_y$ are terms related with the angle of source coil relative to the plane $\gamma$.

From above it is obvious that estimating of four unknown terms ($g_x$, $g_y$, $X_g'$, $Y_g'$) will give the space occupied by the source coil.

To put it briefly, arranging at least four sensor coils in the same direction along the same line will give four different equations, which will give clues to the solution of the four unknown terms. Then, we can estimate the space occupied by the source coil as a circle around the coil.

Figure 15:
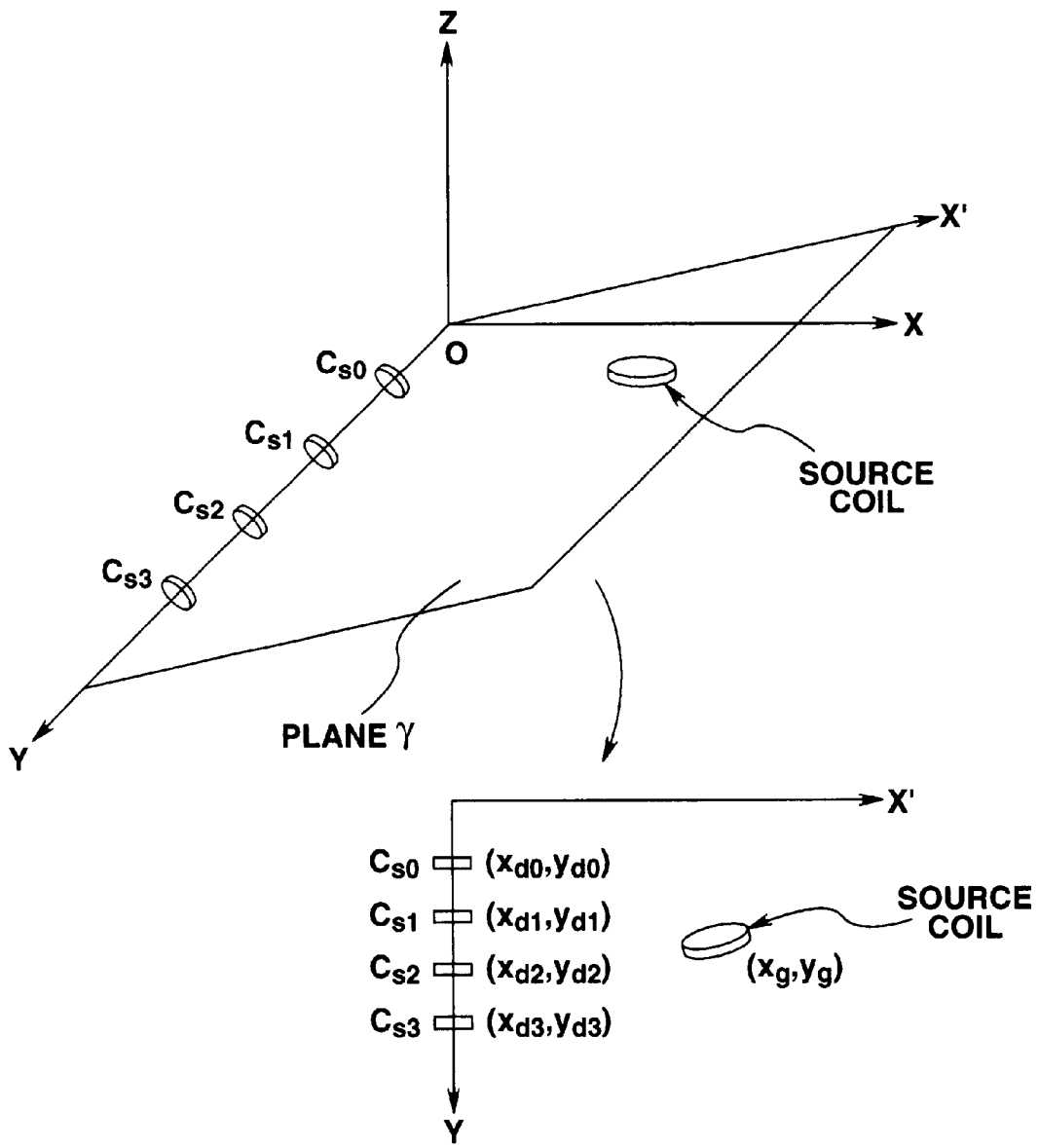

To put it more in detail, let's assume a source coil generating a magnetic field in a 3D space, and four sensor coils on Y-axis as shown in FIG. 15, and let's assume further the plane $\gamma$ determined by the source coil and four sensor coils corresponds to a 2D coordinate system X'-Y, and the coordinates of source coil and sensor coils in that plane coordinate system are ($x_g$, $y_g$), and ($x_{d0}$, $Y_{d0}$) ($X_{d1}$, $Y_{d1}$), ($X_{d2}$, $Y_{d2}$) and ($Xd_{d3}$, $Yd_{d3}$), respectively.

The electromotive forces $V_{y0}$, $V_{y1}$, $Vy_{y2}$ and $Vy_{y3}$ induced in the sensor coils $C_{s0}$, $C_{s1}$, $C_{s2}$ and $C_{s3}$ can be derived from Equation (17) as $$V_{y0} = \frac{k_{s0}}{r_0^5}[3(x_{d0} - x_g)(y_{d0} - y_g)g_x + \{2(y_{d0} - y_g)^2 - (x_{d0} - x_g)^2\}g_y] \tag{18}$$

$$V_{y1} = \frac{k_{s1}}{r_1^5}[3(x_{d1} - x_g)(y_{d1} - y_g)g_x + \{2(y_{d1} - y_g)^2 - (x_{d1} - x_g)^2\}g_y] \tag{19}$$

$$V_{y2} = \frac{k_{s2}}{r_2^5}[3(x_{d2} - x_g)(y_{d2} - y_g)g_x + \{2(y_{d2} - y_g)^2 - (x_{d2} - x_g)^2\}g_y] \tag{20}$$

$$V_{y3} = \frac{k_{s3}}{r_3^5}[3(x_{d3} - x_g)(y_{d3} - y_g)g_x + \{2(y_{d3} - y_g)^2 - (x_{d3} - x_g)^2\}g_y] \tag{21}$$

Inspection of those equations shows the coefficient ksi (i=0, 1, 2, 3) can be determined by the parameters including the electric current passing through the source coil and the turns of a sensor coil under study. Thus, assumed that the sensor coils be placed at known locations, and electromotive forces induced in them be measured, Equations (18)–(21) can be expressed by four unknown variables $g_x$, $g_y$, $x_g$ and $y_g$.

Solution of these simultaneous equations including the four unknown variables will give the coordinate ($x_g$, $y_g$) of the source coil in the plane coordinate system determined by Y-axis and source coil, which will then give us an estimation of the space (circle) within which the source coil exists.

The equations (19) and (20), when put into matrix form, will give $$\begin{pmatrix} V_{y1} \\ V_{y2} \end{pmatrix} = \tag{22}$$

$$\begin{pmatrix} \frac{k_{s1}}{r_1^5}3(x_{d1} - x_g)(y_{d1} - y_g) & \frac{k_{s1}}{r_1^5}\{2(y_{d1} - y_g)^2 - (x_{d1} - x_g)^2\} \\ \frac{k_{s2}}{r_2^5}3(x_{d2} - x_g)(y_{d2} - y_g) & \frac{k_{s2}}{r_2^5}\{2(y_{d2} - y_g)^2 - (x_{d2} - x_g)^2\} \end{pmatrix} \begin{pmatrix} g_x \\ g_y \end{pmatrix}$$

where the matrix A represents the term which is related with the locations of source coil and sensor coils. Equation 22 can be changed into $$\begin{pmatrix} V_{y1} \\ V_{y2} \end{pmatrix} = \begin{pmatrix} a_{00} & a_{01} \\ a_{10} & a_{11} \end{pmatrix} \begin{pmatrix} g_x \\ g_y \end{pmatrix} \quad (23)$$

Application of Cramer's formula to Equation 23 will give $A^{-1}$ or the reciprocal of matrix A as shown in $$A^{-1} = \frac{1}{a_{00}a_{11} - a_{01}a_{10}} \begin{pmatrix} a_{11} & -a_{01} \\ -a_{10} & a_{00} \end{pmatrix} \quad (24)$$

From Equation 24, $g_x$ and $g_y$ can be expressed as $$\begin{pmatrix} g_x \\ g_y \end{pmatrix} = \frac{1}{a_{00}a_{11} - a_{01}a_{10}} \begin{pmatrix} a_{11} & -a_{01} \\ -a_{10} & a_{00} \end{pmatrix} \begin{pmatrix} V_{y1} \\ V_{y2} \end{pmatrix} \quad (25)$$

When $A^{-1}$ or the reciprocal of matrix A is reduced to individual terms, and $g_x$ and $g_y$ are deduced from Equation (25), and they are put into Equations (18) and (21), following equations are obtained, that is, $$V_{y0} = \frac{K_1 R_1 (2Y_{02} + X_{02})(XY_{02} - XY_{20}) - K_2 R_2 (2Y_{01} + X_{01})(XY_{01} - XY_{10})}{R_0 (2Y_{12} + X_{12})(XY_{12} - XY_{21})} \quad (26)$$

$$V_{y3} = \frac{K_3 R_1 (2Y_{32} + X_{32})(XY_{32} - XY_{23}) - K_4 R_2 (2Y_{31} + X_{31})(XY_{31} - XY_{13})}{R_3 (2Y_{12} + X_{12})(XY_{12} - XY_{21})} \quad (27)$$

where individual terms are defined as $$\begin{aligned}
&K_1 = \frac{k_{s0}}{k_{s1}} V_{y1} \quad K_2 = \frac{k_{s0}}{k_{s2}} V_{y2} \quad K_3 = \frac{k_{s3}}{k_{s1}} V_{y1} \quad K_4 = \frac{k_{s3}}{k_{s2}} V_{y2} \\
&R_0 = r_0^5 \quad R_1 = r_1^5 \quad R_2 = r_2^5 \quad R_3 = r_3^5 \\
&X_{01} = (x_{d0} - x_g)(x_{d1} - x_g) \quad X_{02} = (x_{d0} - x_g)(x_{d2} - x_g) \\
&X_{31} = (x_{d3} - x_g)(x_{d1} - x_g) \quad X_{32} = (x_{d3} - x_g)(x_{d2} - x_g) \\
&Y_{01} = (y_{d0} - y_g)(y_{d1} - y_g) \quad Y_{02} = (y_{d0} - y_g)(y_{d2} - y_g) \\
&Y_{31} = (y_{d3} - x_g)(y_{d1} - y_g) \quad Y_{32} = (y_{32} - y_g)(y_{d2} - y_g) \\
&X_{12} = (x_{d1} - x_g)(x_{d2} - x_g) \quad Y_{12} = (y_{d1} - y_g)(y_{d2} - y_g) \\
&XY_{01} = (x_{d0} - x_g)(y_{d1} - y_g) \quad XY_{10} = (x_{d1} - x_g)(y_{d0} - y_g) \\
&XY_{02} = (x_{d0} - x_g)(y_{d2} - y_g) \quad XY_{20} = (x_{d2} - x_g)(y_{d0} - y_g) \\
&XY_{31} = (x_{d3} - x_g)(y_{d1} - y_g) \quad XY_{13} = (x_{d1} - x_g)(y_{d3} - y_g) \\
&XY_{32} = (x_{d3} - x_g)(y_{d2} - y_g) \quad XY_{23} = (x_{d2} - x_g)(y_{d3} - y_g) \\
&XY_{12} = (x_{d1} - x_g)(y_{d2} - y_g) \quad XY_{21} = (x_{d2} - x_g)(y_{d1} - y_g)
\end{aligned} \quad (28)$$

Equations (26) and (27) constitute non-linear simultaneous equations where $x_g$ and $y_g$ are unknown variables. Application of the Newton method to these non-linear equations will give numerical values of $x_g$ and $Y_g$.

Let's assume that the electromotive forces actually observed in the sensor coils be $V_{y0}'$, $V_{y3}'$. The corresponding theoretical values derivable from Equations (26) and (27) are $V_{y0}$, $V_{y3}$. The difference between the two can be expressed as $$f_1(X_g, Y_g) = V_{y0} - V_{y0}' \quad (29)$$

$$f_2(X_g, Y_g) = V_{y3} - V_{y3}' \quad (30)$$

$f_1(X_g, Y_g)$ and $f_2(X_g, Y_g)$ in Functions (29) and (30) will be 0 when $V_{y0}'$, $V_{y3}'$ or the electromotive forces actually observed in sensor coils are precisely determined, and the coordinates $(x_g, y_g)$ derived from the estimated electromotive forces $V_{y0}$, $V_{y3}$ coincide with the actual coordinates of the source coil.

To determine the location of source coil, $x_g$ and $y_g$ are calculated that satisfy $f_1=0$ and $f_2=0$.

$f_1$ and $f_2$ are submitted to partial differentation in terms of $x_g$ and $y_g$ to give a Jacobian matrix as represented by $$J = \begin{pmatrix} \frac{\partial f_1}{\partial x_g} & \frac{\partial f_1}{\partial y_g} \\ \frac{\partial f_2}{\partial x_g} & \frac{\partial f_2}{\partial y_g} \end{pmatrix} \quad (31)$$

Application of Cramer's formula to Equation 31 will give $J^{-1}$ or the reciprocal of Jacobian matrix J as shown in $$J^{-1} = \begin{pmatrix} C_{00} & C_{01} \\ C_{10} & C_{11} \end{pmatrix} \quad (32)$$

which is designated as matrix C.

The Newton method consists of applying repetitively $f(X)=0$ to a non-linear equation defined as $X^{(k+1)}=X^{(k)}-\Delta X^{(k)}$, and of determining the correction term $\Delta X^{(k)}$ on the basis of linear approximation at a segment of $f(X)$ determined by $X=X^{(k)}$.

$$\Delta X^{(k)} = J^{-1}(X^{(k)}) \cdot F(X^{(k)})$$

Let's assume the initial values of $x_g$ and $y_g$ be $x_{g0}$ and $y_{g0}$. Then, $x_{g1}$ and $y_{g1}$ approximate to $x_g$ and $y_g$ respectively can be derived as $$x_{g1} = x_{g0} - \{c_{00}f_1(x_{g0}, y_{g0}) + c_{01}f_2(x_{g0}, y_{g0})\} \quad (33)$$

$$y_{g1} = y_{g0} - \{c_{10}f_1(x_{g0}, y_{g0}) + c_{11}f_2(x_{g0}, y_{g0})\} \quad (34)$$

The numerical values of $x_{g1}$ and $y_{g1}$ are put into Equations (29) and (30) to see whether $f_1$ and $f_2$ be 0 or not. If they do not give 0, put the numerical values of $x_{g1}$ and $y_{g1}$ into $x_{g0}$ and $y_{g0}$ of Equations (33) and (34) to get the numerical values of $x_{g2}$ and $y_{g2}$. Then, put those numerical values into Equations (29) and (30) to see whether they render $f_1$ and $f_2$ to 0 or not. Repetition of this process will allow $f_1$ and $f_2$ to be increasingly closer to 0 and $x_g$ and $y_g$ to be determined.

The Newton method was applied above for the solution of the non-linear equation, but the least mean square method may be used instead.

Outputs from a sensor coil set comprising four single core coils arranged along the same line in the same direction may allow one to estimate the location of a source coil on the plane determined by the sensor coils and source coil. To put it otherwise, they allow one to estimate the range (circle) occupied by the source coil in a 3D space.

Arranging four single core coils makes it possible to solve a non-linear equation including two unknown variables, and thus to determine the location of a source coil easily.

As described earlier, based on outputs from a set of sensor coils which comprise at least four single core coils arranged along the same line in the same direction, one can determine the range (circle) occupied by a single core coil (source coil) which generates a magnetic field. Accordingly, arranging at least two sets of sensor coils will make it possible to definitively determine the location of the source coil (by determining the crossing point of the two circles separately determined by the two sets of sensor coils)

In this embodiment, it is assumed as appropriate that an intersection of the two circles or the two points on the two circles which give the shortest interval will determine the location of source coil (there are cases where two circles have no intersection owing to noises and others).

Figure 16:
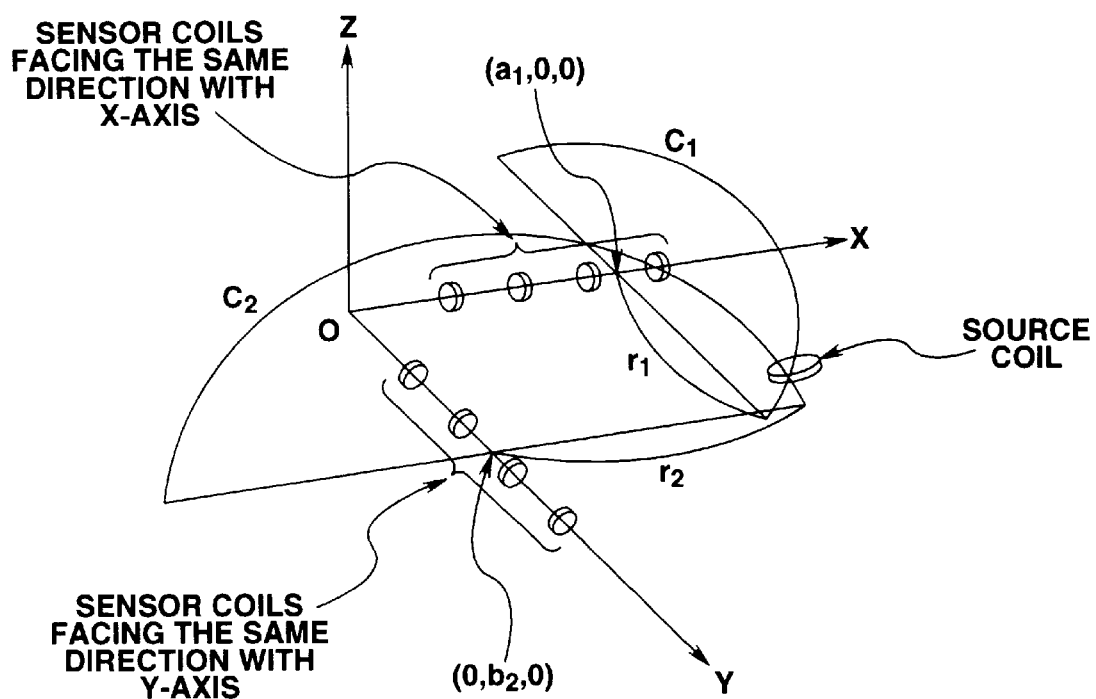

A source coil is placed at an arbitrary point within a coordinate system, and two sets of sensor coils are placed along X- and Y-axis as shown in FIG. 16. Outputs from the two sets of sensor coils will determine circles $C_1$ and $C_2$ within which the source coil exists, as was discussed earlier. $C_1$ represents a circle existing on the plane normal to X-axis and intercepting at $x=a_1$ on X-Y plane with a center $(a_1, 0, 0)$ and a radius of $r_1$, while $C_2$ represents a circle existing on the plane normal to Y-axis and intercepting at $y=b_2$ on X-Y plane with a center $(0, b_2, 0)$ and a radius of $r_2$. Then, $C_1$ and $C_2$ can be expressed as $$C_1: (x-a_1)^2+y^2+z^2=r_1^2 \tag{35}$$

$$C_2: x^2+(y-b_2)^2+z^2=r_2^2 \tag{36}$$

Figure 17:
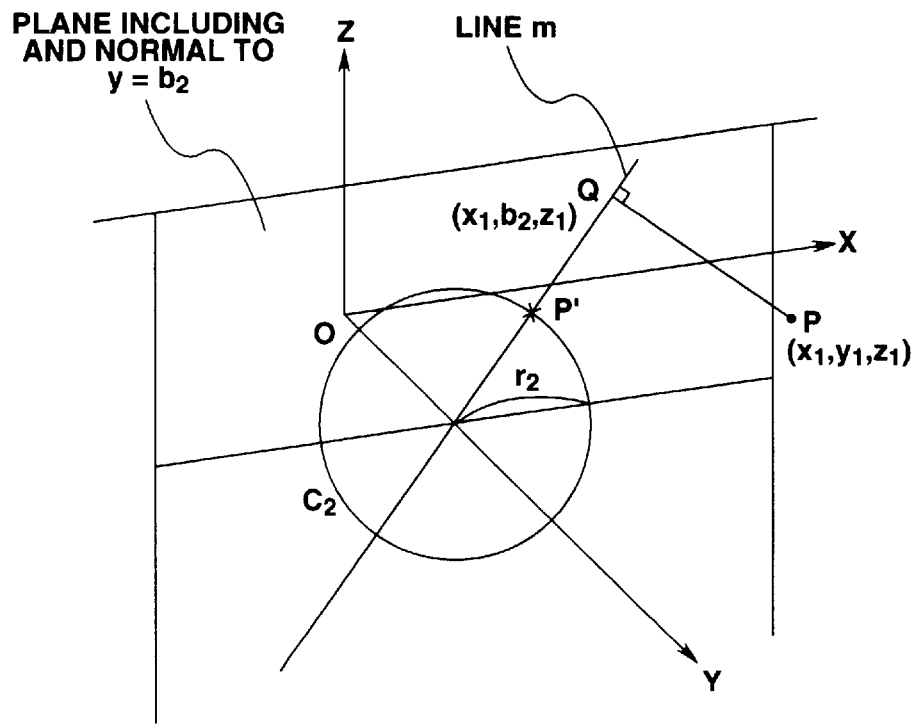
Figure 18:
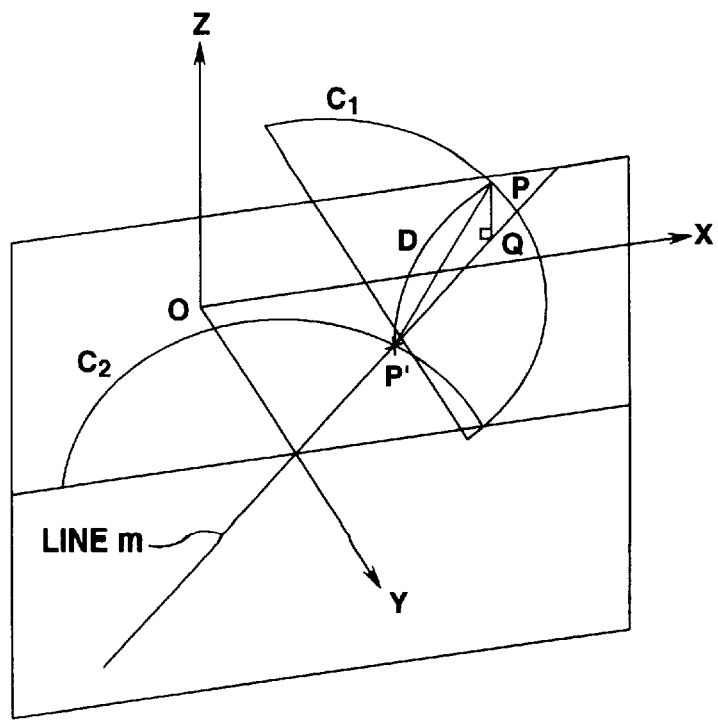

As shown in FIG. 17, when a point P is taken arbitrarily at $(x_1, y_1, z_1)$, and from P is drawn a line normal to the plane normal to Y-axis and intercepting at $y=b_2$ on X-Y plane, to give an intersection Q whose coordinates can be expressed as $$(x_1, b_2, z_1).$$

The straight line m which passes through the point Q and center $(0, b_2, 0)$ of circle $C_2$ and exists on the plane (normal to Y-axis and intercepting at $y=b_2$) can be expressed as $$x=x_1+tx_1$$
$$y=b_2$$
$$z=z_1+tz_1 \tag{37}$$

where t represents a real variable.

When the variables in Equation (36) determining circle $C_2$ are substituted by corresponding variables in Equation (35), what results is $$(x_1+tx_2)^2+(z_1+tz_1)^2=r_2^2 \tag{38}$$

where t can be expressed as $$t = \pm \frac{r_2}{(x_1^2+z_1^2)^{\frac{1}{2}}} - 1 \tag{39}$$

The line m crosses the circle $C_2$ at two points. As obviously $t>0$, the positive t from Equation (39) is put into Equation (37) to give $$x = \frac{x_1 r_2}{(x_1^2+z_1^2)^{\frac{1}{2}}} \tag{40}$$

$$y = b_2$$

$$z = \frac{z_1 r_2}{(x_1^2+z_1^2)^{\frac{1}{2}}}$$

The coordinates (40) determines a point P' on circle $C_2$ which is the shortest distance apart from point P as shown in FIG. 17. Provided here that point P $(x_1, y_1, z_1)$ is on circle $C_1$, then $$x_1=a_1$$

$$y_1=r_1 \cos \theta$$

$$z_1=r_1 \sin \theta \tag{41}$$

When variables in Equation (40) are substituted by the corresponding numerical values of Coordinates (41), what results is $$x = \frac{a_1 r_2}{(a_1^2+r_1^2\sin^2\theta)^{\frac{1}{2}}} \tag{42}$$

$$y = b_2$$

$$z = \frac{r_1 r_2 \sin\theta}{(a_1^2+r_1^2\sin^2\theta)^{\frac{1}{2}}}$$

The second power of distance D between a point on circle $C_1$ and another point on circle $C_2$ can be expressed as $$D = \left\{ \frac{a_1 r_2}{(a_1^2+r_1^2\sin^2\theta)^{\frac{1}{2}}} - a_1 \right\}^2 + (b_2 - r_1\cos\theta)^2 + \tag{43}$$

$$\left\{ \frac{r_1 r_2 \sin\theta}{(a_1^2+r_1^2\sin^2\theta)^{\frac{1}{2}}} - r_1\sin\theta \right\}^2$$

$$= \left\{ r_2 - (a_1^2+r_1^2\sin^2\theta)^{\frac{1}{2}} \right\}^2 + (b_2-r_1\cos\theta)^2$$

Equation 43, when submitted to differentiation in terms of $\theta$, will give $$\frac{dD}{d\theta} = -2 \left\{ \frac{r_1 r_2 \cos\theta}{(a_1^2+r_1^2\sin^2\theta)^{\frac{1}{2}}} - b_2 \right\} r_1 \sin\theta \tag{44}$$

For Equation (44) to be 0, $\sin \theta = 0$ (This applies to the cases where the two circles do not cross each other, and $r_1<a_1$ and $r_1<b_2$, or $r_1<b_2$ or $r_2<a_1$) or $$\frac{r_1 r_2 \cos\theta}{(a_1^2+r_1^2\sin^2\theta)^{\frac{1}{2}}} - b_2 = 0 \tag{45}$$

The $\theta$ which satisfies Equation (45) is expressed as $$r_1 r_2 \cos\theta = b_2(a_1^2+r_1^2\sin^2\theta)^{\frac{1}{2}} \tag{46}$$

$$\cos^2\theta = \frac{(b_2^2 a_1^2 + b_2^2 r_1^2)}{(r_1^2 r_2^2 + b_2^2 r_1^2)}$$

$$\theta = \cos^{-1}\left\{ \pm \sqrt{\frac{(b_2^2 a_1^2 + b_2^2 r_1^2)}{(r_1^2 r_2^2 + b_2^2 r_1^2)}} \right\}$$

Equations (46), (40) and (41) will give the coordinates of the two points on circle $C_1$ and $C_2$ which give the shortest interval.

Let's assume the coordinates of the two points in question be $(x_{c1}, y_{c1}, z_{c1})$ on circle $C_1$ and $(x_2, y_{c2}, z_{c2})$ on circle $C_2$. Then, the coordinates $(x_g, y_g, z_g)$ of source coil can be determined, for example, by calculating the averages of corresponding coordinates as seen in $$x_g = \frac{x_{c1} + x_{c2}}{2} \quad (47)$$

$$y_g = \frac{y_{c1} + y_{c2}}{2}$$

$$z_g = \frac{z_{c1} + z_{c2}}{2}$$

From above it is obvious that arranging two sets of sensor coils each comprising four single core coils placed along the same line in the same direction will allow one to estimate the location of a source coil in a 3D space.

As discussed earlier, outputs from two sets of sensor coils determine two ranges (circle) within which a source coil exists, and by calculating the intersection of the two ranges, one can estimate the location of the source coil. In this arrangement, if the axis of source coil intersects at right angles the plane γ determined by the sensor coils and source coil, it will evoke no electromotive force in the sensor coils. Then, we will have no clues as to the space (circle) occupied by the source coil.

Recourse is made to an alternative method, when the axis of a source coil is directed normal to the plane determined by the sensor coils and source coil. The method utilizes the normality itself of the source coil to the plane in question.

Figure 19:
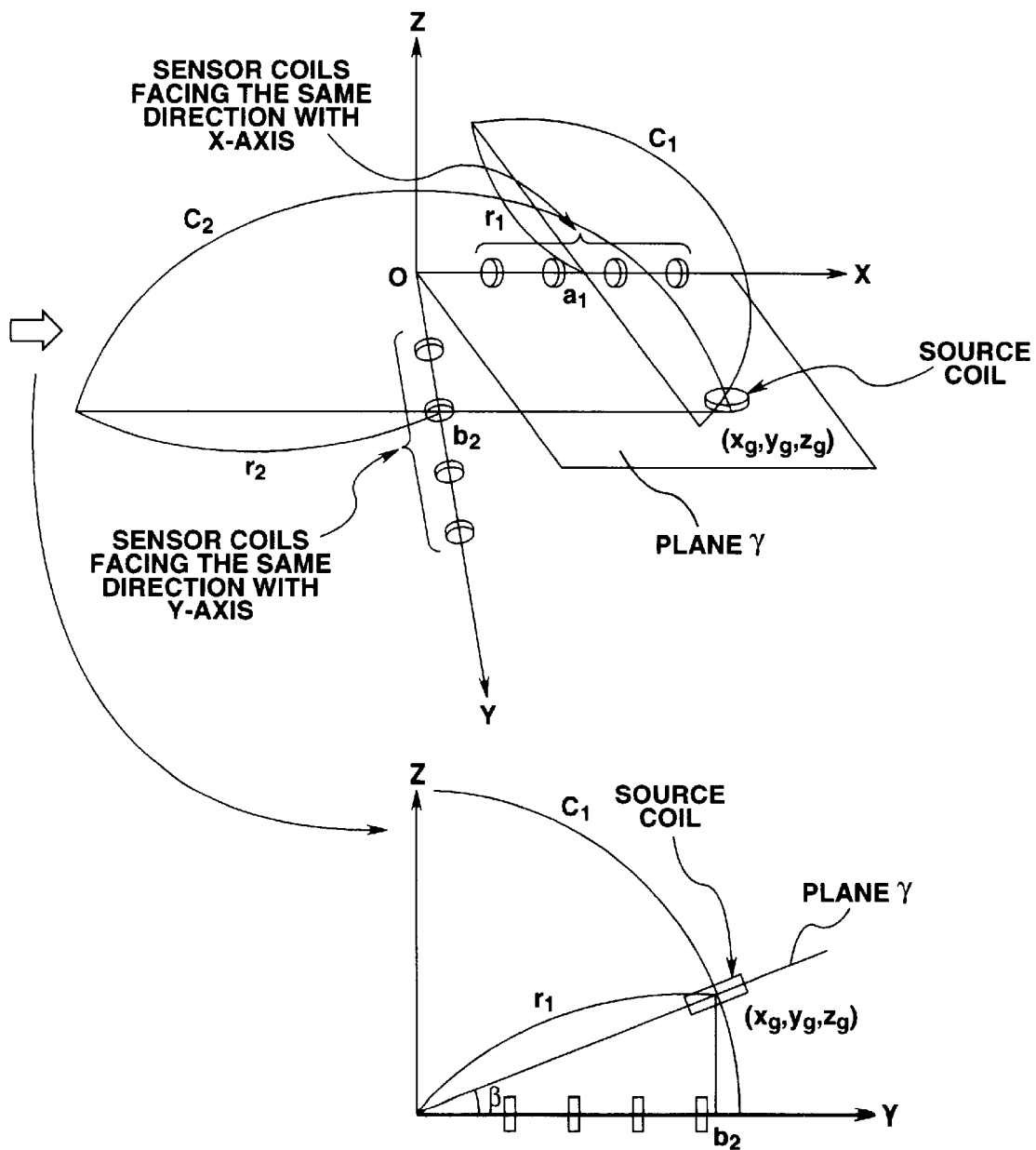

A set of sensor coils arranged on X-axis is termed as $S_x$ while another set of sensor coils arranged on Y-axis as $S_y$. The circle given by the sensor coils $S_x$ within which the source coil exists is termed as $C_1$ while the counterpart determined by the sensor coils $S_y$ is termed as $C_2$ as shown in FIG. 19.

Then, $C_1$ represents a circle existing on the plane normal to X-axis and intercepting X-Y plane at $x=a_1$ with a center $(a_1, 0, 0)$ and a radius of $r_1$, while $C_2$ represents a circle existing on the plane normal to Y-axis and intercepting X-Y plane at $y=b_2$ with a center $(0, b_2, 0)$ and a radius of $r_2$.

As the axis-of source coil intersect at right angles the plane γ which is determined by the sensor coils on X-axis and source coil, the rotation angle α with respect to Z-axis becomes 0. The angle the axis of source coil has relative to Y-axis can be given when a unit vector $(0, 0, 1)$ is turned by β around X-axis.

Thus, the vector which determines the direction of the axis of source coil can be expressed by $$\begin{pmatrix} 1 & 0 & 0 \\ 0 & \cos\beta & \sin\beta \\ 0 & -\sin\beta & \cos\beta \end{pmatrix} \begin{pmatrix} 0 \\ 0 \\ 1 \end{pmatrix} = \begin{pmatrix} 0 \\ \sin\beta \\ \cos\beta \end{pmatrix} \quad (48)$$

Assumed that this vector be a normal vector, the plane γ passing through X-axis can be expressed as $$y \sin\beta + z \cos\beta = 0 \quad (49)$$

In addition, the equation determining circle $C_2$ can be given by $$y = b_2$$

$$x^2 + z^2 = r_2^2 \quad (50)$$

From Equations (49) and (50), the intersection $(x_g, y_g, z_g)$ of circle $C_2$ with plane γ can be given as $$x_g = \pm (r_2^2 - z_g^2)^{1/2}$$

$$y_g = b_2$$

$$z_g = -b_2 \tan\beta \quad (51)$$

These coordinates give the location of source coil.

In this case, because the axis of source coil is normal to the plane γ, rotation of the axis with respect to Z-axis becomes 0 (α=0), and thus, from Equation (8), the voltage induced in a sensor coil placed at $(0, y_d, 0)$ on Y-axis will be given by $$V_{dy} = \frac{k_s}{r^5}[\{-x_g^2 + 2(y_d - y_g)^2 - z_g^2\}\sin\beta - 3(y_d - y_g)z_g\cos\beta] \quad (52)$$

$$r^5 = (x_g^2 + (y_d - y_g)^2 + z_g^2)^{\frac{5}{2}}$$

$x_g$ in Equation (51) is transformed into $$r_2^2 = x_g^2 + z_g^2$$

which is then put into Equation (52) to give $$V_{dy} = \frac{k_s}{r^5}[\{-r_2^2 + 2(y_d - b_2)^2\}\sin\beta + 3(y_d - b_2)b_2\sin\beta] \quad (53)$$

$$= \frac{k_s}{r^5}[\{-r_2^2 + 2(y_d - b_2)^2 + 3(y_d - b_2)b_2\}\sin\beta]$$

Equation (53) is modified to isolate β as given by $$\beta = \sin^{-1}\left[\frac{V_{dy}r^5}{k_s\{-r_2^2 + 2(y_d - b_2)^2 + 3(y_d - b_2)b_2\}}\right] \quad (54)$$

The axis of source coil is given by Equation (54) and the coordinates by Equation (51).

The same logic holds for the case where sensor coils $S_y$ are arranged on Y-axis, and the axis of source coil is normal to the plane determined by those sensor coils and source coil. In this case $$\beta = \sin^{-1}\left[\frac{V_{dx}r^5}{k_s\{-r_1^2 + 2(x_d - a_1)^2 + 3(x_d - a_1)a_1\}}\right] \quad (55)$$

will allow one to obtain the location of source coil in a 3D space.

To sum it all, even when a source coil is placed with respect to sensor coils such that it evokes no potential in the latter, or the source coil is so placed as to put its axis normal to the plane determined by the sensor coils and source coil, the location of source coil can be determined.

When outputs from sensor coils are very small, they can not be distinguished from noises. To meet such situation, a threshold may be introduced: when the output from a sensor coil is lower than the threshold, it is assumed to be 0, and all the results over the threshold are taken into consideration to give the location of source coil according to the above-described method.

Now, the procedure how CPU 32 actually estimates the location of a source coil by the use of above method will be detailed below for illustration.

As shown in FIG. 1, two sets of sensor coils 22j each comprising four single core coils placed on the same line in the same direction are arranged so as to meet at a right angle in a bed 4. A source coil 14i comprising an array of 16 single core coils or a probe 15 is inserted through a forceps channel 12 of an electronic endoscope 6.

The endoscope shape reconstructing apparatus 3 collects voltage and phase data of potentials induced in sensor coils 22j by the array of source coils 14i, determines the polarity (whether it be positive or negative) of the maximum amplitude of evoked potential from the corresponding phase data, and accepts maximum amplitude voltages with a polarity as outputs from the sensor coils 22j.

Figure 20:
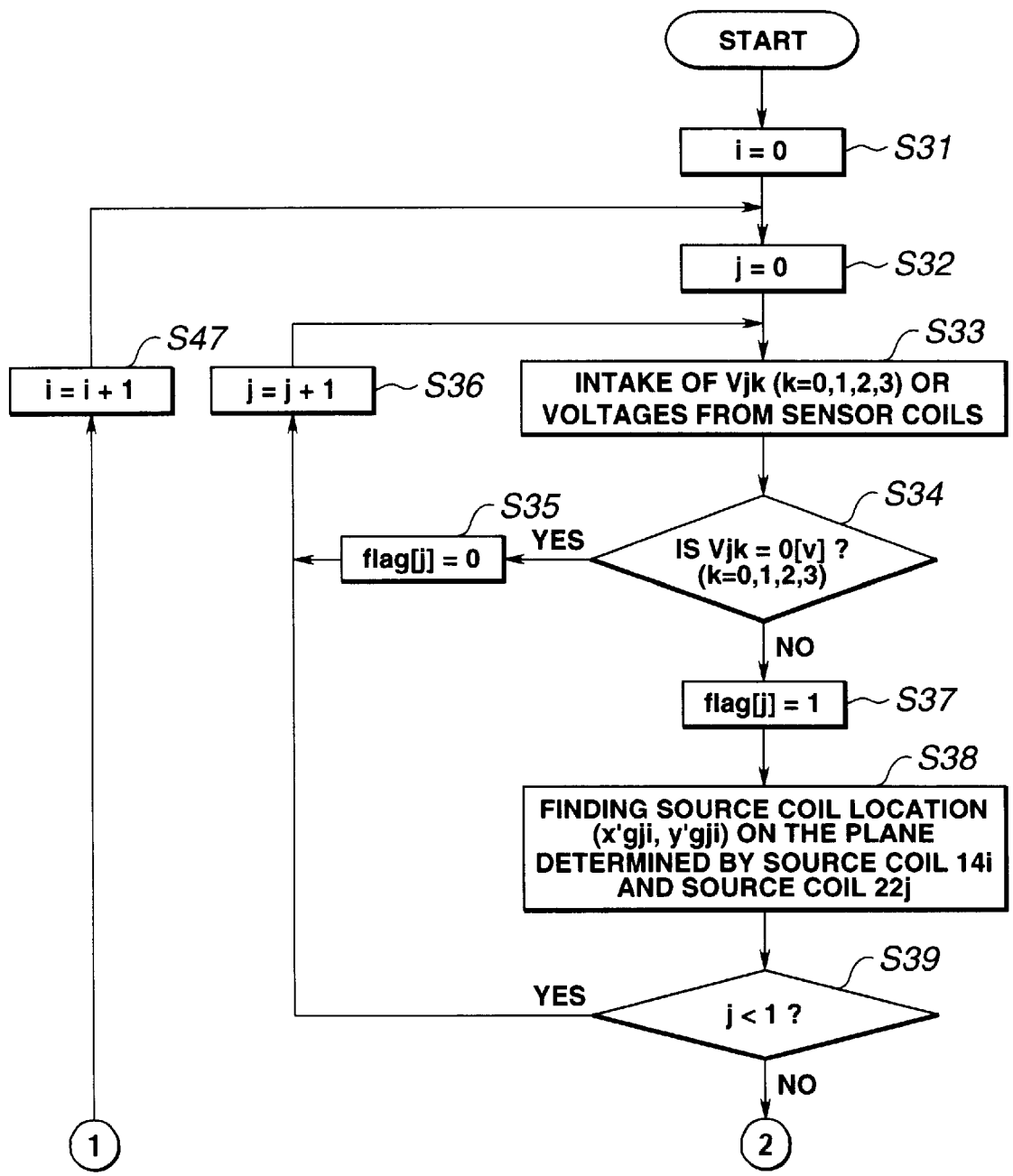

To put it more specifically, as shown in FIG. 20, CPU 32 firstly initializes the order of source coils 14i and sensor coils 22j for processing at steps S31 and S32. Thus, it sets i=0 at step S31 and j=0 at step S32.

Firstly, 0th source coil and 0th sensor coil are picked up for processing: at step S33, voltages $V_{00}$, $V_{01}$, $V_{02}$ and $V_{03}$ induced in the four single core coils constituting the 0th sensor coil set are collected. The voltages collected at step S33 are transmitted to step S34 where they are checked for their being 0[V] or not.

When at step S34 all the voltages $V_{00}$, $V_{01}$, $V_{02}$ and $V_{03}$ from the four single core coils constituting the 0th sensor coil set are found to be 0[V], it indicates that the axis of 0th source coil is normal to the plane determined by the 0th sensor coil set and 0th source coil. When CPU meets this situation, it advances to step S35, sets the flag of 0th sensor coil set to 0, advances to step S36 where it increments j by one unit, and returns to step S33 to proceed to the processing of 1st sensor coil set.

When at step S34 CPU finds that all the voltages $V_{00}$, $V_{01}$, $V_{02}$ and $V_{03}$ provided by four single core coils constituting a sensor coil set are not 0[V], it advances to step S37 where it sets the flag of 0th sensor coil set to 1.

Then, at step S38, CPU determines the coordinates ($x'_{g00}$, $y'_{g00}$) of 0th source coil on the plane determined by 0th sensor coil set and 0th source coil.

At step S39, CPU checks whether outputs from 0th and 1st sensor coil sets have been processed to give 2D coordinates of 0th source coil. At this step when it finds j=0, it recognizes that processing of outputs from 1st sensor coil set is not done yet to give 2D coordinates of 0th source coil. Then, it advances to step S36 where it increments j by one unit, and returns to step S33 where it starts to process outputs from 1st sensor coil set.

CPU exercises the same processing at steps S33 to S38 as was discussed earlier. Because j remains to be unit (j=1) throughout this operation, CPU confirms at step S39 that processing of outputs from 0th and 1st sensor coil sets is completed and it obtains two 2D coordinates (($x'_{g00}$, $y'_{g00}$) and ($x'_{g10}$, $y'_{g10}$)) of 0th source coil.

Processes at steps S32 to S39 are a realization of the theoretical procedures discussed earlier with reference to FIGS. 9 to 15, and they give two 2D locations of a source coil on the planes determined by sensor coil sets and source coil.

Figure 21:
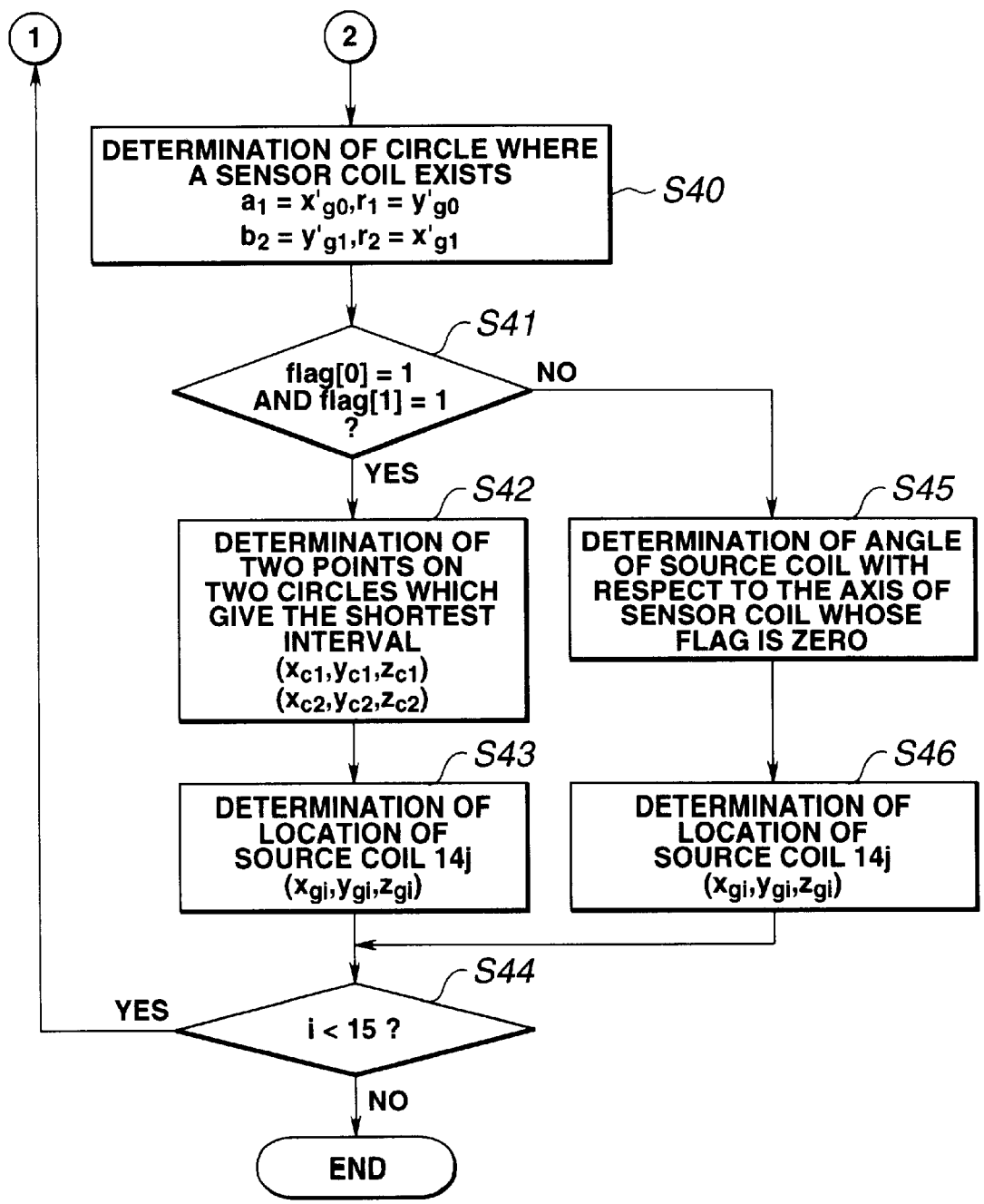

Having completed the processes up to step S39, CPU proceeds to step S40 in FIG. 21 where it determines the range (circle) of a source coil from its location in the 2D space which have been derived at step S38 from outputs of a sensor coil set.

At step S41, CPU checks whether all flags are unit or not. When it finds all flags are unit and confirms that the axis of source coil under study is not normal to the plane determined by the sensor coil set and source coil, it advances to step S42 where it determines two points on the two circles which have been provided by two different sets of sensor coils that give the shortest interval. At step S43, the coordinates of the two points are averaged to give a location of 0th source coil in a 3D space. Then, CPU advances to step S44.

Alternatively, when CPU finds at step S41 that not all flags are unit, or, in other words, that the axis of source coil under study is normal to the plane determined by either one of the two sensor coil sets, it calculates at step S45 the angle of source coil with respect to the axis on which the sensor coil set in question has been placed, advances to step S46 where it seeks the location of source coil in a 3D space from that angle, and then goes to step S44.

At step S44, CPU checks whether the coordinates of all source coils in a 3D space have been obtained or not. When it finds i=0 here, it advances to step S47 where it increments i by one unit, returns to step S32, repeats the same processes at steps S32 to S47, confirms at step S44 that the coordinates of the last source coil in the 3D space have been determined, and completes the processing.

Processes performed at steps S40 to S43 are a realization of the theoretical considerations discussed earlier with reference to FIGS. 6 to 18, while those at steps S45 to S46 are a realization of the theoretical consideration discussed with reference to FIG. 19.

From above it is obvious that two sets of sensor coils each comprising four single core coils placed on the same line in the same direction will enable one to locate a source coil in a 3D space.

Figure 22:
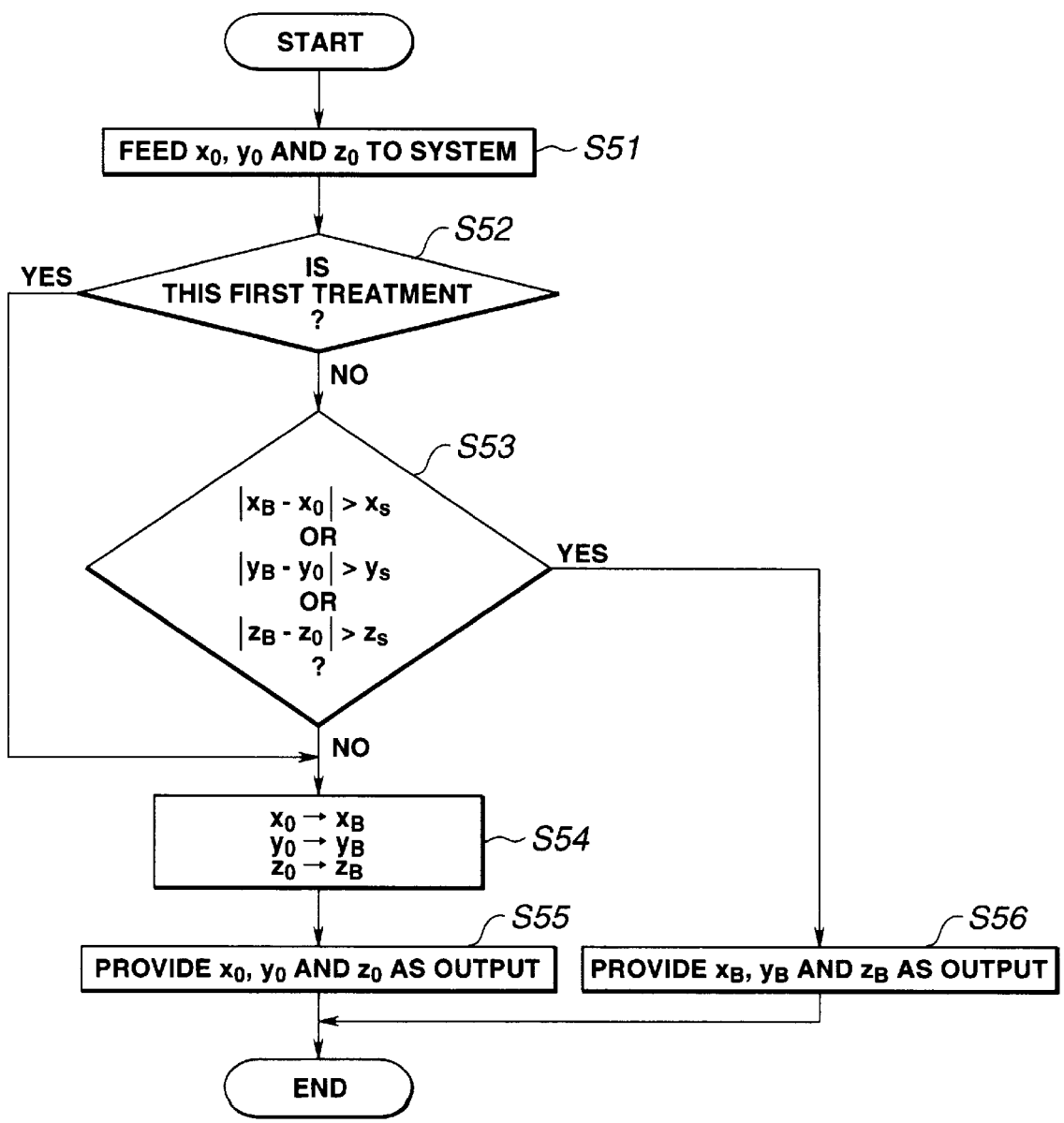

The locations of source coils in a 3D space are always updated, which is performed through the location updating processing as depicted in FIG. 22. To think it in more concrete terms, let's assume the location of 0th source coil be updated, and it currently have coordinates ($x_0$, $y_0$, $z_0$) in a 3D space. At step S51, CPU receives the coordinates ($x_0$, $y_0$, $z_0$), and checks at step S52 whether these coordinates are the same with those of the same source coil obtained through the first source coil location estimating process. When it finds the former is different from the latter, it goes to step S53. When it finds instead the former is the same with the latter, it advances to step S54.

When CPU finds the coordinates in question the same with the first coordinates, it converts the coordinates in question ($x_0$, $y_0$, $z_0$) into the first coordinates ($x_B$, $y_B$, $z_B$) to be stored, advances to step S55 where it provides the coordinates ($x_0$, $y_0$, $z_0$) as the current output for estimating the location of source coil, and completes operation.

Now let's assume that the coordinates ($x_0$, $y_0$, $z_0$) be obtained through the second session of processing, instead of through the first processing as in the previous case. In this case too, CPU receives the coordinates ($x_0$, $y_0$, $z_0$) at step S51, checks at step S52 whether the coordinates in question are the same with those derived from the first session of processing, confirms that the former is different from the latter, advances to step S53 where it calculates the absolute differences between the current and previous coordinates ($x_0$, $y_0$, $z_0$) and ($x_B$, $y_B$, $z_B$), and checks whether the differences are larger than the specified variation limits ($x_S$, $y_S$, $z_S$) assigned to X-, Y-, and Z-coordinates respectively, and, when it finds any differences do not exceed the limits, it advances to step S54 where it converts the coordinates ($x_0$, $y_0$, $z_0$) into ($x_B$, $y_B$, $z_B$) for storage as in the first processing, advances to step S55 where it provides the coordinates ($x_0$, $y_0$, $z_0$) as the output of the current source coil location estimating process, and completes operation.

When, however, CPU finds at step S53 that absolute differences between the current and previous coordinates ($x_0$, $y_0$, $z_0$) and ($x_B$, $y_B$, $z_B$) exceed the specified variation limits ($x_S$, $y_S$, $z_S$), it advances to step S56 where it provides the coordinates ($x_B$, $y_B$, $z_B$) of previous processing as the output of current processing, and complete operation.

In this way, the derived coordinates are modified with reference to the variation limits ($x_S$, $y_S$, $z_S$) assigned to X-, Y- and Z-coordinates, respectively.

FIG. 22 illustrates a processing of 0th source coil, but the same processing is repeated for the remaining source coils.

Next, the process at step S13 in FIG. 6 which is to reconstruct the endoscope shape image and display it on the monitor will be presented below.

Figure 23:
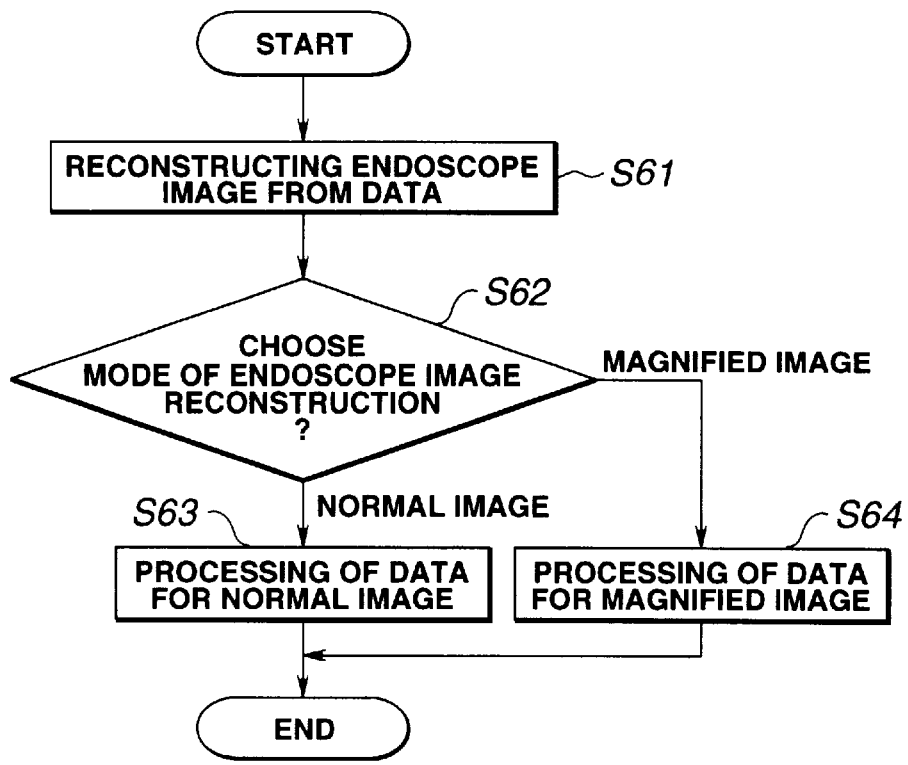

As shown in FIG. 23, the endoscope shape image reconstruction processing consists of compiling at step S61 data necessary for the reconstruction of an endoscope image from the coordinate data of source coils with respect to a 3D space obtained through the previous source coil location estimating process. Then, CPU checks at step S62 which imaging mode has been selected on the console of endoscope shape reconstructing apparatus 3, that is, the way the endoscope image is presented including normal mode and magnified mode. When it finds the normal mode has been selected, it advances to step S63 where it initiates normal mode processing, while, on finding the magnified mode has been selected, it moves to step S64 for magnified mode processing.

Figure 24:
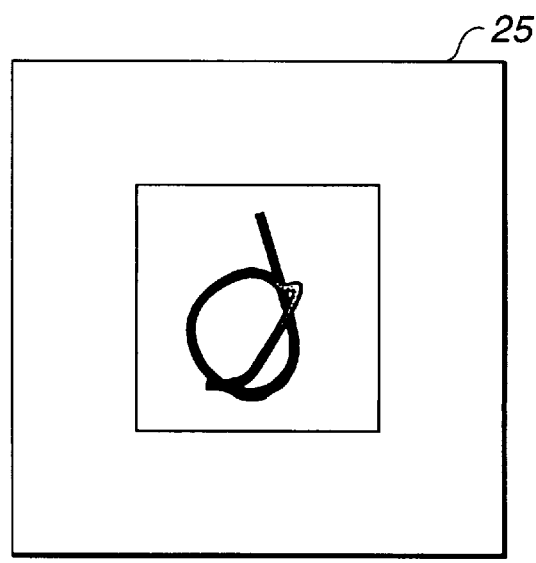

Thus, when the normal mode is selected, an image of endoscope shape as shown in FIG. 24 is displayed on the monitor 25 of endoscope shape reconstructing apparatus 3.

On the other hand, when the magnified mode is selected, it is necessary to choose at step S71 what part of the endoscope image displayed on the monitor 25 (see FIG. 24) is to be enlarged. For this purpose, the operator manipulates appropriate control dials on the panel 24, determines a rectangular range to include the part of interest, and feeds the coordinates of the upper left and lower right corners of that rectangle to the apparatus 3. CPU, on receiving the coordinate data, checks at first whether the two sets of coordinates are the same or not at step S72, and when it finds they are the same, it returns to step S71 because then it can not find any range to enlarge. On the contrary, when CPU finds the two sets of coordinate data are different, it advances to step S73.

At step S73, CPU determines the center of selected rectangle and the center of current endoscope image, moves the latter towards the former until the two coincide, and at step S74 enlarges the rectangle together with the endoscope image included therein until its sides coincide with the frame of screen, and completes operation.

Figure 25:
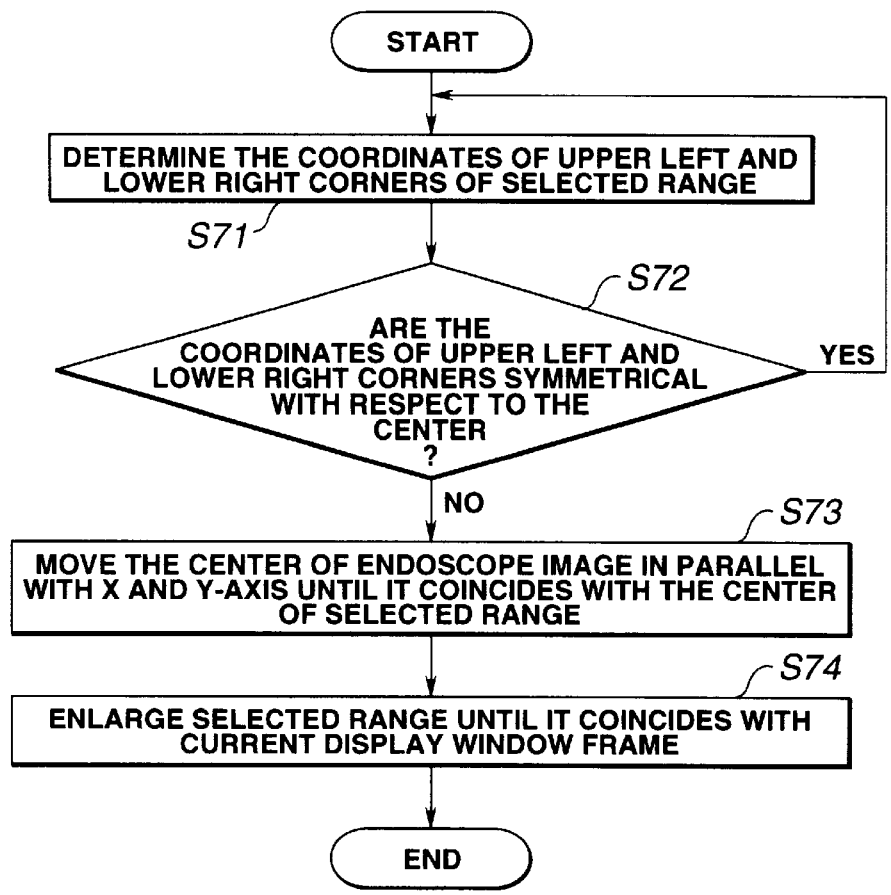
Figure 26:
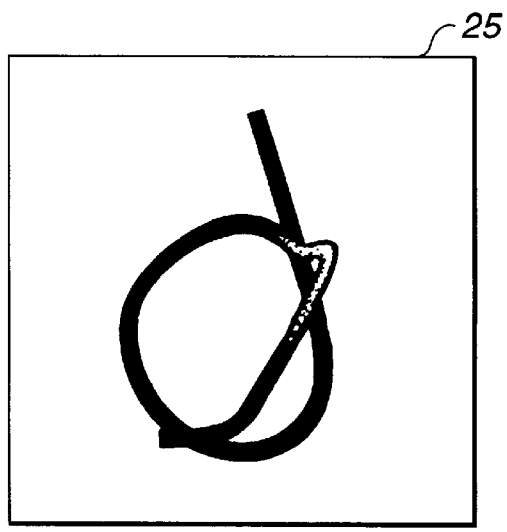

Through this operation, the endoscope image displayed on the monitor 25 as illustrated in FIG. 24 is enlarged into the image on the monitor 25 as shown in FIG. 25.

With the present apparatus the endoscope image can be displayed in following different modes.

(1) 3D image 1 and 3D image 2
(2) 2D image
(3) 12 point-in-series image
(4) Dot-line image.

Figure 27:
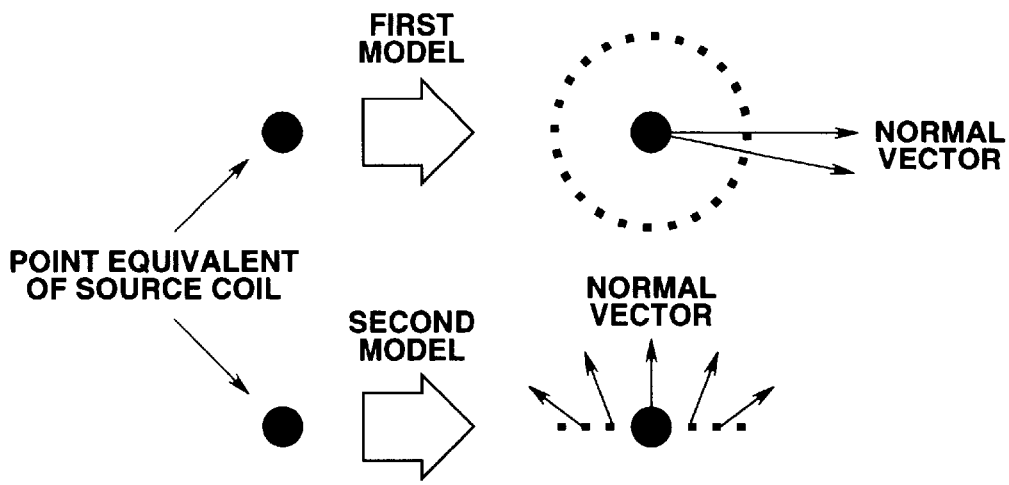

Display of an endoscopic image in 3D image 1 or 3D image 2 mode is achieved by applying curvilinear approximation with third degree functions or with natural lines, and approximation with three degree B-splining or second degree B-splining. As shown in FIG. 27, a point representing a source coil is treated differently in the two imaging modes to give two different normal vectors, which are then processed and assembled to provide two different 3D images of an endoscope.

Figure 28:
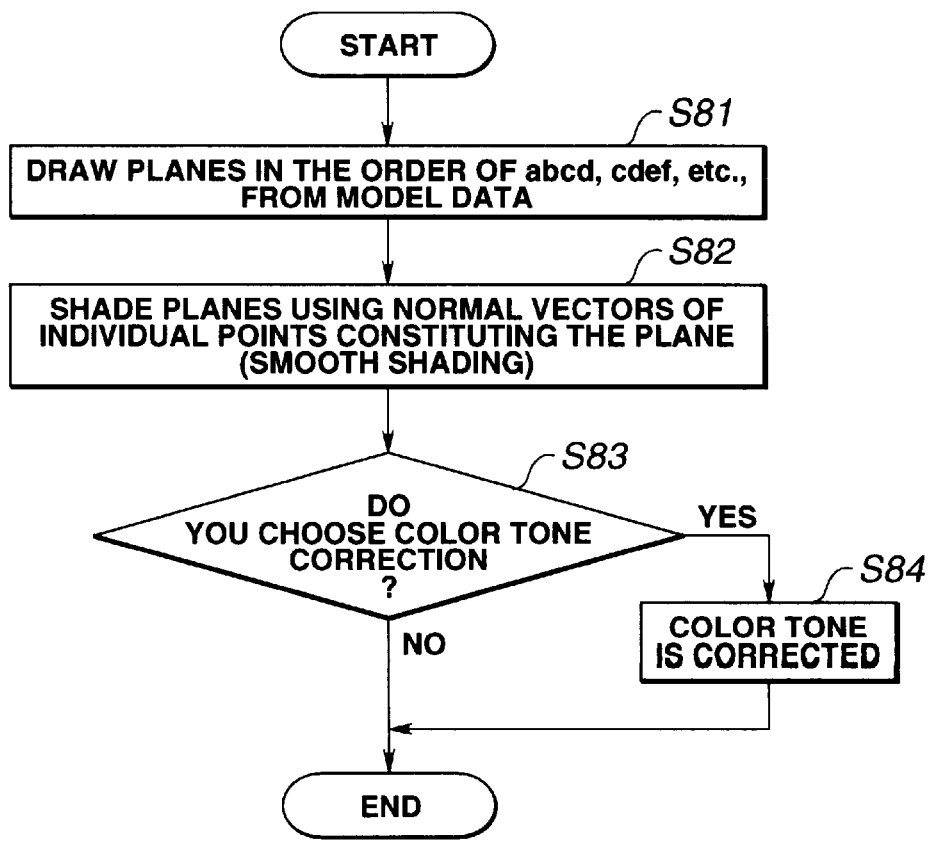
Figure 29:
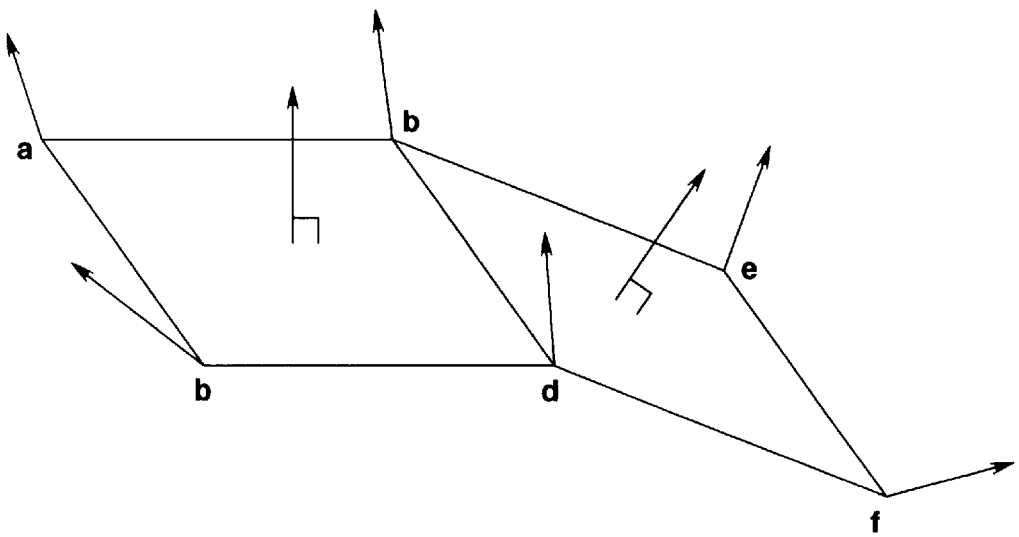

To put it more in detail, as shown in FIG. 28, CPU obtains at step S81 necessary data for reconstructing endoscope image, and constructs planes abcd, cdef, . . . , in order by referring to the data as shown in FIG. 29, and at step S82 gives appropriate shades to the planes in order according to the normal vector data (smooth shading) previously acquired. Thus, a 3D image of endoscope is reconstructed for display.

Then, CPU advances to step S83 where it checks whether color tone correction should be introduced here or not. When the screen of monitor 25 or a rectangle plane is assumed to represent an X-Y quadrant, Z-axis can be taken as representing the depth which is reproduced by an appropriate shade. CPU checks here whether color shading is applied to the image data to enhance the extension in depth of the image. When it finds color shading should be applied, it applies necessary color shading at step S84, and completes operation.

The color shading to be introduced at step S84 as needed comprises two modes: one or first type of color shading applies to the full range treated by the endoscope shape reconstructing apparatus 3, and the other or second type of color shading applies only to the range where the endoscope image exists.

Figure 30:
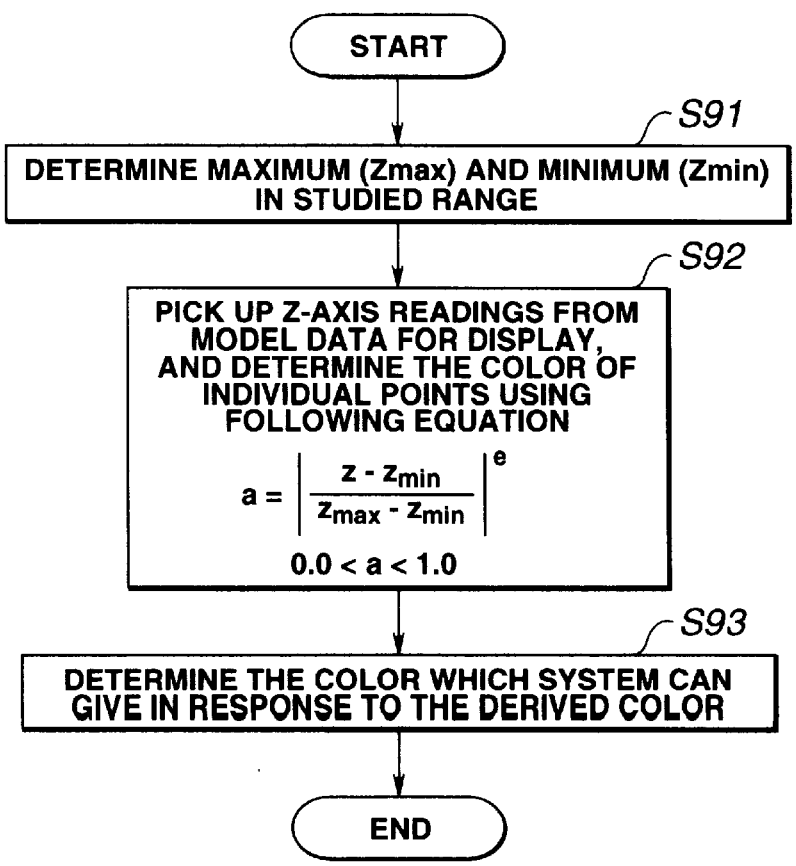
Figure 31:
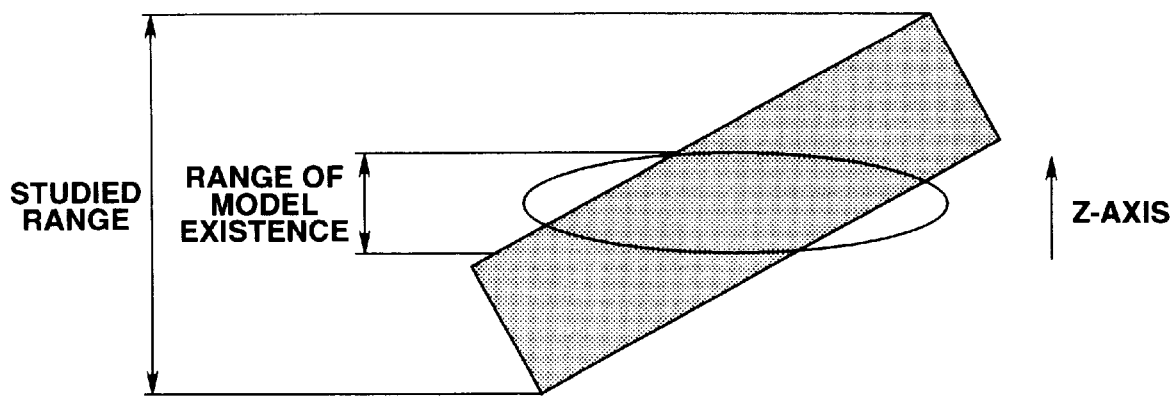

To achieve the first type of color shading, as shown in FIG. 30, CPU finds the maximum and minimum depths of the range at step S91, calculates appropriate shading to be applied to a given plane at step S92, and selects a color in stock closest to the shading and applies it to the plane at step 93. Through this operation, as shown in FIG. 31, color shading can be applied to the full range treated by the apparatus in the direction of Z-axis, or in the direction of depth.

Figure 32:
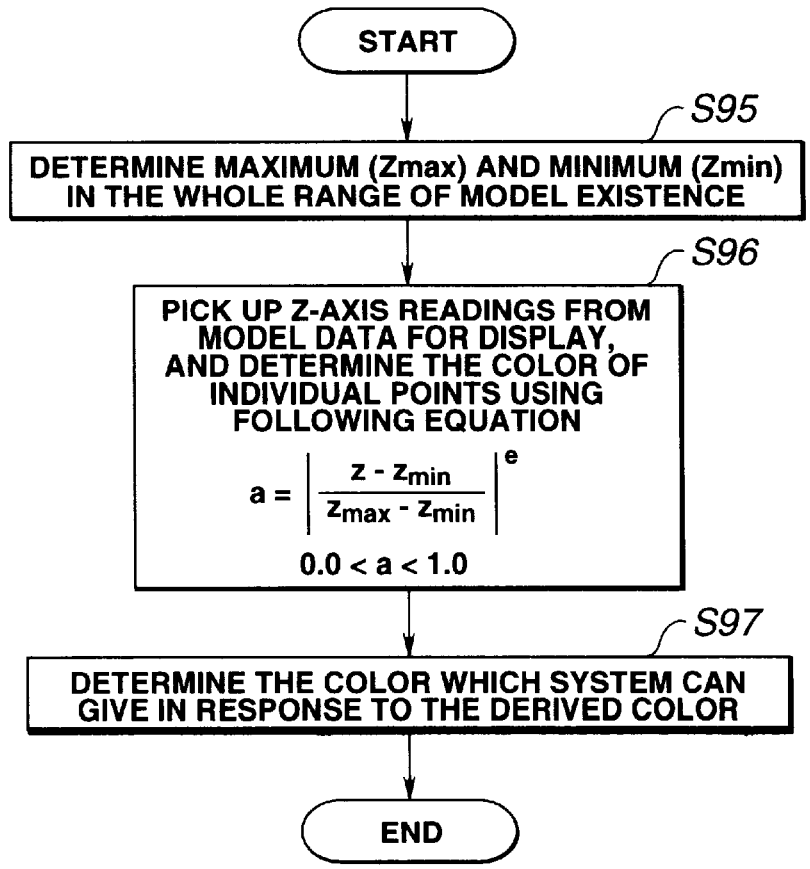
Figure 33:
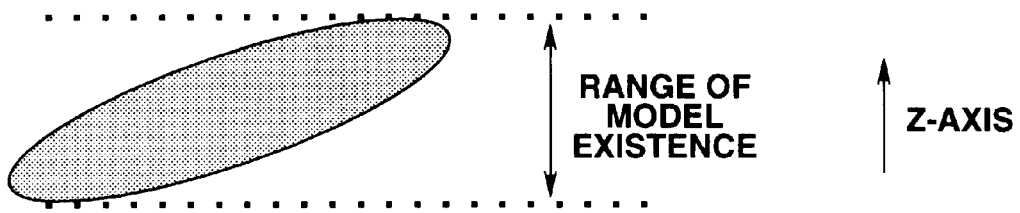

To achieve the second type of color shading, on the other hand, CPU finds, as shown in FIG. 32, the maximum and minimum depths of the range only including the endoscope image at step S95, calculates appropriate shading to be applied to a given plane at step S96, and selects a color in stock closest to the shading and applies it to the plane at step S97. This allows a color shading of endoscopic image in its full range on display as shown in FIG. 33. The second type of color shading allows a finer shading of the endoscope image in the direction of depth than does the first one.

Figure 34:
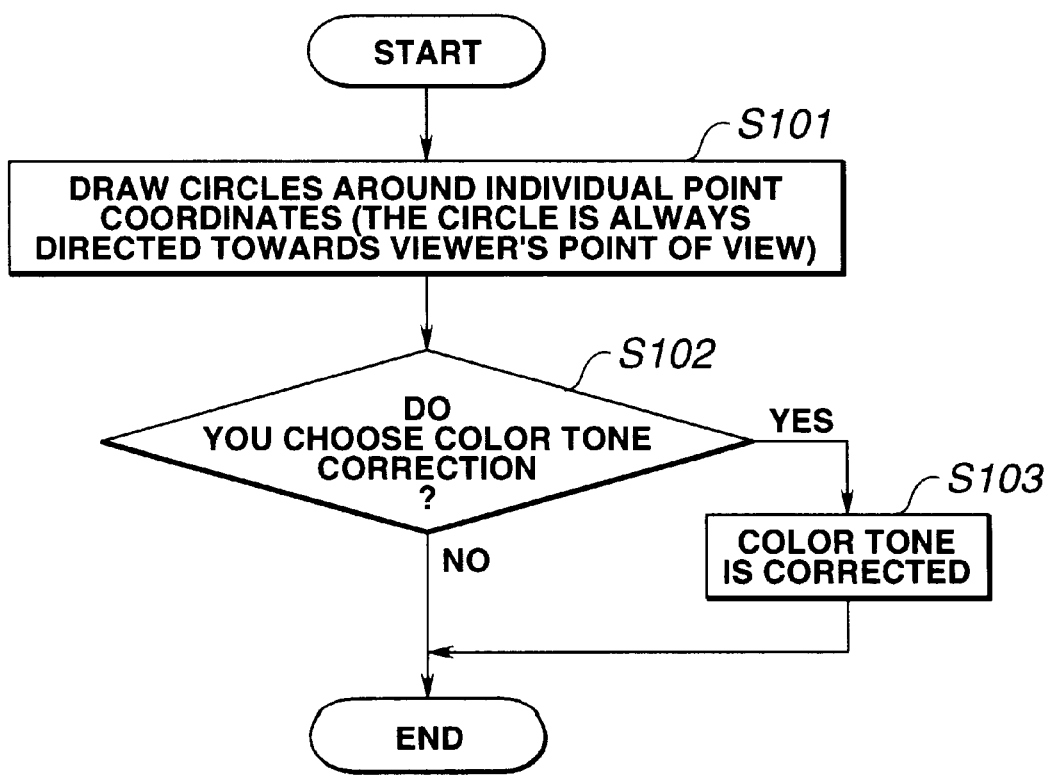
Figure 35:
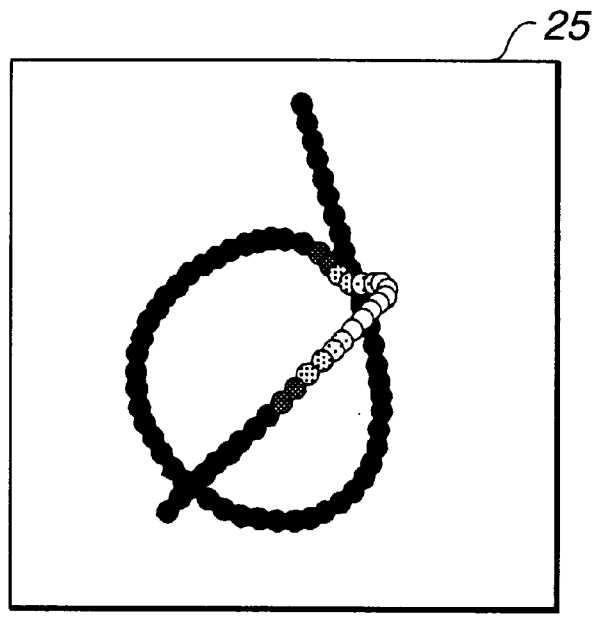

When requested of making a 2D image of endoscope, CPU draws circles (the axes of circles always direct towards the point of view of observer) around the points corresponding to the coordinates of source coils at step S101 as indicated in FIG. 34. At step S102 CPU checks whether color shading should be applied to those circles, and, when it finds color shading is necessary, it determines appropriate shading and applies it at step S103, and completes operation. Then, the observer has an image of endoscope on the monitor 25 as is illustrated in FIG. 35.

Figure 36:
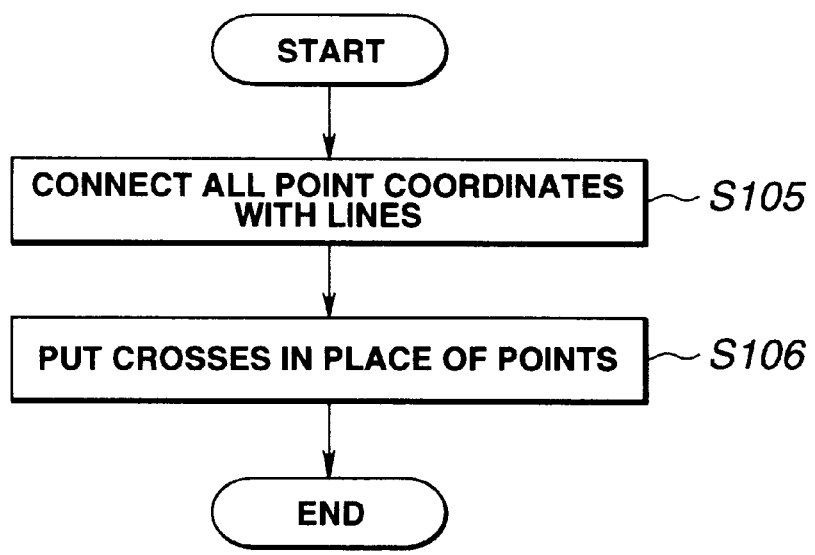
Figure 37:
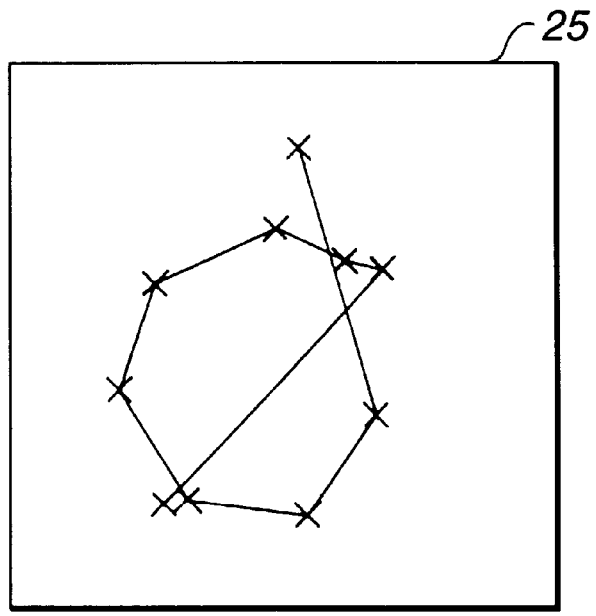

When requested of making a 12 point-in-series image of endoscope, CPU connects all the points representing source coils by straight lines at step S105 as shown in FIG. 36, places crosses on the points at step S106, and completes operation. Then, the observer has an image of endoscope on the monitor 25 as is illustrated in FIG. 37.

Figure 38:
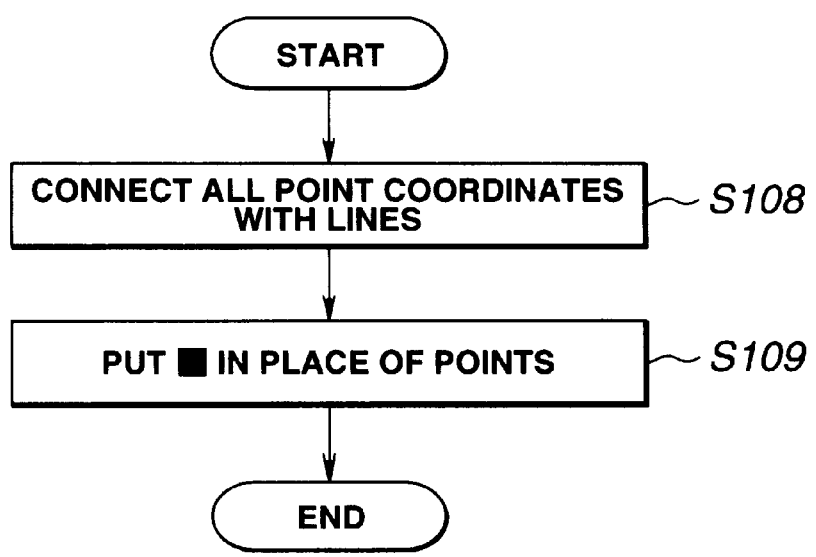
Figure 39:
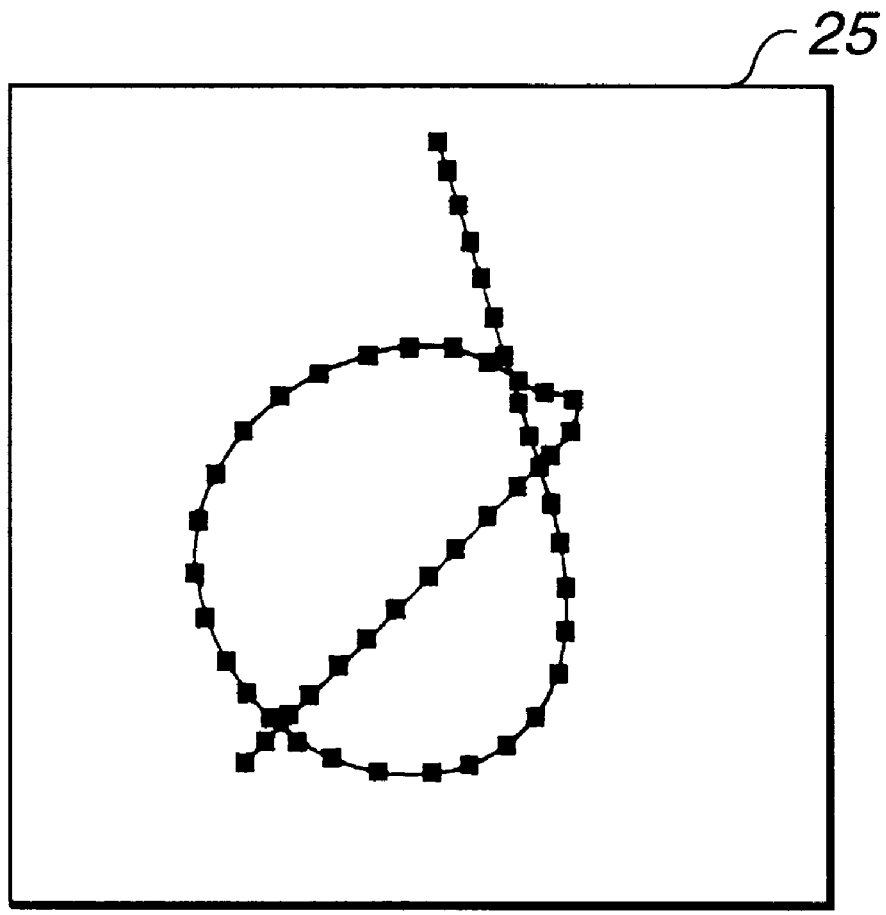

Furthermore, when requested of making a dot-line image of endoscope, CPU connects all the points representing source coils by straight lines at step S108 as shown in FIG. 38, places solid small rectangles ■ on the points at step S109, and completes operation. Then, the observer has an image of endoscope on the monitor 25 as is illustrated in FIG. 39.

(Advantage)

As is evident from above discussion, this embodiment of the invention incorporates two sensor coil sets each comprising four single core coils placed on the same line in the same direction, and allows one to locate a source coil in a 3D space by analyzing data provided by those sensor coil sets.

Further, even when the axis of source coil is normal to the plane defined by the sensor coil set and source coil, that is, even when the source coil is oriented such that it invokes no voltage in the sensor coil set, this embodiment allows one to locate that source coil.

When output from a sensor coil is very small, it is sometimes difficult to tell signal out of the sensor coil from noise. This problem, however, can be avoided after introduction of an appropriate threshold, and if signal is smaller than the threshold, it is taken to be 0. Thus, this embodiment can be applied to situations where signals are relatively small with respect to noises.

The Second Embodiment

As the second embodiment is almost the same with the first one, only different features will be outlined here and detailed description of individual elements be omitted. To elements similar in function, the same marks as those in the first one will be attached.

(Constitution)

Figure 40:
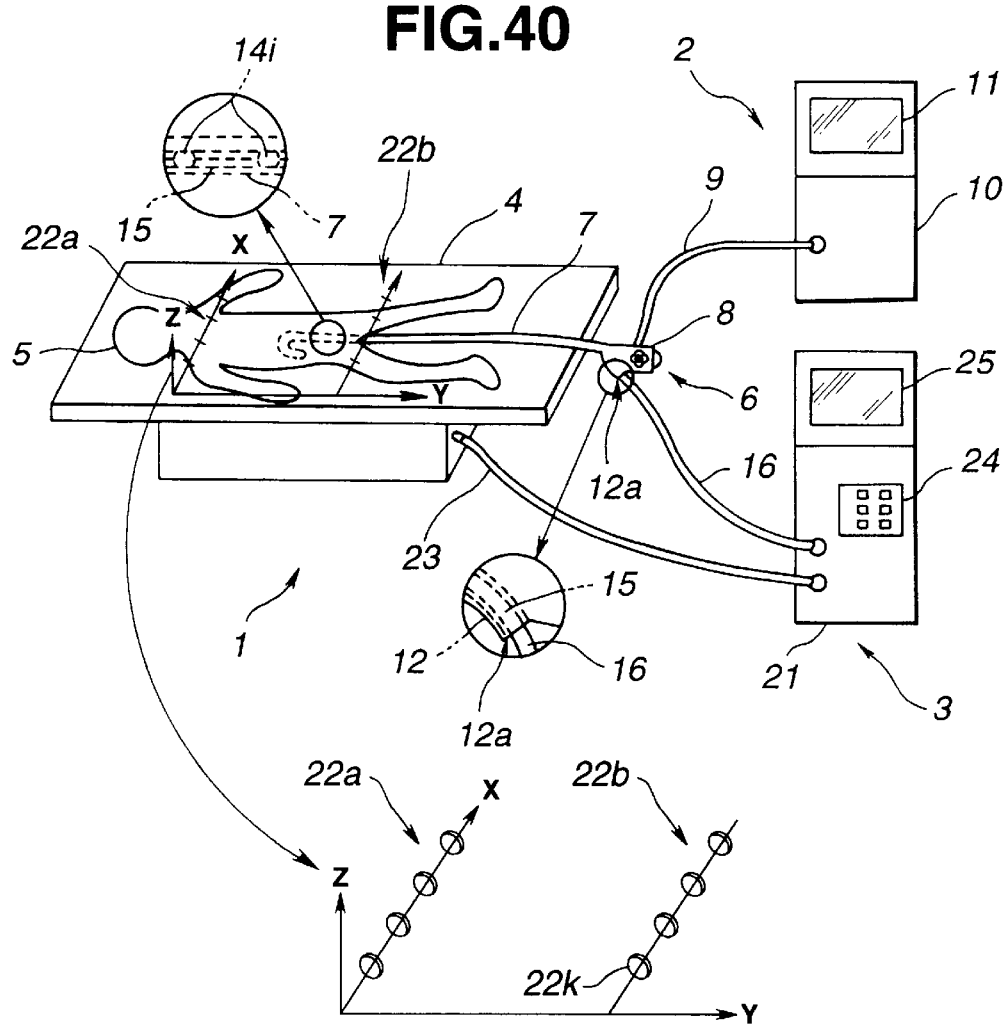
FIGS. 40–42 are related with the second embodiment of this invention.

In this embodiment, ass shown in FIG. 40, to the bed 4 where a patient 5 lies, is mounted a combination of sets of magnetism detecting elements (or sensor coils) each comprising at least four single core coils 22k which are arranged such that they stand, having a common center, on the same line facing the same direction. In this example, however, two sets of sensor coils 22a and 22b (to be represented by 22j hereinafter) run parallel to each other and are placed at respective specified positions.

Otherwise this embodiment is quite the same with the foregoing one.

(Operation)

The source coil location estimating process of this embodiment is different from that of first one.

Figure 41:
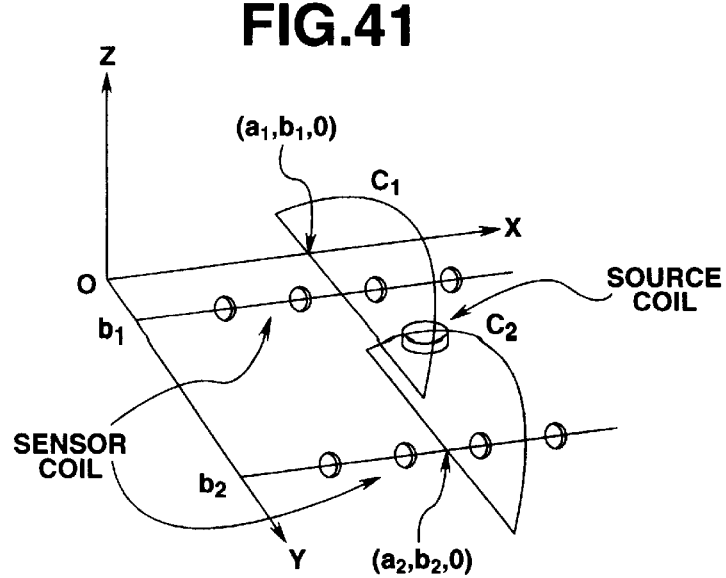

To put it more precisely, in this embodiment, as shown in FIG. 41, the system tries to locate a source coil by arranging two sets of sensor coils in parallel. The circles determined by two sets of sensor coils are termed as $C_1$ and $C_2$, and then circle $C_1$ can be expressed as $$x = a_1$$
$$y = b_1 + r_1 \cos\theta$$
$$z = r_1 \sin\theta \quad (56)$$

while circle $C_2$ as $$x = a_2$$
$$y = b_2 + r_2 \cos\phi$$
$$z = r_2 \sin\phi \quad (57)$$

When points $P_1$ ($x_1$, $y_1$, $z_1$) and $P_2$ ($x_2$, $y_2$, $z_2$) are assumed on circles $C_1$ and $C_2$, respectively, the requirement which the two point satisfy to give the shortest interval between the two circles is $$y_1 = y_2, \text{ and } z_1 = z_2 \quad (58)$$

When y1 and y2, and z1 and z2 in Equation (58) are substituted by the corresponding values in Equations (56) and (57), what results is $$b_1 + r_1 \cos\theta = b_2 + r_2 \cos\theta \quad (59)$$
$$r_1 \sin\theta = r_2 \sin\phi \quad (60)$$

When both sides of Equation (60) are squared, what results is $$r_1^2(1-\cos^2\theta) = r_2^2(1-\cos^2\phi)$$

When sin φ is isolated in Equation (59), the result is put into above equation, and θ is isolated therefrom, what results is $$\cos\theta = \frac{r_2^2 - r_1^2 - (b_1 - b_2)^2}{2r_1(b_1 - b_2)} \quad (61)$$

$$\theta = \cos^{-1}\left\{\frac{r_2^2 - r_1^2 - (b_1 - b_2)^2}{2r_1(b_1 - b_2)}\right\}$$

By putting θ value of Equation (56) into Equation (61), φ value of Equation (57) into Equation (60), and calculating $r_1$ and $r_2$ from Equation (61), we can determine the intersection ($a_1 = a_2$) of circles $C_1$ and $C_2$ or a point giving the shortest interval between the two circles.

When circles $C_1$ and $C_2$ give two points whose distance is the shortest, X-coordinate of the source coil can be determined as in the first embodiment after calculation of an average of the two X-coordinates of the two points (Y- and Z-coordinates are already given as seen from Equation (61)).

Now, the procedure how CPU 32 actually estimates the location of a source coil by the use of above method will be detailed below for illustration.

As shown in FIG. 40, two sets of sensor coils 22j each comprising four single core coils placed on the same line in the same direction are arranged parallel to each other in a bed 4. A source coil 14i comprising an array of 16 single core coils or a probe 15 is inserted through a forceps channel 13 of an electronic endoscope 6.

The endoscope shape reconstructing apparatus 3 collects voltage and phase data of potentials induced in sensor coils 22j by the array of source coils 14i, determines the polarity (whether it be positive or negative) of the maximum amplitude of evoked potentials from the corresponding phase data, and accepts maximum amplitude voltages with a polarity as outputs from the sensor coils 22j.

Then, CPU 32 executes the same procedures as in the first embodiment at steps S32 to S39, and, by processing the data thus derived by the same method as discussed earlier with reference to FIGS. 9 to 15, gives the location (on a 2D space) of a source coil on the plane determined by the sensor coil set and source coil.

Figure 42:
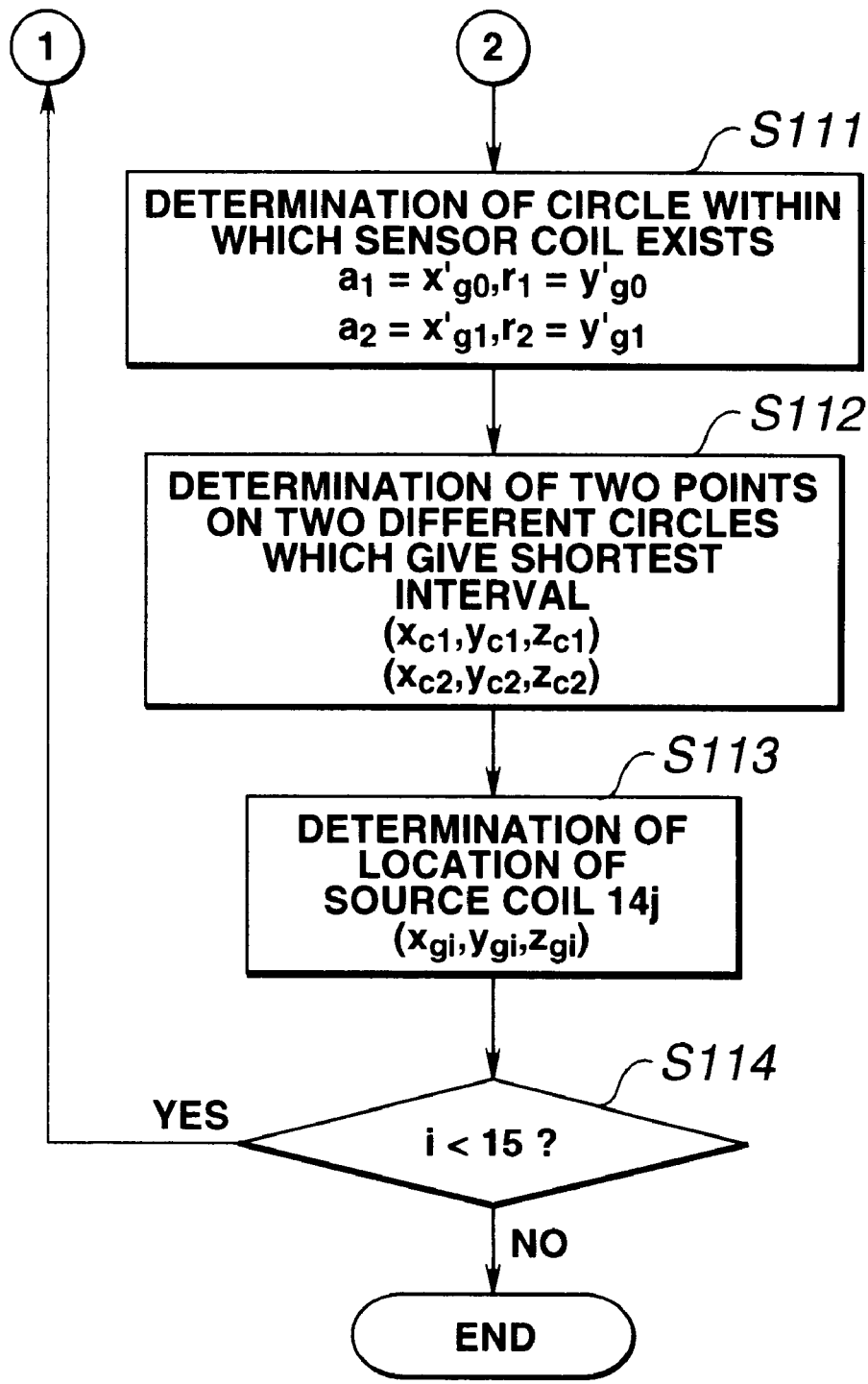

CPU 32 of this embodiment, as shown in FIG. 42, at step S111 subsequent to step S39, determines the space (circle) of each source coil from the data collected at step S38.

Then, at step S112, CPU combines two circles derived from two sets of sensor coils, and calculates two points on the two circles which give the shortest distance, and at step S113, averages the coordinates of the two points to obtain a middle point between the two, or the point where the 0th source coil exists.

At step S114, CPU checks whether the coordinates of all source coils in a 3D space have been obtained or not. When it finds i=0 here, it advances to step S47 where it increments i by one unit, returns to step S32, repeats the same processes at steps S32 to S117 of FIGS. 20 to 42, confirms at step S114 that the coordinates of the last source coil in the 3D space have been determined, and completes the processing.

Processes performed at steps S111 to S112 are a realization of the theoretical procedures discussed earlier with reference to FIG. 41.

Other effects are similar to those in the first embodiment.

(Advantage)

In addition to the effects provided by the first embodiment, this embodiment enables an estimation of the location of source coils in a 3D space by arranging two sets of sensor coils parallel to each other, each of which comprises four single core coils placed on the same line in the same direction.

The Third Embodiment

As the third embodiment is almost the same with the first one, only different features will be outlined here and detailed description of individual elements be omitted. To similar elements in function, the same marks as those in the first one will be attached.

(Constitution)

In the first embodiment, when the axis of source coil is normal to the plane determined by the sensor coil set and source coil, CPU recognizes this normality from outputs from the sensor coil set, and obtains the coordinates of the source coil by utilizing its axis being normal to the plane in question.

In reality, however, it is often difficult for CPU to judge whether outputs from the sensor coil unit are all zero or not, because signals are frequently confused with noises. Thus, the calculation based on the assumption that the axis of source coil is normal to the plane determined by sensor coil set and source coil may be misleading.

Figure 43:
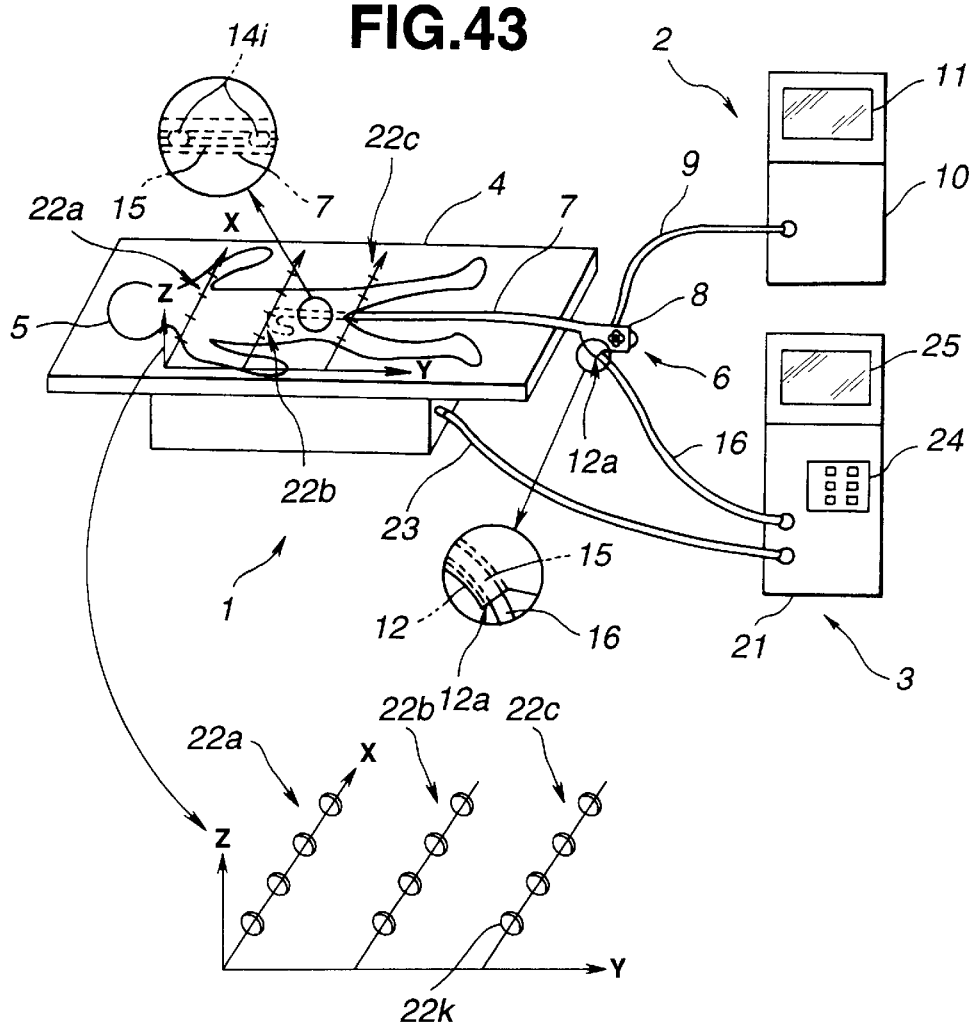
FIGS. 43–47 are related with the third embodiment of this invention.

To meet this problem, in this embodiment, as shown in FIG. 43, to the bed 4 where a patient 5 lies, is mounted a combination of sets of magnetism detecting elements (or sensor coils) each comprising at least four single core coils 22$k$ which are arranged such that they stand, having a common center, on the same line facing the same direction. In this example, however, three sets of sensor coils 22$a$, 22$b$ and 22$c$ (to be represented by 22$j$ hereinafter) run parallel to each other and are placed at specified positions.

Otherwise this embodiment is quite the same with the foregoing first one.

(Operation)

The source coil location estimating process of this embodiment is different from that of first one.

Figure 44:
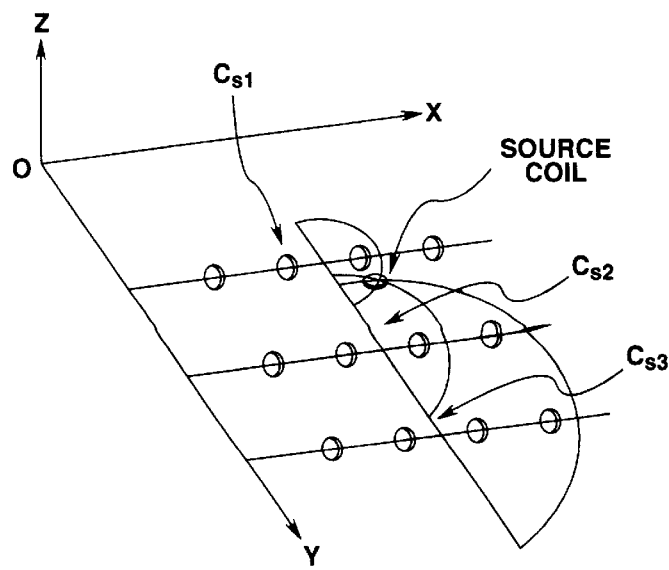

To put it more precisely, in this embodiment, the system tries to locate a source coil by arranging three sets of sensor coils in parallel, each of which comprises four single core coils placed on the same line in the same direction as shown in FIG. 44. The system combines any two sets from the three, estimates the location of source coil for each combination, gives appropriate weights to those location estimatings, and finally gets the most likely location of source coil from them.

Let's assume that the circles determined by sensor coil sets be $C_{s1}$, $C_{s2}$ and $C_{s3}$, and the coordinates of source coil determined by a combination of two circles $C_{s1}$ and $C_{s2}$ be $(x_{g1}, y_{g1}, z_{g1})$, the coordinates of source coil determined by a combination of two circles $C_{s2}$ and $C_{s3}$ be $(x_{g2}, y_{g2}, z_{g2})$, and the coordinates of source coil determined by another combination of two circles $C_{s3}$ and $C_{s1}$ be $(xg_{g3}, y_{g3}, z_{g3})$.

Let's assume further that the weights assigned to the coordinates of source coil derived from data provided by individual sensor coil sets be $w_i$ (i=1, 2, 3). Then, the coordinates $(x_g, y_g, z_g)$ of source coil can be expressed by $$x_g = \sum_{i=1}^{3} w_i x_{gi} \quad y_g = \sum_{i=1}^{3} w_i y_{gi} \quad z_g = \sum_{i=1}^{3} w_i z_{gi} \tag{62}$$

One way of weighting takes place as follows: for a given sensor coil set, outputs from four constituent single core coils are compared, and the largest output is determined as the maximum of that sensor coil set, and for the remaining two coil sets, the maxima are similarly determined. Weighting is determined according to the size of those maxima.

Let's assume that the maximum outputs of individual sensor coil sets be $V_{maxi}$ (i=1, 2, 3). Then, the weights can be expressed by $$w_1 = \frac{V_{max1}^2 V_{max2}^2}{V_{max1}^2 V_{max2}^2 + V_{max2}^2 V_{max3}^2 + V_{max3}^2 V_{max1}^2} \tag{63}$$

$$w_2 = \frac{V_{max2}^2 V_{max3}^2}{V_{max1}^2 V_{max2}^2 + V_{max2}^2 V_{max3}^2 + V_{max3}^2 V_{max1}^2}$$

$$w_3 = \frac{V_{max3}^2 V_{max1}^2}{V_{max1}^2 V_{max2}^2 + V_{max2}^2 V_{max3}^2 + V_{max3}^2 V_{max1}^2}$$

From Equation (17), gy and gx are determined by the angle the axis of source coil has with respect to the plane which is determined by a sensor coil set and source coil. Thus, $$g_{xyi} = g^2_{xi} + g^2_{yi}$$

(i=1, 2, 3)

is calculated for each sensor coil set, and $V_{maxi}$ in Equation (63) may be substituted by gxyi in above equation.

Now, the procedure how CPU 32 actually estimates the location of a source coil by the use of above method will be detailed below for illustration.

As shown in FIG. 43, three sets of sensor coils 22$j$ each comprising four single core coils placed on the same line in the same direction are arranged parallel to each other in a bed 4. A source coil 14$i$ comprising an array of 16 single core coils or a probe 15 is inserted through a forceps channel 12 of an electronic endoscope 6.

The endoscope shape reconstructing apparatus 3 collects voltage and phase data of potentials induced in sensor coils 22$j$ by the array of source coils 14$i$, determines the polarity (whether it be positive or negative) of the maximum amplitude of evoked potentials from the corresponding phase data, and accepts maximum amplitude voltages with a polarity as outputs from the sensor coils 22$j$.

Figure 45:
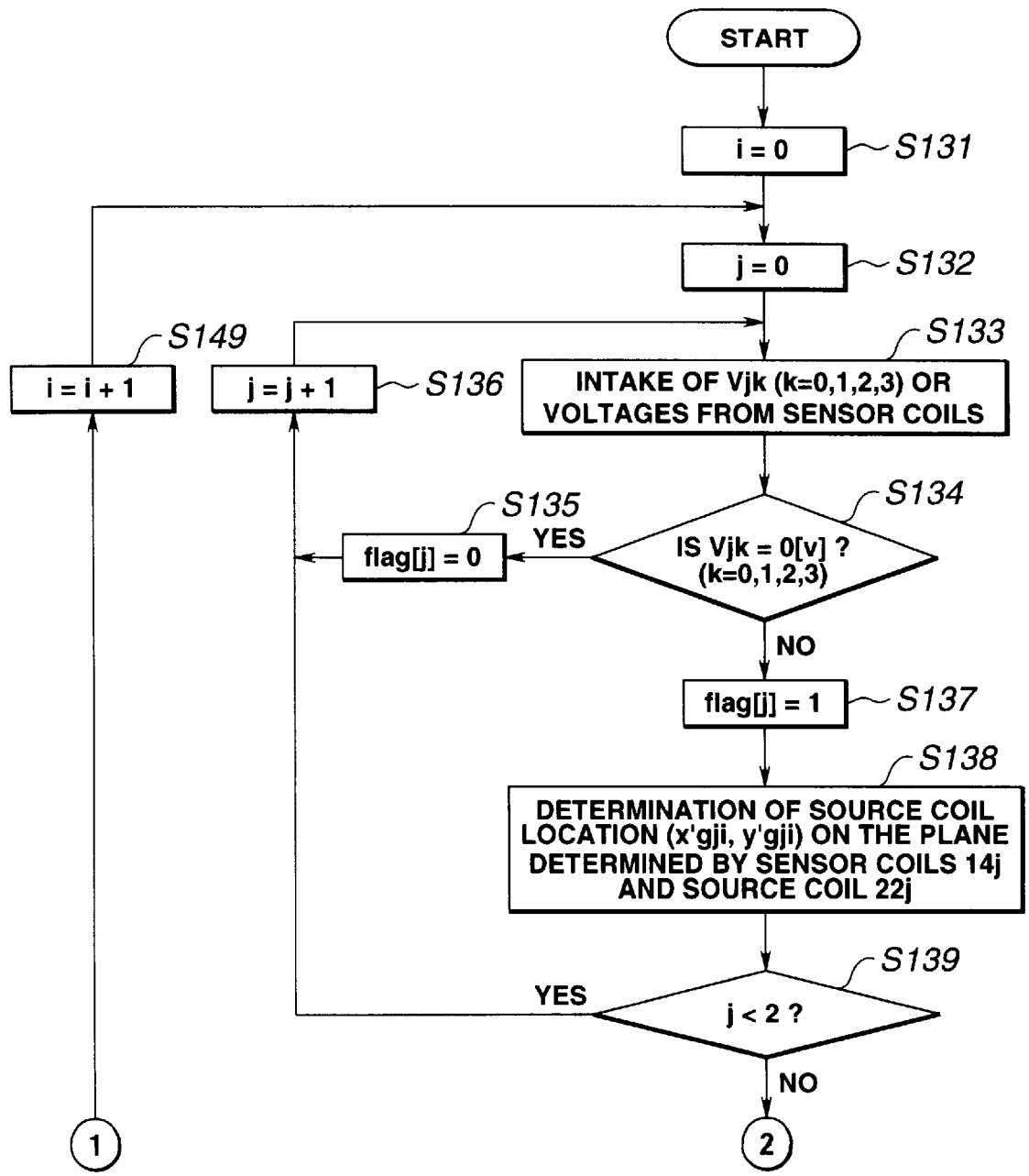

To put it more specifically, as shown in FIG. 45, CPU 32 firstly initializes the order of source coils 14$i$ and sensor coils 22$j$ to be processed at steps S131 and S132. Thus, it sets i=0 at step S131 and j=0 at step S132.

Firstly, 0th source coil and 0th sensor coil are picked up for processing: at step S133, voltages $V_{00}$, $V_{01}$, $V_{02}$ and $V_{03}$ induced in the four single core coils constituting the 0th sensor coil set are collected. The voltages collected at step S133 are transmitted to step S134 where they are checked for their being 0[V] or not.

When at step S134 all the voltages $V_{00}$, $V_{01}$, $V_{02}$ and $V_{03}$ from the four single core coils constituting the 0th sensor coil set are found to be 0[V], it indicates that the axis of 0th source coil is normal to the plane determined by the 0th sensor coil set and 0th source coil. When CPU meets this situation, it advances to step S135, sets the flag of 0th sensor coil set to 0, advances to step S136 where it increments j by one unit, and returns to step S133 to proceed to the processing of 1st sensor coil set.

When at step S134 CPU finds that all the voltages $V_{00}$, $V_{01}$, $V_{02}$ and $V_{03}$ provided by four single core coils constituting the sensor coil set are not 0[V], it advances to step S137 where it sets the flag of 0th sensor coil set to 1.

Then, at step S138, CPU determines the coordinates $(x'_{g00}, y'_{g00})$ of 0th source coil on the plane determined by 0th sensor coil set and 0th source coil.

At step S139, CPU checks whether outputs from 0th and 1st sensor coil sets have been processed to give 2D coordinates of 0th source coil. At this step when it finds j=0, it recognizes that processing of outputs from 1st sensor coil set is not yet done to give 2D coordinates of 0th source coil. Then, it advances to step S136 where it increments j by one unit, and returns to step S133 where it starts to process outputs from 1st sensor coil set.

CPU exercises the same processing at steps S133 to S138 as was discussed earlier. Because j remains to be unit (j=1) throughout this operation, CPU returns to step S136, increments J by one unit, comes back to step S133 where it processes the data from first sensor coil set, and executes the same processes at steps S133 to S138 as discussed earlier.

Now that j=2, CPU confirms at step S139 that processing of outputs from 0th, 1st and 2nd sensor coil sets is completed and it obtains three 2D coordinates $(x'_{g00}, y'_{g00})$, $(x'_{g10}, y'_{g10})$ and $(x'_{g20}, y'_{g20})$ of 0th source coil.

Figure 46:
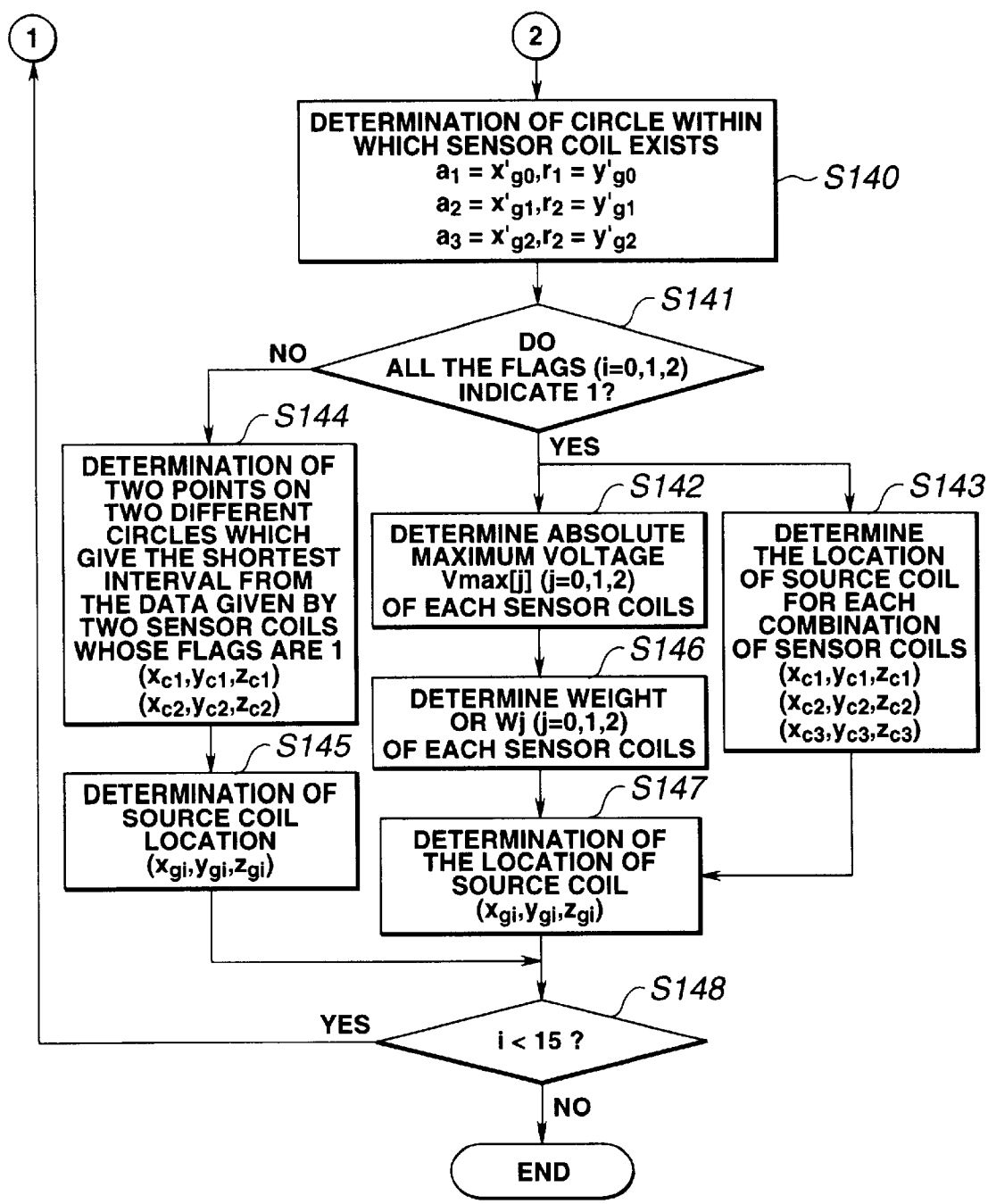

After confirming at step S139 outputs from 0th, 1st and 2nd sensor coil sets are processed to give three 2D coordinates $(x'_{g00}, y'_{g00})$, $(x'_{g10}, y'_{g10})$ and $(x'_{g20}, y'_{g20})$ of 0th source coil, CPU advances to step S140 of FIG. 46 where it determines the space (circle) of the source coil under study from the data of 2D coordinates collected at step S138.

CPU checks at step S141 whether given 2D coordinates suggest that the axis of source coil in question is normal to the plane determined by the sensor coil set and source coil. When it finds that all three coordinates suggest that the axis of source coil is not normal to the coil plane, it advances to steps S142 and 143. Otherwise it advances to step S144 (the axis of source coil can not be normal to two or more sensor coil units.)

At step S141, CPU checks whether all flags are unit or not. When it finds one of them is not unit, it recognizes that the axis of source coil is normal to the plane determined by source coil and sensor coil set whose flag is not unit. Thus, at step S144, CPU picks up two sensor coil sets other than the one whose flag is not unit, and determines two points on the two circles which have been provided by the two sensor coil sets that give the shortest interval.

At step S145, the coordinates of the two points are averaged to give a location of the source coil in a 3D space. Thus, the location, for example, of 0th source coil is determined.

When CPU finds at step S141 that the flags of sensor coil sets are all unit, it advances to step S142 where it determines the absolute maximum voltage of each sensor coil set, and advances to step S146 where it calculates the weight according to the maximum of each sensor coil set (Equation (63)). At step S143, CPU collects 2D coordinate data of 0th source coil provided by three sensor coil sets, and determines its 3D coordinates for every combination of the sensor coil sets.

Then by combining weights obtained at step S146 and the 3D coordinate data obtained at step S143, CPU determines the likeliest location of source coil in the 3D space at step S147 (Equation (62)).

At step S148, CPU checks whether the coordinate data for the 3D space have been properly processed for all the source coils or not. When it finds data for one source coil are not yet properly processed, it returns to step S149 of FIG. 45 where it increments i by one unit, repeats the same processes until all relevant data are properly processed. Thus, after confirming at step S148 that the coordinates of the last source coil in the 3D space have been determined, CPU completes the processing.

Other effects are similar to those in the first embodiment.
(Advantage)

As is evident from above discussion, in addition to the effects provided by the first embodiment, this embodiment enables an exact estimation of the location of source coils in a 3D space comparatively uninfluenced from the effects of surrounding noises, because, in a circumstance where the axis of a source coil is nearly normal to the plane determined by sensor coil set and source coil, and thus the voltage induced in the sensor coil set by the source coil is so small in magnitude that it is scarcely distinguishable from noises, which may lead to wrong estimation of the location of source coil, this embodiment, before calculating 3D coordinates of the source coil, gives a smaller weight to the output which is too small to be distinguished from noises and a larger weight to the output which is sufficiently large to be easily distinguishable from noises.

Figure 47:
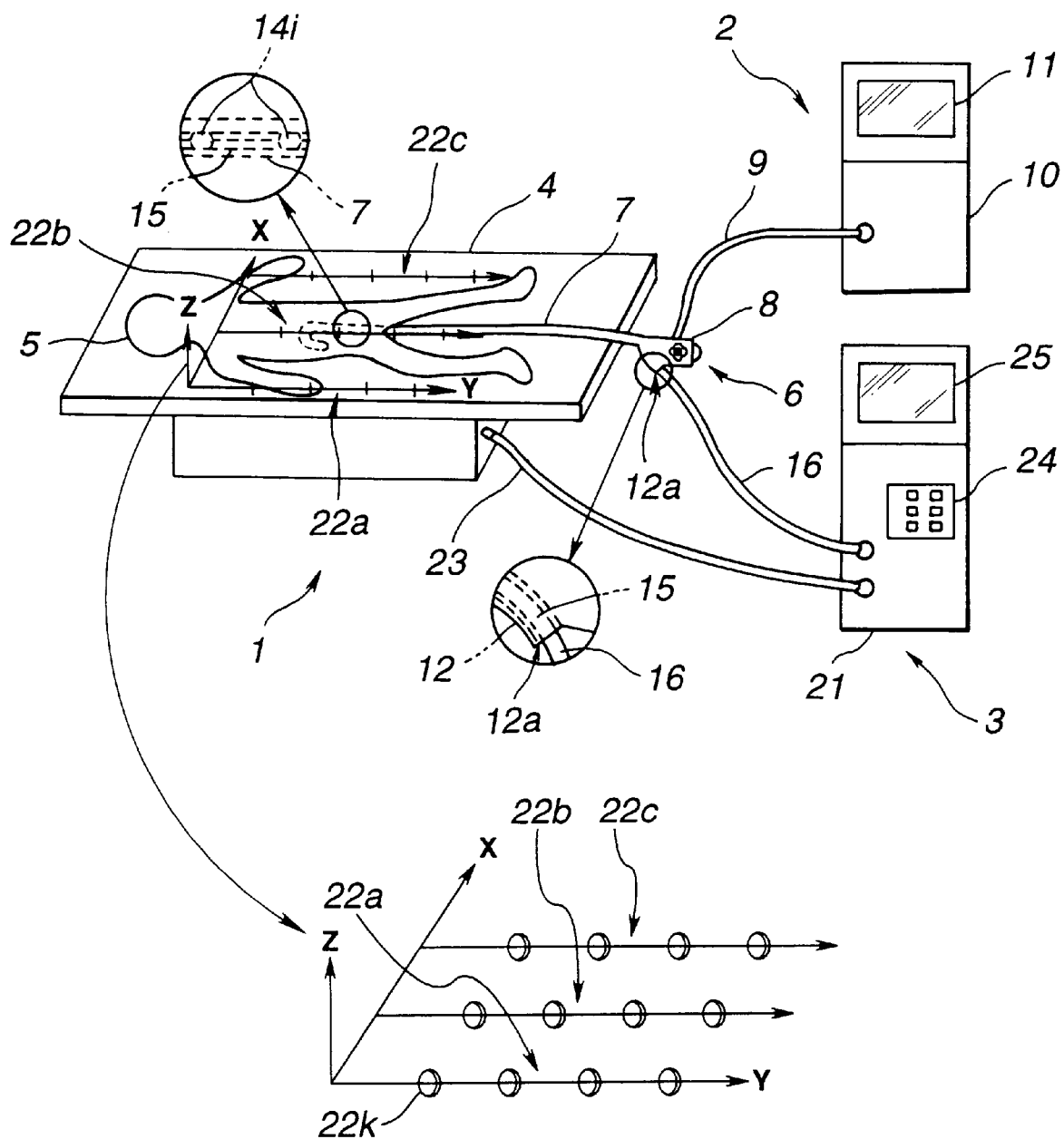

In this embodiment, as shown in FIG. 43, three sensor coil sets 22j are arranged in parallel in a bed 4 where a patient 5 lies, but, as shown in FIG. 47, these sensor coils may be arranged on axes normal to those of the sensor coil sets depicted in FIG. 43, and at specified positions along the axes which run parallel to the long axis of bed 4 where the patient 5 rests.

In above embodiments, two or three sensor coil sets each comprising four single axis coils are combined, and the voltages in the individual sensor coils induced by the source coil are collected and analyzed to provide the location of source coil. On the contrary, two or three sensor coil sets (actually source coils in this case) each comprising four single axis coils may be allowed to generate magnetic fields one after another, and the induced voltages in the source coil (actually sensor coil in this case) therewith may be collected and analyzed to give the location of that source coil. This method also requires the same operation and ensures the same advantages with the previous ones.

Generally, the apparatus to reproduce an endoscope image must be provided with magnetism generating coils and magnetism detecting coils which serve for locating an endoscope inserted into the body by estimating the coordinates of endoscope in a 3D space.

Accordingly, an endoscope is generally used in combination with a probe which can be inserted into the insert of scope, or into a channel for the passage of treatment tools, and incorporates an array of coils within its space.

In such constitution, it is necessary to combine a wire to make a magnetic coil and another wire to transmit electric signals into a coil unit. If this connection were achieved by soldering, the resulting connection would be so brittle and fragile to bends as to be easily disconnected, because the solder blot developed at the connection is very hard. This would make it impossible for the coil unit to act as an aid for locating the endoscope or reproducing endoscope image.

If the connection were achieved by pressure bonding instead of soldering, the connected part would be too stiff to be smoothly bent even though it would not be so brittle as the soldered connection, and this stiffness would almost incapacitate the function of probe because the addition of metal connections resistive to bending to an array of coils which are also stiff themselves would increase the stiffness of the whole probe assembly so much that the insertion of probe into a sinuous body cavity and v handling of treatment tools there would be nearly impossible.

One wire to make a coil and the other to transmit signals may be united into one, instead of being prepared separately, but such coil made of a single wire acting as a magnetic coil and signal transmitter at the same time becomes very complicated in structure, requires intricate works, and thus reduces productivity: winding the wire around a core becomes cumbersome, and it is necessary to twist the wire segment for signal transmission after the coil segment has been completed, in order to suppress unnecessary generation of magnetic fields.

Thus, currently a demand is manifest for a method whereby a coil wire and a signal transmitting wire are connected so smoothly and securely as to be resistive to mechanical impacts.

To meet such demand, the present inventors propose here an endoscope locating coil apparatus which is inserted into body to determine the shape or location of an endoscope by utilizing magnetism, and which is resistive to bends during use, being resilient against strains and tears, and durable to long use.

Another object of this invention is to provide a method of producing an endoscope locating coil apparatus which can alleviate, as much as possible, damaging effects inflicted by bends of the endoscope tip.

The embodiments of this invention will be described in detail below with reference to attached figures.

The Fourth Embodiment

The probe apparatus for reproducing endoscope image (to be referred to briefly as probe apparatus hereinafter) 201 as shown in FIG. 48 consists of a sheath 202 and a plurality of endoscope locating coil apparatuses (coil apparatuses) 203: the sheath 202, being flexible and tubular in form, is inserted, for example, into a forceps channel of an endoscope not illustrated here when the endoscope is inserted into a bodily cavity, and is fixed with a fitting to that channel, and the coil apparatuses 203 are bonded with an adhesive to rod-like interconnecting members 204 to form an array of coil apparatuses with an interval of d between each other and placed along the long axis of probe apparatus (d may be constant, or varied from one interval to another as long as d has been known by some means.)

The interconnecting member 204 is made of an elastic, slender wire-like material so that it may not interfere with bending operations or flexible characteristics of the endoscope tip when the probe is inserted into one of the channels of that endoscope.

The interconnecting member 204 is preferably made of a highly elastic material that contracts little when pressed lengthwise, and is resilient to bending forces, because an interconnecting member with this property, when incorporated into a probe apparatus, will allow a force applied lengthwise to be transmitted securely to the tip of probe. For this purpose, highly elastic metals such as nitinol are appropriate.

Figure 49:
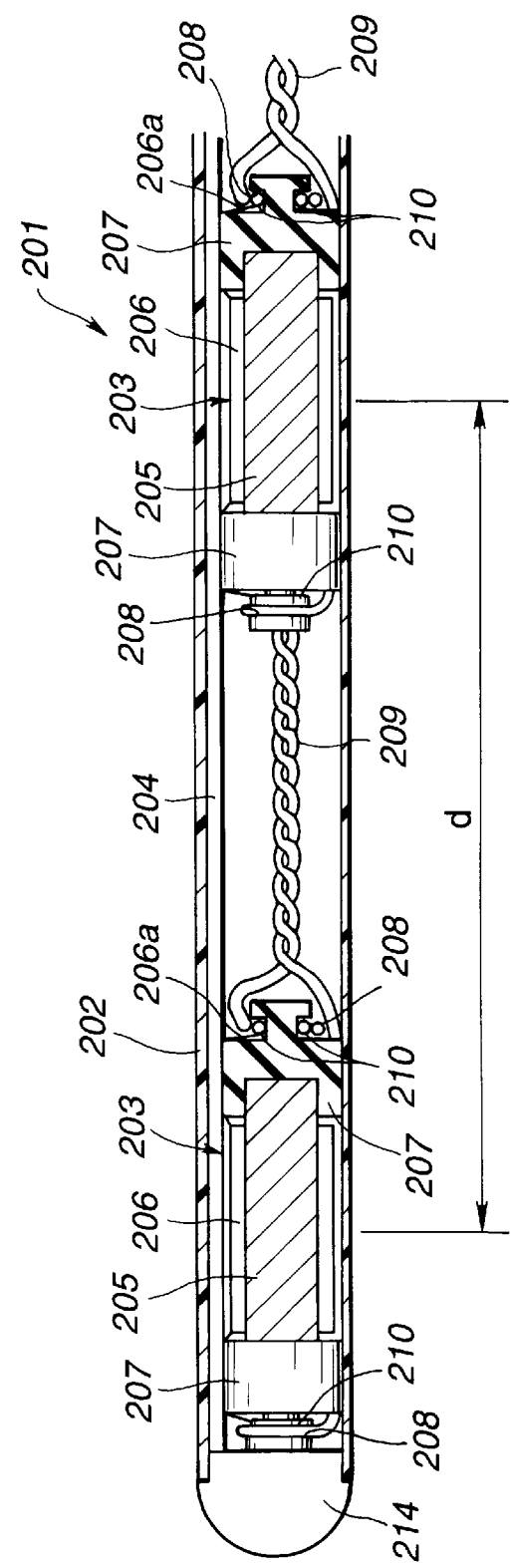
Figure 50A:
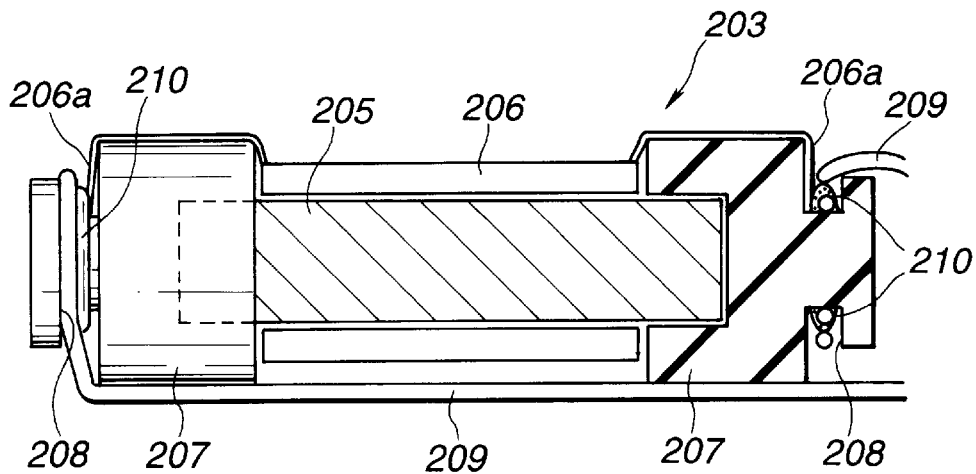
FIG. 50(A) gives a lateral view of a coil apparatus which is partly cross-sectioned for illustration and which is a part of the endoscope system of the fourth embodiment.
Figure 50B:
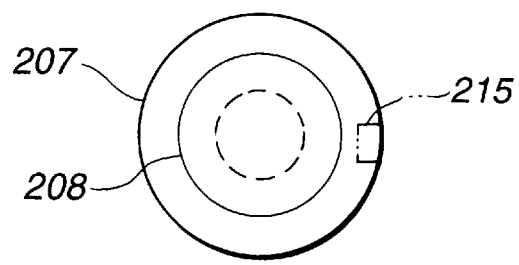
FIG. 50(B) gives an left end view of the coil apparatus of FIG. 50(A) which shows the connector part of the apparatus.

As shown in FIGS. 49, 50(A) and 50(B), a coil apparatus 203 consists of a tubular core 205 made of a hard material, a coil 206 which is formed after an insulated thin wire such as copper wire has been wound around the core 205, and connecting members 207 made of a hard, non-conductive (insulating) material bonded to the ends of an adjacent core 205 supporting the coil 206.

The core 205 is preferably made of a material with a high magnetic permeability such as permalloy so that it may develop a magnetic field efficiently.

A connecting member 207 is nearly columnar in form, and has one end pitted at the center to form a depression to receive a core 205, and the other end so prepared as to form a concentric groove 208 which acts as a fixing (holding) section: this section not only serves as a place where ends of coils 206 are electrically connected with the corresponding ends of signal transmitting cables 209 by soldering, but prevents external forces from directly affecting those connections 210.

The end of connecting member 207 continuous with the concentric groove 208 forms a concentric circle with a smaller diameter, and thus, as seen from FIG. 49, the groove 208 can accommodate signal transmitting cables 209 therein without requiring enlargement of the inner diameter of sheath 202, and helps the signal transmitting cable whose one end is connected to the end of a coil 206 to be easily extend beyond the groove's edge to an inter-coil space.

The connecting member 207 has a slightly larger outer diameter than does the coil 206 wound around the core 205, and thus the outer rim of connecting member extends beyond that of coil. This arrangement permits the connecting member 207 to protect the coil 206 against external mechanical shocks.

The signal transmitting cable 209 to be connected to the coil apparatus 203 is inserted into the sheath 203, and its proximal end is connected through a stiff segment 211 to a connector 212 at the proximal end of probe apparatus 201.

The connector 212 is covered with a water-proof cap as appropriate which facilitates disinfecting or sterilizing treatment of the apparatus. The distal end of probe apparatus 201 is closed with a tip member 214 having a hemispherical form.

The connector 212 can be reversibly connected to an endoscope shape reconstructing apparatus not illustrated here which is responsible for reproducing the image of endoscope. Through this connection following events occur in succession to produce the desired result: a driving signal generating circuit in the endoscope image reconstructing apparatus dispatches AC driving signals, which are then delivered through signal transmitting cables 209 to individual coil apparatuses 203 to activate those coils to generate magnetic fields around them. Thus, the coil apparatuses 203 act as source coils.

The magnetic field generated by each coil apparatus 203 is detected by a plurality of sensor coils for detecting magnetic fields which are placed at specified positions (known positions), for example, at a corner of bed, the signals therefrom are delivered to a source coil locating section which gives an estimate as to 3D locations of the coil apparatuses.

As shown in FIG. 49, the plurality of coil apparatuses 203 are arranged along the long axis of probe apparatus 201, being connected to each other with interconnecting members 204 with a specified interval d between adjacent coil apparatuses. This arrangement of coil apparatuses 203 allows reproduction of the images of those coils in a 3D space after a series of analysis processes. Thus, the image of the insert of endoscope into which the probe apparatuses have been inserted can be reproduced and is displayed on a monitor.

The probe apparatus 201 can be utilized as a sensor of magnetic field, instead of a generator of magnetic field. In this case, the plurality of coils placed at specified positions are utilized as source coils. Then, driving signals are applied in succession to those source coils to excite them to generate magnetic fields; the signals are then recorded by the coil apparatuses 203 placed within the probe apparatus 201; the recorded data of magnetic fields are delivered through signal transmitting cables 209 to a coil locating section; the coil locating section analyzes those data to derive the amplitude and phase of individual signal waves, compares the amplitude and phase data with the corresponding specified positions of the responsible sensor coils, and gives an estimation of the location of individual coil apparatuses 203 or sensor coils in a 3D space. This method further allows one to monitor the insert of endoscope in the body.

In the coil apparatus 203 of this embodiment, as shown in FIG. 49 or FIG. 50(A), the core 205 around which wire has been wound to form the coil 206 has the connecting members 207 made of an insulating material at both ends, and each connecting member 207 has a concentric groove 208 on one end.

The concentric groove 208 allows electric connections to be established there in an easy but secure way: one proximal end 206a of wire wound around the core to form the coil 206 is stripped of insulating coat to be a bare conductive segment (lead segment), this lead segment is wound around the concentric groove 208 by at least one turn and its position is adjusted so as to ease soldering, one distal end of the signal transmitting cable 209 to be inserted into the probe apparatus 201 in the direction of the long axis is similarly stripped of its insulating coat to be a bare conductive segment, the lead segment thus obtained is wound around the same concentric groove 208 by at least one turn close to the foregoing lead segment, electrically conductive molten alloy is applied with a soldering tool onto the two lead segments wound around and securely attached to the groove 208, and thus a secure electrical connection is established by soldering between the two lead segments.

The lead segment of signal transmitting cable 209 is further wound over the connecting section 210 by at least one turn, thereby reinforcing the latter.

The lead segment 206a and lead segment from the signal transmitting cable 209 may be laid one over the other to form an electrical connection, over which the elastic lead segment of signal transmitting cable 209 is wound by at least one turn, to strengthen the connection mechanically.

To put it into practice, it is necessary for the concentric groove 208 to have a sufficient depth to accommodate particularly turns of the lead segment of signal transmitting cable 209 in its space, because the signal transmitting cable has a far larger size than the coil wire (at least as far as their bare segments are concerned.) Further, the concentric groove 208 preferably has a sufficient depth to allow molten alloy to cover not only the top surface but also the under surface of groove, because such construction of groove will allow an easier and securer soldering.

The lead segment 206a and signal transmitting cable 209 may be soldered for connection at a part between the end of coil and the connecting member 207, and the bare segment of signal transmitting cable 209 may be wound around the groove 208 of connecting member.

The coil apparatus 203 is produced, for example, by a following method: a wire is wound around a hard core to form a coil which is used to generate or record a magnetic field; connecting members made of a hard and non-electroconductive material each with a groove 208 at one end to receive the lead segments of coil wire 206 and signal transmitting cable 209 around its circumference, are bonded to both ends of core 205; the lead segments of coil wire 206 and signal transmitting cable 209 are wound around the groove 208 and united firmly by soldering to form the connection 210 on the surface of groove 208; and the extra lead segment of signal transmitting cable 209 is further wound around the groove by about one turn to reinforce the connection 210 (not being hardened with solder).

As the connection 210 is firmly established at the groove 208 prepared at the end of connecting member 207 made of a hard material (sufficiently hard not to deform in the presence of bending forces), it is protected from external forces. Thus, even though the probe apparatus 201 is bent and a bending force is transmitted to a coil apparatus 203, that force is received by the connecting member 207 before it reaches the connection 210, and the connecting member 207 is made of a material sufficiently hard to resist deformation.

Even though an external force is applied to the groove portion which is not covered with solder and thus is not hardened, the lead segment of signal transmitting wire 209 wound around that portion is so elastic as to resist tears and breakage due to such external forces.

As shown in FIG. 49, in this embodiment, the probe apparatus 201 contains an array of coil apparatuses 203 in the direction of long axis, and, in addition, the corresponding number of signal transmitting cables inserted through the sheath 202 which are to deliver driving signals to excite the coil apparatuses 203, or to transmit sensor signals received by the coil apparatuses 203. A pair of two signal transmitting cables 209 is connected to each coil apparatus 203. The signal transmitting cables 209 are bonded with an adhesive to the sides of coil apparatus 203.

Further, as shown in FIG. 49, a pair of signal transmitting cables 209 to be connected to a given coil 206 are twisted together to prevent unnecessary electrical irradiation.

A pair of twisted cables as shown in FIG. 49 are stretched in a space between adjacent coil apparatuses 203 with a sufficient slackness to comply with bends and twists of that space: the slackened cables can easily deform according to the force applied from outside, and thus they are resistive to damaging effects of external forces such as tension (more resistive than similar cables which are tautly stretched and have no such slackness)

Pairs of two signal transmitting cables 209 are connected to coil apparatuses 203, but the pairs may share one common signal cable 290, and the other members of the pairs may be different from each other.

A wire is turned round into a solenoid to form a coil 206. During this process, the wire may be coated with an insulating adhesive to strengthen the coil 206 so much as to be resistive to mechanical deformations, or the coil 206 may be provided with a protective membrane.

A pair of signal transmitting cables 209 are twisted into a cord. During this process, the ends of cables may be devoid of twists and the straight lead segments may be fixed to the sides of coil apparatuses 203 to minimize the size of cables there.

The operation of a coil apparatus 203 with above constitution will be given below. When an endoscope is introduced into a sinuous bodily cavity, the introduction will be more smoothly and safely achieved with the endoscope which allows one to monitor the manner how the endoscope is advanced in the cavity than with the endoscope with no such property.

To achieve such monitoring, a probe apparatus 201 is introduced into, for example, a channel for insertion of treatment tools of the endoscope until its distal end reaches the distal tip of that channel. The connector 212 of probe apparatus 201 is connected to an endoscope image reconstructing apparatus.

When an array of coil apparatuses 203 are used as source coils, AC driving signal currents are delivered through signal transmitting cables 209 to those coil apparatuses one after another, to excite those coils to generate magnetic fields around them. The magnetic fields evoke voltages in sensor coils placed at specified positions, which are then analyzed into amplitude and phase data. These data are used to estimate the location of individual coil apparatuses 203 in a 3D space, and the endoscope image reproduced from the location data of individual coil apparatuses is displayed on a monitor. The operator, by referring to the endoscope image on the monitor, can smoothly and safely insert the endoscope even through a sinuous bodily cavity until it reaches the site to be examined.

When the insert of an endoscope is inserted through a sinuous cavity, the probe apparatus placed in the insert is also flexed and bent. It further undergoes a flexion at the curved section of endoscope. Thus there are forces within the probe apparatus 201 which tend to deform the coil apparatuses 203 placed within the probe apparatus 201 and to stretch the signal transmitting cables 209 placed in the inter-coil spaces within the probe apparatus 201.

The coil apparatus 203 contains a core 205 and connecting members 207 both of which are made of elastic materials, and thus, even when deforming forces are applied to the coil apparatus 203, those forces are absorbed by the core 205 and connecting members 207. This arrangement protects the coil 206 and a wound wire constituting the coil, and the connection 210 from such deforming forces.

When the insert is flexed and a tensile force is applied to stretch the signal transmitting cables 209, the signal cables are fixed through slackened segments to the connections 210, and thus absorb the tension by deforming these slackened segments in accordance with the tension, thereby relieving the connections of the tension. This arrangement protects the signal cable against dangers of being torn by external forces.

From above, according to this embodiment, it is possible to effectively prevent cables within the probe apparatus from being damaged or torn by deformations, and thus to lengthen the life of endoscope, even when the endoscope is inserted into a sinuous bodily cavity to reach a study site in a deeper part of body.

Electrical connection of the lead segments of coil 206 and signal cable 209 can be achieved securely and safely, because the lead segments are so firmly wound around the groove 208 that they can be easily soldered.

Figure 51:
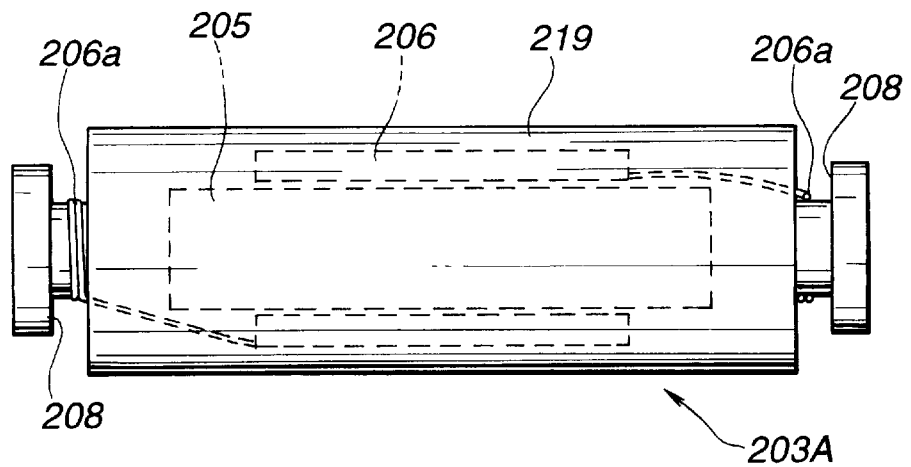

FIG. 51 illustrates a modified version 203A of the coil apparatus of the fourth embodiment. This modified version has a coil 206 prepared around a core 205, and the coil segment covered with a resin 219 to form a columnar structure with grooves 208 at both ends to act as spaces for connecting sections 210, and the columnar structure including relevant appendages is formed by molding.

It should be noted that, in FIG. 51, only the lead segment 206a of coil 206 is wound around the groove 208 for the purpose of illustration.

The operation and advantage of this embodiment is almost the same with those of the fourth embodiment.

To facilitate soldering of the lead segments of coil wire 206a and signal cables 209 at the groove 208, the columnar structure may be formed as follows: a metal plate such as copper plate is embedded in a resin, the assembly is molded in such a way as to produce a columnar structure whose groove has the metal plate exposed on its surface. Instead of molding a resin embedding a metal plate into a columnar structure, a metal fixed member incorporating, say, copper and prepared separately (capable of soldering) may be mounted onto the groove 8.

The coil 206 incorporated into the endoscope locating apparatus has been jointed on both ends to the connecting members 207 made of an insulating material to which signal cables are connected. Naturally, the connecting members have such a low affinity to solder that soldering works thereupon would not be so simple.

Accordingly, if the connecting member is made only of an insulating material, the lead segment 206a of coil wire 206 must be kept untreated until it is soldered to the lead segment of signal cable 209, or it must be firmly wound around that insulating connecting member.

If the lead segment 206a is kept untreated, the wound part of coil wire 206 may be loosened, or a tension may be inadvertently inflicted to the wire to tear it. Thus, utmost care will be necessary when the wire is handled. Alternatively, if the lead is kept wound around the connecting member, the contact between the lead and connecting member will be so loose that the same inconvenience will arise as with the wire kept untreated. If the lead is bonded with an adhesive to the connecting member, the bonding would interfere with the intimate contact of the lead segment of coil wire to the counterpart of signal cable 209, and thus this method would be hardly practical. A most reasonable method is to solder the two leads, but a high heat is directly conveyed to the insulating connecting member during soldering, which is not desirable either.

As a remedy to above problem, to the connecting member may be added another member made of an electroconductive material responsive to soldering, to facilitate soldering works while the two lead segments in question are joined in contact with that member.

Figure 52:
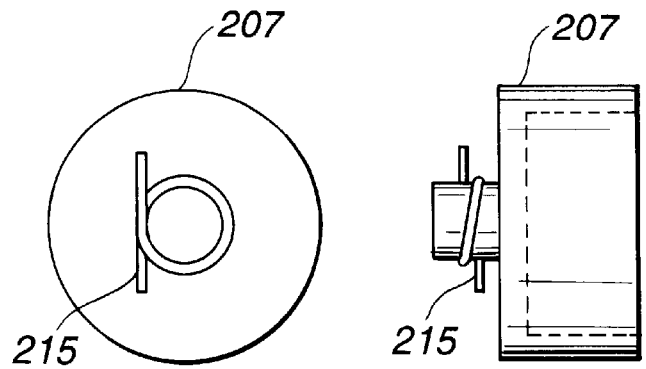
Figure 53:
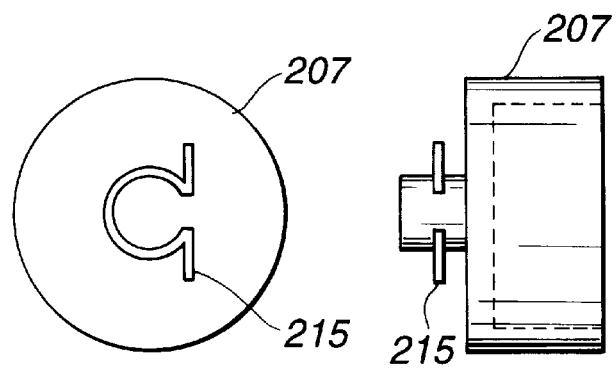

In this case, as shown in FIG. 52, a metal member 215 may be wound around the projection of connecting member 207, or, as shown in FIG. 53, the metal member 215 may be bonded to the projection.

Figure 54:
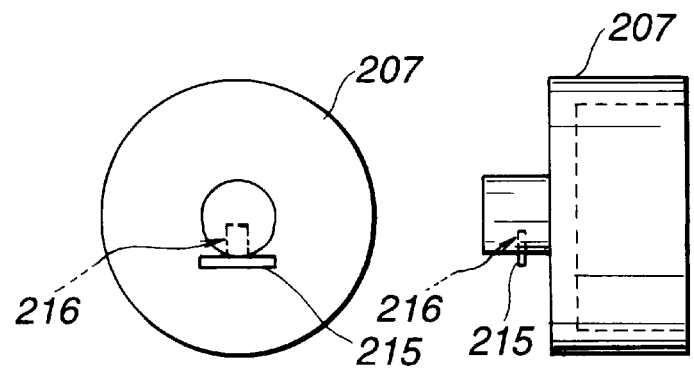

Further, as shown in FIG. 54, when a connecting member 207 is prepared from an insulating material, a depression 216 is formed on the projection thereof, and the metal member 215 may be inserted into that depression. In this case, to prevent the metal member 215 from escaping the depression, the depression 216 prepared on the projection made of an insulating material is prepared so as to give a cavity whose size is slightly larger than the metal member 215 and thus the metal member is snugly fitted to the cavity.

Figure 55:
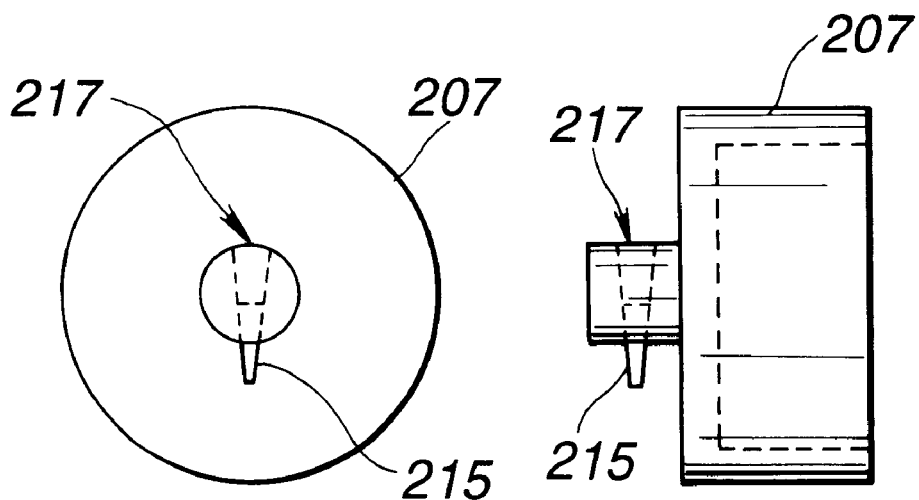

Furthermore, as shown in FIG. 55, a hole 217 with a taper may be prepared through the protrusion of connecting member 207 made of an insulating material, and a metal member 215 with the same taper may be inserted into that hole. This method is also effective for preventing escape of the metal member 215 from the connecting member 207.

Figure 56:
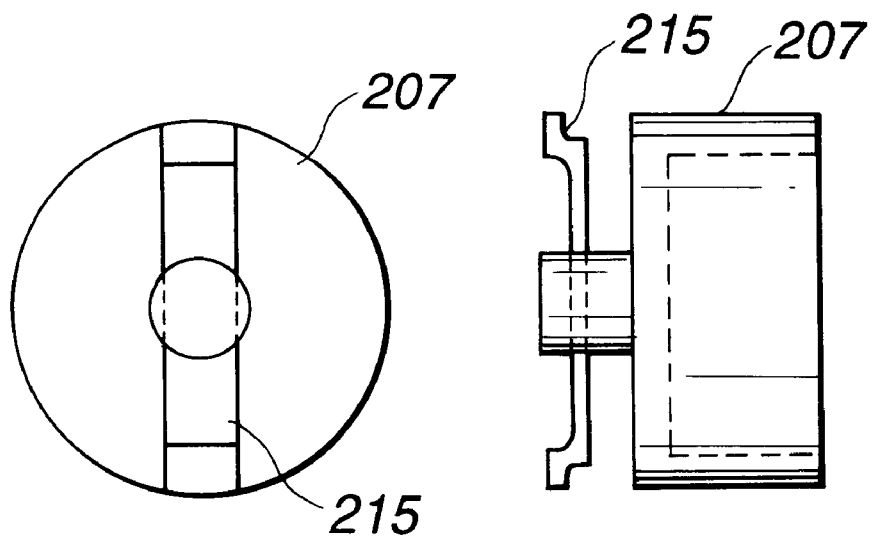
Figure 57:
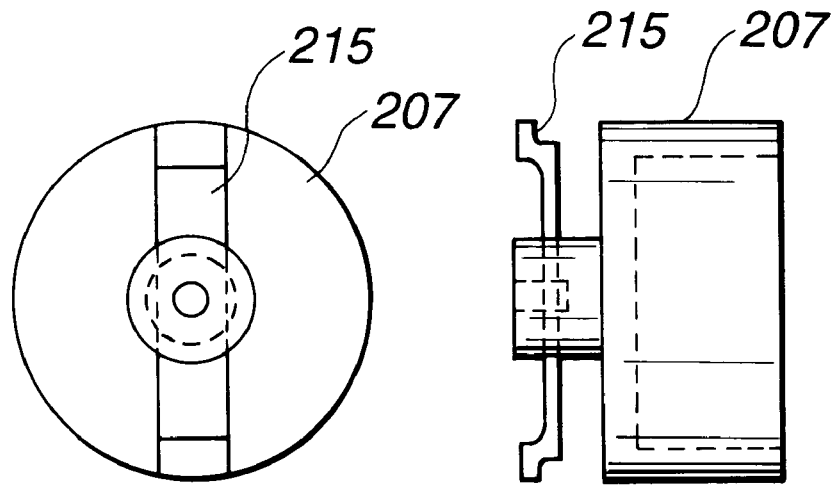
Figure 58:
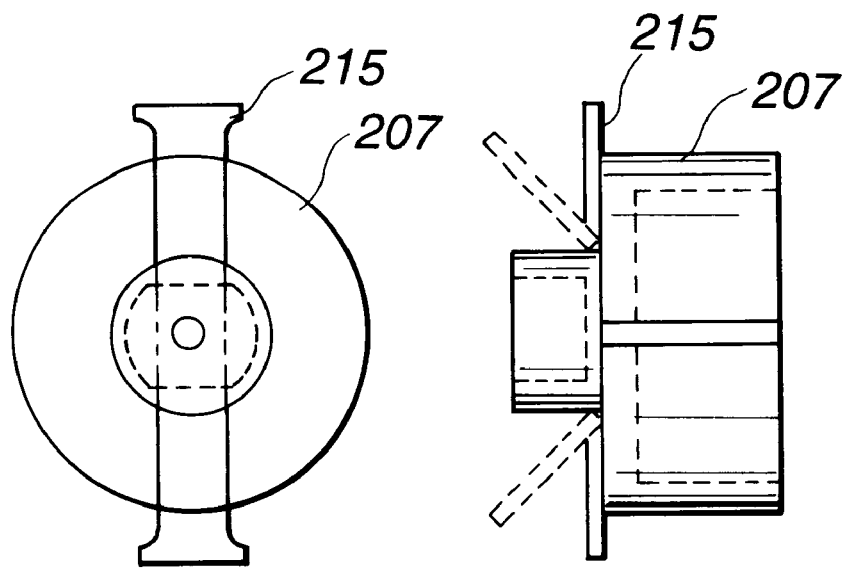

Recently, methods as indicated by FIGS. 56 to 58 have been adopted. Namely, a metal member 215 has been set in a molding frame, and a resin (an insulating material) is poured into that frame to produce a connecting member 207 with the metal member arranged at a proper place.

As shown in FIGS. 52 to 58, in this embodiment, a highly electroconductive metal member 215 is attached to the insulating connecting member 207 which is jointed with one end of the coil 206, and thus the lead segments from coil wire 206 and signal cable 209 are not necessarily connected directly. This will improve workability of resulting product.

This arrangement also allows soldering to take place at a place other than the insulating connecting member 207, which will lessen the heat transmitted to the connecting member 207 during soldering. Thus, probability of damaging connecting members 207 during production will be reduced.

Further, as the lead segment of coil wire can be fixed by soldering to the metal member 215 at a moment when the coil 206 is formed, handling is far easier than with the connecting member which is solely made of an insulating material and is not provided with such metal member.

The metal member 215 is made so as to have a size less than the internal diameter of the probe tube, because the coil to which it is attached must be kept within the long, slender tube of probe. But, when the metal member 215 has been placed in the interior of endoscope to produce a coil apparatus, contrary to the normal method where the finished coil apparatus is inserted into the probe, the metal member may be longer than normal.

When the thus produced coils are mechanically connected with, say, soft connecting members, it may become necessary to prepare a hole penetrating through the core of coils and the connecting members. In such case, a hole may be prepared on the metal member 215 to avoid passage through the connecting material.

Further, in the first embodiment, the groove 208 of connecting member 207 acts as a support upon which the lead segments are fixed to be soldered. The soldered part 210 may be covered with a non-conductive material (or insulating material) to improve its mechanical strength.

Furthermore, the connecting member 207 may be prepared as follows: a non-conductive material such as resin is molded in such a way as to have connecting sections 210 within its structure. Or, the non-conductive material may be prepared so as to cover the whole surface of coil 206, thereby to strengthen the connecting sections mechanically.

Still further, as the connection is achieved by soldering, it becomes brittle, and so fragile to bends and tensions that it may be readily torn in the presence of such deformations. To cope with that possibility, and to further strengthen the connection against mechanical shocks, unsoldered portions of lead segments may be wound adjacent to the soldered portion on the groove 208.

Still further, when the coil apparatuses thus prepared are connected together to work as a probe apparatus 201, and they are put to use, soldered parts are most fragile to external forces especially to tensions. To cope with such defect, on the connecting section may be prepared a hook around which the lead segment of signal cable 209 can be wound. This arrangement will allow the connecting section to avoid direct exposure to external forces.

The probe apparatus 201 may be inserted, instead of a channel for treatment tools, into a channel specially made for the purpose, or be incorporated as a constitutive element in the insert of endoscope.

In above description, the connecting members 207 attached to both ends of a core 205 were cited as being made of an hard, insulating material. However, when the core 205 is made of an insulating material, the connecting member 207 may be made of a hard, electroconductive material.

The Fifth Embodiment

Although in the fourth embodiment the interconnecting members 204 are placed along the sides of coil apparatuses 203, in the probe apparatus 201B of this embodiment, as shown in FIG. 59, the equivalent extends along the central axis penetrating the coil apparatuses 203B.

To allow this arrangement, as shown in FIG. 60, the connecting member 207 has a hole 221 at its center. One end of an interconnecting member 222 with a specified length is inserted into a hole of a connecting member 207 and fixed there with an adhesive, while the other end is inserted into another hole of the connecting member 207 of an adjacent coil apparatus 203B to be fixed there with the adhesive.

In other structural features, this is similar to the fourth embodiment, and thus the same symbols are attached to elements similar in function, and their explanation will be omitted here.

The operation of this embodiment is quite similar to that of fourth embodiment.

The fourth embodiment dispenses with the existence of penetrating holes 221 through connecting members 207, and thus makes it possible to obviate woks involved in preparing those holes. However, in the fourth embodiment, it is necessary to place the interconnecting member 7 along the sides of connecting members 204, which enlarges the external diameter of probe apparatus 201. In this embodiment, an interconnecting member 222 is inserted into holes of coil apparatuses and fixed there, and thus do not affect the size of probe apparatus 201B at all. Or with this embodiment, the coil apparatus is allowed to have a larger size than that of the fourth embodiment, and thus it may accommodate a larger coil, which will generate a stronger magnetic field, makes its detection easier, and finally help the location of probe to be determined more precisely.

In other structural features, this is similar to the fourth embodiment.

In the fifth embodiment described above, the connecting member 207 has a penetrating hole 221, and has an end of interconnecting member 222 inserted into it. In this case, when the interconnecting member 222 is made of a wire, the connecting member 207 has a simple, straight hole at the center, and the former is inserted into the latter to be fixed there with an adhesive, it often occurs that powder generated while the hole has been prepared adheres on the surface of interconnecting member 222 when the member 222 is inserted into the hole. The existence of powder on the surface of interconnecting member 222 often interferes with the adhesive activity of adhesive agent.

If bonding of an interconnecting member 222 to the connecting members 207 were impaired by the presence of powder, a tension inadvertently applied when an array of coil apparatuses 203B is inserted into the sheath 202 of probe apparatus 201B would tear the bonded parts. Or, even if the bonded parts had a specified strength, they would be torn off if the operator bent the probe apparatus too much by accident.

To meet such inconvenience, the connecting and interconnecting members may be modified as shown in FIG. 61.

One connecting member 207 (for example, the left one) attached to a coil apparatus 3B as shown in FIG. 60 has at the center, as shown in the left side of FIG. 61, a penetrating hole 221 and a niche to receive a core 205. The niche has the center of its bottom cut to form a conical cavity 225 which smoothly communicates with the central hole. On the other hand, as shown in FIG. 60, an interconnecting member 222 has on one end a conical appendage 226 which works as a stopper when the interconnecting member is inserted into the central hole of the corresponding connecting member 207.

When the interconnecting member 222 is inserted into the penetrating hole 221 as indicated by the arrow in FIG. 61, the stopper 226 reaches the conical cavity 225 and rests stably there to ensure secure connection of the two elements.

When the interconnecting member 222 is made of a plastic material such as a polymer, its body and stopper 226 may be molded together to form a unified structure 22.

The joint in question may have a following structure for secure connection: the niche of connecting member has a smaller niche at the center of bottom leading to the central hole, the interconnecting member 222 has a stopper made of a plastic material (which is so formed as to snugly fit to the smaller niche), and the interconnecting member 222 is inserted into the central hole until the stopper tightly fit to the smaller niche.

Further, the joint in question may have a following structure for secure connection: an interconnecting member 222 has male threads formed at both ends, two connecting members 207 sandwiching a core 205 has central holes to receive interconnecting members 222, each of the central holes has a female thread at the part to receive the threaded end of interconnecting member 222, and thus an interconnecting member 222 is inserted by screwing into the central hole to be firmly fixed there.

Furthermore, the above structure may be modified as follows: the male thread on one end of interconnecting member is so formed as to advance deeper when screwed clockwise as is normally the case, the male thread on the other end is so formed as to advance deeper when screwed counter clockwise, the first end corresponds to, say, the left side of a connecting member 207 and the second end corresponds to the right side of an adjacent connecting member, and thus when the interconnecting member 222 is screwed in one direction, its two ends advance deeper into the holes of two adjacent connecting members 207 at the same time, and this will simplify the works involved in connecting the two elements.

Still further, the modified version as shown in FIG. 61 can be further modified as follows: an interconnecting member 222 has a stopper 226 on one end and a male thread on the other, a connecting member 207 to receive the threaded end of interconnecting member 222 has a female thread cut on the part of central hole to correspond to the threaded end of interconnecting member, and thus the threaded end of interconnecting member 222 is inserted by screwing into the central hole of connecting member 207 to be firmly fixed there.

For a probe apparatus 201B to be inserted into an endoscope, its size must be so adjusted as to be able to pass through a forceps channel of endoscope. To minimize the size of probe apparatus, it is necessary to limit the size to the external width of signal transmitting cables 209. To attain this, for example, the fifth embodiment allows the signal cables 209 to run parallel only at the sites close to coil apparatuses 203B, and to be bonded there.

The Sixth Embodiment

As shown in FIG. 62, the coil apparatus 203D of this embodiment has a similar structure to that of the fourth embodiment: a plurality of coil apparatuses are connected together by a single interconnecting member 204 such that they have a specified interval between each other. However, this embodiment prevents more effectively insertion of the interconnecting member 204 into coil apparatuses from enlarging the size of probe apparatus than the fourth embodiment.

To attain this object, this embodiment, similarly to the fifth embodiment as shown in FIG. 60, has a following structure: in addition to central holes prepared at the center of connecting members 207, holes 241 penetrating the center of cores 205 are also prepared such that each of them communicates with the central holes of connecting members 207 placed at both ends, and thus, an interconnecting member 204 can be inserted through the resulting tunnel.

Then, coils are bonded with an adhesive to adjacent connecting members to form an array of coil apparatuses 203D with a specified interval between each other.

As a further modification, the lead segment 206a of coil wire is passed through a guide slit 216 to a groove 208.

In other structural features, this is similar to the fifth embodiment, and thus their explanation will be omitted here.

The operation of this embodiment is almost the same with that of the fifth embodiment. This embodiment has almost the same advantage with that of the fifth embodiment excepting that, in this embodiment, the interconnecting member 221 is less likely to escape from the coil apparatuses 203B.

This embodiment may be further modified as follows: female threads may be prepared as appropriate in the penetrating holes 241 of cores 205, and male threads are prepared on the interconnecting member 241 at a specified interval between each other such that the female and male threads will meet snugly.

The interval between adjacent core and connecting member can be adjusted after the relevant interconnecting member 221 is advanced or retreated by screwing as needed, and, after adjustment, the two elements may be bonded with an adhesive. This method of fixation allows the two elements to keep a specified interval more precisely than is possible with the sixth embodiment (where a too strong force will readily shift the coil apparatuses 203D along the long axis of interconnecting member 204.)

The Seventh Embodiment

To minimize unnecessary magnetic irradiations to maintain the precision of probe apparatus for effective endoscope monitoring, it is necessary to make the winding pattern of coil as symmetrical as possible.

To attain this object, a coil is preferably constructed as follows: a wire is wound into a coil with a number of layers such that the start end and final end come to the same side of coil. An array of coils with such construction will generate magnetic fields whose center coincides with that of cores.

What is shown in FIG. 63 is a concrete example with such construction: a coil apparatus 203F has a core 205, the core has been bonded at both ends to connecting members 207A with two grooves 208, 208 and 207B with no such groove, a wire is wound around the core 205 to form an even number of layers (four layers in the example of FIG. 63), the lead segments 206a from start and final ends of coil wire are separately wound around respective grooves 208 and 208, and these lead segments are soldered to the corresponding lead segments from signal cables 209 to form connecting sections 210.

As a wire is wound to form an even number of layers, and its start and final ends come to the same side of the resulting coil, biases in magnetic fields arising because of individual wire turns running obliquely (or spirally) with respect to the central axis may be corrected.

To put it more precisely, the final end of a wire is allowed to come to the same side of coil with the start end, and wire turns are allowed to form an even number of layers. With this arrangement, it is possible to cancel out the tilt of magnetic field due to tilted turns in one layer (for example, a layer of an odd ordinal number) by the magnetic field similarly tilted but in the opposite direction in an adjacent layer (for example, a layer of an even ordinal number). Thus, the coil will give a theoretically expected magnetic field.

In this embodiment, the connecting members 207A and 207B have at the center penetrating holes 221 to receive the interconnecting member 222.

The Eighth Embodiment

The coil apparatus 203C of this embodiment is similar to the seventh embodiment shown in FIG. 63 except that it is devoid of a connecting member 207B without groove 208 as shown in FIG. 64. This coil apparatus will allow the probe apparatus to contract in the direction of long axis.

In other structural features, this is similar to the seventh embodiment, and the operation and advantage are also similar to those in the seventh embodiment.

FIG. 65 gives a modified version of coil apparatus 203H of the eighth embodiment. This modified version comes into being after the coil apparatus 203G shown in FIG. 64 is modified as follows: a connecting member 207A has a penetrating hole 221 to receive an interconnecting member 222, a core 205 has a dead-end hole 251 to receive and fix another interconnecting member on its free end, or the end to which a connecting member 207A is not bonded.

In other features, this is similar to the eighth embodiment, and the operation and advantage are also similar to those in the eighth embodiment.

The Ninth Embodiment

The coil apparatus 203I of this embodiment is similar to the coil apparatus 203F shown in FIG. 63 except that, as shown in FIG. 66, a coil has a penetrating hole 241 which communicates with the penetrating holes 221 of adjacent connecting members 207A and 207B, and a long interconnecting member 204 is inserted through the central tunnel thus formed to fix those elements at specified positions.

The operation and advantage of this embodiment are similar to those in the eighth embodiment.

This embodiment may be modified as follows: a coil apparatus may lack one of connecting members 207B, like the coil apparatus 203G in FIG. 64. Then, it may have, as in the modified coil apparatus 203J of FIG. 67, a connecting member 207A and a core 205 both of which have penetrating holes 221 and 241 to receive a long interconnecting member 204. The long interconnecting member fixes an array of those coil apparatuses at specified positions.

Further, in this modified version, a coaxial cable 261 is used as a signal cable: the core conductor 261a is soldered to one lead segment 206a of coil wire at one of the two grooves 208 to form a connecting section 210, and the peripheral conductor 261b is soldered to the other lead segment 206a of coil wire at the other groove 208 to form a second connecting section 210.

After the formation of connecting sections 210, extra strips of core and peripheral conductors 261a and 261b are wound by one turn around respective grooves. These extra strips of core and peripheral conductors 261a and 261b are not bare but covered with insulating coats.

Use of coaxial cables 261 will reduce the generation of unnecessary magnetic fields more effectively than the probe apparatus with twisted signal cables (when the probe apparatus is used as a source coil) or will reduce invasion of surrounding noises into signals, and thus improve the S/N ratio of collected signal data (when the probe apparatus is used as a sensor coil). Except above, this embodiment has the same operation and advantage as the seventh embodiment.

Similarly, other embodiments may use coaxial cables instead of twisted single cables to connect individual coil apparatuses, because the use of such coaxial cables would suppress the generation of unnecessary irradiating magnetic fields and noises, and prevent invasion of surrounding noises into signals. Alternatively, twisted single cables may be replaced with shielded cables.

The Tenth Embodiment

In above embodiments the connecting member 207 has a larger diameter than the core 205, which may lead to enlargement of the outer diameter of probe apparatus. This embodiment enables the outer diameter of probe apparatus to be kept shortened.

FIG. 68 gives a coil apparatus 203K with such property. A core 205 has at both ends two pits 271, and into the pits are inserted parts of connecting members 272 cylindrical in shape and made of a hard, non-conductive material, and bonded with an adhesive thereto. Around the connecting members 272 protruding from both ends of coil 206 are wound the lead segments 206a of coils 206 (formed around the cores 205), and adjacent to them are also wound the lead segments of signal cables 209. The corresponding two lead segments are soldered together to form a connecting section 210, around or adjacent to which an extra stretch of signal cable is wound in order to reinforce that connecting section 210 mechanically.

The coil apparatuses are fixed on an interconnecting member 204 at specified positions, to form an array of coil apparatuses 203K along that member.

In this embodiment, the cylindrical hollow cavity prepared in the connecting member 272 has a diameter sufficiently large to allow the passage of the interconnecting member 204. The core 205 has a penetrating hole 271 which communicates with the hollow cavities prepared in the two connecting members 272 which are attached to that core 205 at both ends. Thus, a long interconnecting member 204 can be inserted through these elements.

Signal cables 209 are wound around the interconnecting member 204 in a loose manner in the form of twisted cables, running parallel to the long axis of interconnecting member 204.

This embodiment allows the coil apparatus 203K to have a smaller outer diameter.

In FIG. 68, the coil is depicted as having mono- or an odd number of layers, but it may be composed of an even number of layers like the coil apparatus 203L shown in FIG. 69 or a modified version of this embodiment. The coil 206 with an even number of layers may have a following structure: only one end of coil which receives the start and final ends of coil wire has a niche 271 into which a connecting member 272 is inserted to be firmly bonded thereto, and the other end is kept free.

Further, in this structure, as shown in FIG. 69, the lead segments of start and final ends of coil wire are stripped of insulating coats only just before they are wound around the connecting member 272, so that no shunting arises between the two connecting sections closely apposed.

Furthermore, in the coil apparatus shown in FIG. 69, signal cables 209 have redundant sections with a lax curvature just before forming connecting sections 210, so that, even if the endoscope is bent, the bending is absorbed by these lax parts to prevent the bending force from inflicting damaging effects on those connecting sections 210, and at the same time from tearing signal cables 209 themselves.

The signal cables, instead of being given such lax curvatures, may be gently wound around the connecting member 204 as in the coil apparatus of FIG. 68.

Further, the above structure may be modified as follows: as shown in FIG. 69, the signal cables with their insulating coat intact may be further wound around the connecting sections to reinforce them, so that no shunting arises between the two connecting sections 210 closely apposed.

The Eleventh Embodiment

The coil apparatus 203M of this embodiment is similar to the coil apparatus 203J shown in FIG. 68 except that, as shown in FIG. 70, a connecting member 262 is so constructed as to facilitate soldering of two lead segments from coil wire and signal cable. Thus, the connecting member 262 protruding from a core 205 has a projection 281, around the section between the projected end 281 and the opposite end of core 205 are firmly wound the lead segments of coil wire 206a and signal cable 209, and the two lead segments are soldered together.

Further, the above embodiment concerns with a coil apparatus where, after connecting sections 210 have been formed, signal cables are further wound over the connecting sections to reinforce them. In this embodiment, however, the wound sections of signal cables to reinforce the connecting sections include bare segments of cables as well as insulated segments.

In this case, the lead segment of signal cable stripped of insulating coat is wound adjacent to the lead segment 206a of coil wire, the signal cable with insulating coat is further wound over the two lead segments, and then soldering is applied to those elements to form the connecting section 210. During this process, the insulated segment is removed of insulating coat. In this way, this embodiment allows these lead windings to take place at the same time, to simplify the procedures for the manufacture of probe apparatus.

This is the same with the tenth embodiment in other operations and advantages.

For the coil apparatus 203L shown in FIG. 69, the connecting member 272 may have a similar projection.

The Twelfth Embodiment

The coil apparatus 203N of this embodiment is produced by modifying the coil apparatus 203L shown in FIG. 69 as follows: a core 205 around which a coil 206 is formed is molded together with connecting members to form a unified structure, and then has one end cut away as shown in FIG. 71.

In this case, for the coil apparatus to have a similar structure to that of FIG. 69, it is necessary to produce a core 205 longer than the core 205 of coil apparatus of FIG. 69. This core 205 is made of a non-conductive material. In this embodiment, as in the embodiment shown in FIG. 70, the core has a projection 281 with grooves where connecting sections 210 are to be formed.

Even with above probe apparatuses 201 with various devices and elaborations to lengthen the life and durability, long and repeated use will lead to damages and breaks of signal cables or coil wires.

Further, many uncontrollable factors must inevitably intervene in the processes for the manufacture of coil apparatuses, and thus it is practically impossible to give the same characteristics to all the coil apparatuses 203i (to be represented as a whole by 203i, instead of 203, 203A, ... ) in a probe.

In above description, signal cables 209 inserted in the probe together with coil apparatuses 203i are described as having sufficiently redundant lax parts, and thus the endoscope can pass through a sinuous tract in the body without inflicting any damages to coils and cables within. To be given such feature, the coil apparatus shown in FIG. 63 may be modified as follows: signal cables 209 may extend in a spiral form (or like a curly cord) from the connecting member 210 along the long axis of interconnecting member 222. The probe apparatus with such structure, even when flexed, can prevent or reduce damages of the connecting sections 210 due to external forces, because the spiral parts of signal cables can absorb such external forces inflicted by bending.

The signal cables 209 may have sinusoidal or serpentine forms with a sufficient laxity, instead of spiral forms, and run parallel to the long axis of probe apparatus, to achieve similar effects.

The lead segment of a signal cable 209 to be fixed to a connecting section 210, or the lead segment 9 of a signal cable to be fixed on the side or slit 231 of a connecting member 207 preferably has lax portions at least close to the fixation part or in an inter-coil space. The probe apparatus with such structure, even when the endoscope is flexed, allows the connecting sections 21 to be protected against deformations by bending, because the connecting sections 210 are protected by the connecting members 207 made of a hard material, and the signal cables with a sufficient laxity absorb such deformations. Thus, this structure prevents the connecting sections 210 with signal cables 209 attached thereto from being exposed to external forces and tensions.

In the fourth embodiment, for example, the lead segments 206 of coil wire after forming a coil 206 pass through the sides of connecting member 207 to reach its groove 8, and during the passage along the sides of connecting member 207 the lead segments 206a are bonded to the sides with an adhesive. As the connecting member is made of a hard material, the lead segments may be stretched taut along the sides of connecting member until they reach the groove 208 to be wound there for fixation. When the lead segments 206a reach through guide slits 216 of connecting member 207 to the grooves 208, they may be fixed at the slits 216. When the connecting member 207 is made of a material yielding to external forces, the lead segments 206 must be given a sufficiently long extra length to meet and absorb deformations inflicted by external forces.

This invention can be applied with the same profits to a probe apparatus which has a single coil apparatus 203i on its tip. In this case, a specific point (at the tip of probe) of the endoscope, instead of the total length of endoscope, is monitored on the screen.

In the fourth embodiment, for example, this invention further includes a coil apparatus in which one lead segment, say, the lead segment 206a of coil wire is wound around the groove 208 of a connecting member, the resulting lead turns alone are soldered without being accompanied with the lead segment of signal cable 209, to form a fixed terminal there. Then, the lead segment of signal cable is loosely wound over the terminal or soldered to it with a sufficient lax part intervened. In above description soldering includes brazing such as silver brazing.

The electric connections may be established by the use of electro-conductive materials such as conductive paints. When the electric connections are established by a conductive paint, they may be strengthened by application of an adhesive thereto.

This invention also includes any partial as well as total combinations of the individual embodiments described above.

This invention further includes any structures incorporating the coil apparatuses 203i described above and the production method thereof.

It is needless to say that a wide variety of applications can be derived and elaborated from this invention, within the confine of the scope and spirit of this invention.

We claim:

1. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to extract the magnetic field signal therefrom;

a frequency extracting means to extract a specified frequency component from the signal received by the magnetic field detecting means by referring to a reference signal;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means;

a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope;

first to fourth single axis coils placed around a first specified axial line;

fifth to eighth single axis coils placed around a second axial line different from the first one;

first to eight magnetic field determining sections to determine the magnetic field intensities of first to eight single coils generated by the magnetic field generating means; and a means which determines the space occupied by the magnetic field generating means on the basis of first to eighth magnetic field intensity data obtained by the first to eighth magnetic field determining sections.

2. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means by referring to a reference signal;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means;

a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope;

first to fourth single axis coils placed around a first specified axial line;

fifth to eighth single axis coils placed around a second axial line normal to the first one;

first to eight magnetic field determining sections to determine first to eighth magnetic field intensities generated by the magnetic field generating means; and a means by which to determine the space occupied by the magnetic field generating means on the basis of first to eighth magnetic field intensity data obtained by the first to eighth magnetic field determining sections.

3. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means by referring to a reference signal;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means;

radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope;

first to fourth single axis coils placed around a first specified axial line;

fifth to eighth single axis coils placed around a second axial line parallel to the first one;

first to eight magnetic field determining sections to determine first to eighth magnetic field intensities generated by the magnetic field generating means; and a means by which to determine the space occupied by the magnetic field generating means on the basis of first to eighth magnetic field intensity data obtained by the first to eighth magnetic field determining sections.

4. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means by referring to a reference signal;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means;

a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency frequency delivering means is introduced into the insert of the endoscope;

first to fourth single axis coils placed around a first specified axial line;

fifth to eighth single axis coils placed around a second axial line parallel to the first one;

ninth to twelfth single axis coils placed around a third axial line parallel to both of the first and second ones;

first to twelfth magnetic field determining sections to determine first to twelfth magnetic field intensities generated by the magnetic field generating means; and a means by which to determine the space occupied by the magnetic field generating means on the basis of first to twelfth magnetic field intensity data obtained by the first to twelfth magnetic field determining sections.

5. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means by referring to a reference signal;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means; and a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope, and whose displaying means is to display the insertion state of an endoscope as a 3D image.

6. An apparatus used together with an endoscope to detect the insertion state of the endoscope, the apparatus comprising:

a magnetic field generating means to radiate an electromagnetic wave accompanied with a magnetic field in response to a radiofrequency signal;

a magnetic field detecting means to receive the electromagnetic wave and to detect the magnetic field signal therefrom;

a frequency extracting means to extract a specified frequency component from the signal detected by the magnetic field detecting means;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means;

a radio-frequency delivering means to deliver a radiofrequency signal to the magnetic field generating means, wherein one of: (a) first set having the magnetic field detecting and detected signal delivering means, and (b) a second set having the magnetic field generating and radio-frequency delivering means is introduced into the insert of the endoscope;

first to fourth single axis coils placed around a first specified axial line fifth to eighth single axis coils placed around a second specified axial line different from the first one;

first to eighth magnetic field determining sections to determine first to eighth magnetic field intensities generated by the magnetic field generating means; and a means by which to determine the space occupied by the magnetic field generating means on the basis of first to eighth magnetic field intensity data obtained by the first to eighth magnetic field determining sections.

7. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means;

a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope;

first to fourth single axis coils placed around a first specified axial line;

fifth to eighth single axis coils placed around a second axial line normal to the first one;

first to eighth magnetic field determining sections to determine first to eighth magnetic field intensities generated by the magnetic field generating means; and a means by which to determine the space occupied by the magnetic field generating means on the basis of first to eighth magnetic field intensity data obtained by the first to eighth magnetic field determining sections.

8. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means;

a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope;

first to fourth single axis coils placed around a first specified axial line;

fifth to eighth single axis coils placed around a second axial line parallel to the first one; and first to eighth magnetic field determining sections to determine first to eighth magnetic field intensities generated by the magnetic field generating means; and a means by which to determine the space occupied by the magnetic field generating means on the basis of first to eighth magnetic field intensity data obtained by the first to eighth magnetic field determining sections.

9. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means; and a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope;

first to fourth single axis coils placed around a first specified axial line;

fifth to eighth single axis coils placed around a second axial line parallel to the first one;

ninth to twelfth single axis coils placed around a third axial line parallel to both of the first and second axial lines;

first to twelfth field intensity determining sections for determining the magnetic field intensity of the first to twelfth single axis coils generated by a source coil; and a source coil space determining section to determine the space occupied by the source coil based on the first to twelfth field intensity data obtained by the first to twelfth field intensity determining sections.

10. An apparatus used together with an endoscope to detect the insertion state of the endoscope, the apparatus comprising:

a magnetic field generating means to radiate an electromagnetic wave accompanied with a magnetic field in response to a radio-frequency signal;

a magnetic field detecting means to receive the electromagnetic wave and to detect the magnetic field signal therefrom;

a frequency extracting means to extract a specified frequency component from the signal detected by the magnetic field detecting means;

an insertion state reconstructing means to reconstruct an insertion state of an endoscope inserted into the body on the basis of the signal or the specified frequency component extracted by the frequency extracting means;

a displaying means to display the insertion state reconstructed by the insertion state reconstructing means;

a detected signal transmitting means to transmit the signal detected by the magnetic field detecting means to the foregoing insertion state reconstructing means; and a radio-frequency delivering means to deliver a radio-frequency signal to the magnetic field generating means, wherein one of: (a) a first set having the magnetic field detecting and detected signal delivering means, and (b) a second set having the magnetic field generating and radio-frequency delivering means is introduced into the insert of the endoscope, and whose displaying means is to display the insertion state of an endoscope as a 3D image.

11. An apparatus used together with an endoscope to detect the insertion state of the endoscope, the apparatus comprising:

a plurality of magnetic field generating means to radiate electromagnetic waves accompanied with magnetic fields in response to a plurality of radio-frequency signals;

a magnetic field detecting means to receive the electromagnetic waves and to detect the magnetic field signals therefrom;

a frequency extracting means to extract specified frequency components from the signals detected by the magnetic field detecting means;

an insertion state reconstructing means to reconstruct an insertion state of an endoscope inserted into the body on the basis of the signals or the specified frequency components extracted by the frequency extracting means;

a displaying means to display the insertion state reconstructed by the insertion state reconstructing means;

a detected signal transmitting means to transmit the signals detected by the magnetic field detecting means to the foregoing insertion state reconstructing means; and a radio-frequency delivering means to deliver radio-frequency signals to the magnetic field generating means, wherein one of: (a) first set having the magnetic field detecting and detected signal delivering means, and (b) a second set having the magnetic field generating and radio-frequency delivering means is introduced into the insert of the endoscope;

first to fourth single axis coils placed around a first specified axial line;

fifth to eighth single axis coils placed around a second specified axial line different from the first one;

first to eight magnetic field determining sections to determine first to eighth magnetic field intensities generated by the magnetic field generating means; and a means by which to determine the spaces occupied by the plurality of magnetic field generating means on the basis of first to eighth magnetic field intensity data obtained by the first to eighth magnetic field determining sections.

12. An endoscope-like object detecting apparatus as described in claim 11 which comprises:

a driving means to drive the plurality of magnetic field generating means in response to the plurality of radiofrequency signals;

a converting means to convert trains of signals recorded by the first to eighth magnetic field determining sections into values specific to the frequencies of the signals; and a correcting means to correct the converted values by removing interference factors among signals of different frequencies.

13. An endoscope-like object detecting apparatus as described in claim 12 which comprises:

a calculating means to multiply and sum the converted values provided by the converting means.

14. A coil apparatus for detecting endoscope location, comprising:

at least one coil of wire having a terminal and placed in an endoscope element to be inserted into a bodily cavity which is used for generating or detecting a magnetic field;

a signal wire to transmit a signal to the coil;

a connection section to connect the signal wire with the terminal of the coil; and a fixing section made of a non-conductive material around which the signal wire connected with the coil wire is wound at least at the connection section for fixation.

15. A coil apparatus for detecting endoscope location as described in claim 14 wherein the signal wire is wound at least one turn around the fixing section.

16. A coil apparatus for detecting endoscope location as described in claim 14 or 15 wherein:

the fixing section has a metal member fixed thereto, and the connecting section electrically connects the terminal of coil wire and the signal wire through the metal member.

17. A coil apparatus for detecting endoscope location as described in claim 14 or 15 wherein the fixing section made of a non-conductive material is at both ends of the coil.

18. A coil apparatus for detecting endoscope location as described in claim 14 or 15 wherein the at least one coil comprises a plurality of the coils which are interconnected with a specified interval between each other by an interconnecting material.

19. A coil apparatus for detecting endoscope location as described in claim 18 wherein:

the coil is made of wire wound around a core; and the interconnecting material is fixed to a hole at a terminal of the core.

20. A coil apparatus for detecting endoscope location as described in claim 19 wherein the interconnecting material is made of a highly elastic material.

21. A coil apparatus for detecting endoscope location as described in claim 20 wherein the highly elastic material is nitinol.

22. A coil apparatus for detecting endoscope location as described in claim 14 or 15 wherein:

the coil is comprised of wire wound to form layers in even number around a core, and wherein the starting and finishing ends of the wire are on the same end of the coil along a longitudinal axis thereof.

* * * * *